(12) United States Patent
Kanai et al.

(10) Patent No.: US 9,771,316 B2
(45) Date of Patent: Sep. 26, 2017

(54) PHENOXYALKYLAMINE COMPOUND

(71) Applicants: OSAKA UNIVERSITY, Suita-shi, Osaka (JP); KNC LABORATORIES CO., LTD., Kobe-shi, Hyogo (JP)

(72) Inventors: Yoshikatsu Kanai, Suita (JP); Shushi Nagamori, Suita (JP); Yoshihiko Kitaura, Nara (JP); Masahiro Neya, Kobe (JP); Naohiro Matsushita, Kobe (JP)

(73) Assignees: Osaka University, Osaka (JP); KNC Laboratories Co., Ltd., Kobe (JP)

( * ) Notice: Subject to any disclaimer, the term of this patent is extended or adjusted under 35 U.S.C. 154(b) by 0 days.

(21) Appl. No.: 14/761,897

(22) PCT Filed: Jan. 21, 2014

(86) PCT No.: PCT/JP2014/051144
§ 371 (c)(1),
(2) Date: Jul. 17, 2015

(87) PCT Pub. No.: WO2014/112646
PCT Pub. Date: Jul. 24, 2014

(65) Prior Publication Data
US 2015/0336876 A1  Nov. 26, 2015

(30) Foreign Application Priority Data

Jan. 21, 2013 (JP) ................ 2013-008785

(51) Int. Cl.
| | | |
|---|---|---|
| C07C 217/48 | (2006.01) |
| C07D 215/233 | (2006.01) |
| C07D 215/26 | (2006.01) |
| C07D 409/06 | (2006.01) |
| C07D 405/06 | (2006.01) |
| C07D 417/06 | (2006.01) |
| C07D 413/06 | (2006.01) |
| C07D 403/12 | (2006.01) |

(Continued)

(52) U.S. Cl.
CPC .......... *C07C 217/48* (2013.01); *C07C 211/09* (2013.01); *C07C 217/04* (2013.01); *C07C 217/72* (2013.01); *C07C 255/37* (2013.01); *C07C 255/54* (2013.01); *C07C 271/16* (2013.01); *C07C 271/20* (2013.01); *C07C 317/22* (2013.01); *C07C 317/28* (2013.01); *C07C 323/20* (2013.01); *C07C 323/25* (2013.01); *C07D 209/48* (2013.01); *C07D 213/68* (2013.01); *C07D 215/22* (2013.01); *C07D 215/233* (2013.01); *C07D 215/26* (2013.01); *C07D 263/32* (2013.01); *C07D 277/28* (2013.01); *C07D 295/08* (2013.01); *C07D 307/52* (2013.01); *C07D 333/20* (2013.01); *C07D 401/12* (2013.01); *C07D 403/12* (2013.01); *C07D 405/04* (2013.01); *C07D 405/06* (2013.01); *C07D 409/04* (2013.01); *C07D 409/06* (2013.01); *C07D 413/04* (2013.01); *C07D 413/06* (2013.01); *C07D 417/04* (2013.01); *C07D 417/06* (2013.01)

(58) Field of Classification Search
CPC ... C07C 217/48; C07C 217/04; C07C 217/72; C07C 211/04; C07C 255/37; C07C 317/22; C07C 317/28; C07C 323/20; C07C 323/25; C07D 215/233; C07D 215/26; C07D 215/22; C07D 409/06; C07D 409/04; C07D 409/48; C07D 405/06; C07D 405/04; C07D 417/06; C07D 417/04; C07D 413/06; C07D 413/04; C07D 413/68; C07D 403/12; C07D 255/54; C07D 271/16; C07D 271/20; C07D 333/20; C07D 401/12; C07D 307/52; C07D 263/32; C07D 277/28; C07D 295/08

See application file for complete search history.

(56) References Cited

U.S. PATENT DOCUMENTS

| | | |
|---|---|---|
| 4,078,071 A | 3/1978 | Walker |
| 5,387,685 A | 2/1995 | Powell et al. |

(Continued)

FOREIGN PATENT DOCUMENTS

| | | |
|---|---|---|
| JP | S52-017472 A | 2/1977 |
| JP | S53-135976 A | 11/1978 |

(Continued)

OTHER PUBLICATIONS

Gomez-Bengoa, Chem Sci, 2012, vol. 3, pp. 2949-2957.*

(Continued)

*Primary Examiner* — D M Seaman
(74) *Attorney, Agent, or Firm* — Leydig, Voit & Mayer, Ltd.

(57) ABSTRACT

The invention provides a compound having a selective inhibitory activity against highly-expressed LAT-1 in tumor cell. The compound is represented by the formula (I):

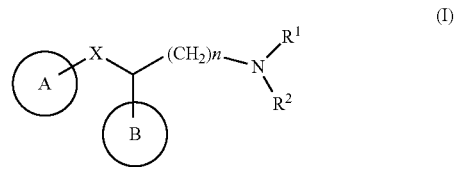

wherein each symbol is as defined in the specification, or a salt thereof, and a LAT-1 inhibitor comprising the same.

16 Claims, No Drawings

(51) Int. Cl.

| | |
|---|---|
| C07C 255/54 | (2006.01) |
| C07C 271/16 | (2006.01) |
| C07C 271/20 | (2006.01) |
| C07D 215/22 | (2006.01) |
| C07D 333/20 | (2006.01) |
| C07C 211/09 | (2006.01) |
| C07D 401/12 | (2006.01) |
| C07D 405/04 | (2006.01) |
| C07C 317/22 | (2006.01) |
| C07C 317/28 | (2006.01) |
| C07D 409/04 | (2006.01) |
| C07C 217/04 | (2006.01) |
| C07C 217/72 | (2006.01) |
| C07D 413/04 | (2006.01) |
| C07C 323/20 | (2006.01) |
| C07C 323/25 | (2006.01) |
| C07D 417/04 | (2006.01) |
| C07D 263/32 | (2006.01) |
| C07D 277/28 | (2006.01) |
| C07D 209/48 | (2006.01) |
| C07C 255/37 | (2006.01) |
| C07D 295/08 | (2006.01) |
| C07D 213/68 | (2006.01) |
| C07D 307/52 | (2006.01) |

(56) References Cited

U.S. PATENT DOCUMENTS

| | | | |
|---|---|---|---|
| 5,550,149 | A | 8/1996 | Powell et al. |
| 5,561,141 | A | 10/1996 | Powell et al. |
| 5,639,887 | A | 6/1997 | Powell et al. |
| 5,760,040 | A | 6/1998 | Yoshida et al. |
| 6,727,264 | B1 | 4/2004 | Marzabadi et al. |
| 7,067,534 | B1 | 6/2006 | Marzabadi et al. |
| 2003/0105161 | A1 | 6/2003 | Birkinshaw et al. |
| 2004/0073036 | A1 | 4/2004 | Marzabadi et al. |
| 2004/0186103 | A1 | 9/2004 | Marzabadi et al. |
| 2005/0119256 | A1 | 6/2005 | Endo et al. |
| 2006/0217418 | A1 | 9/2006 | Marzabadi et al. |
| 2007/0043080 | A1 | 2/2007 | Marzabadi et al. |
| 2008/0275067 | A1 | 11/2008 | Fowler et al. |
| 2010/0256167 | A1 | 10/2010 | Fowler et al. |
| 2010/0256168 | A1 | 10/2010 | Fowler et al. |
| 2012/0015964 | A1 | 1/2012 | Fowler et al. |
| 2013/0116266 | A1 | 5/2013 | Fowler et al. |
| 2013/0231356 | A1 | 9/2013 | Kesicki et al. |
| 2014/0121223 | A1 | 5/2014 | Fowler et al. |
| 2014/0121224 | A1 | 5/2014 | Fowler et al. |
| 2014/0378479 | A1 | 12/2014 | Kesicki et al. |

FOREIGN PATENT DOCUMENTS

| | | | |
|---|---|---|---|
| JP | 07-179422 | A | 7/1995 |
| JP | 2987643 | B2 | 10/1999 |
| JP | 2004-536104 | A | 12/2004 |
| JP | 2007-537291 | A | 12/2007 |
| JP | 2008-501707 | A | 1/2008 |
| WO | WO 01/62713 | A1 | 8/2001 |
| WO | WO 03/066574 | A1 | 8/2003 |
| WO | 2005/113556 | * | 12/2005 |
| WO | WO 2005/120511 | A1 | 12/2005 |
| WO | WO 2007/095756 | A1 | 8/2007 |

OTHER PUBLICATIONS

Martinez-Estibalez, Org Lett, VOl 11(6), 1237-1240,2009.*
Barluenga, CA105:171935, abstract only of Synthesis, vol. 12, 1125-1129, 1985.*
Barluenga et al., *Synthesis*, 12: 1125-1129 (1985).
Berger et al., *Journal of Medicinal Chemistry*, 42(12): 2145-2161 (1999).
Kumar et al., *Organic Letters*, 15(16): 4198-4201 (2013).
La Regina et al., *Journal of Medicinal Chemistry*, 51(13): 3841-3855 (2008).
Japanese Patent Office; International Search Report in International Search Report in International Patent Application No. PCT/JP2014/051144 (Apr. 15, 2014) English translation.
Yoshida et al., *Bioorganic & Medicinal Chemistry Letters*, 8: 2967-2972 (1998).
European Patent Office, Supplementary European Search Report in European Patent Application No. 14740691 (May 25, 2016).
Hayashi et al., *Oncology Reports*, 28(3): 862-866 (2012).
Imai et al., *Anticancer Research*, 30(12): 4819-4828 (2010).
Kim et al., *Anticancer Research*, 26(4B): 2943-2948 (2006).
Kim et al., *Biological and Pharmaceutical Bulletin*, 31(6): 1096-1100 (2008).
Kim et al., *Biological and Pharmaceutical Bulletin*, 33(7): 1117-1121 (2010).
Liang et al., *Nuclear Medicine and Molecular Imaging*, 45(2): 93-102 (2011).
Nawashiro et al., *International Journal of Cancer*, 119(3): 484-492 (2006).
Oda et al., *Cancer Science*, 101(1): 173-179 (2010).
Ohkawa et al., *Biochemical and Biophysical Research Communications*, 406(4): 649-655 (2011).
Shennan et al., *Oncology Reports*, 20(4): 885-889 (2008).
Yamauchi et al., *Cancer Letters*, 276(1): 95-101 (2009).
Tanino et al., "Total Synthesis of (−)-Muraymycin D2 and Its Epimer," *J. Org. Chem.*, 75(5): 1366-1377 (2010).
Japanese Patent Office, Office Action in Japanese Patent Application No. 2014-557541 (dated Jun. 13, 2017).

* cited by examiner

PHENOXYALKYLAMINE COMPOUND

CROSS-REFERENCE TO RELATED APPLICATIONS

This patent application is the U.S. national phase of International Patent Application No. PCT/JP2014/051144, filed Jan. 21, 2014, which claims the benefit of Japanese Patent Application No. 2013-008785, filed on Jan. 21, 2013, which are incorporated by reference in their entireties herein.

TECHNICAL FIELD

The present invention relates to a novel phenoxyalkylamine compound having a selective inhibitory activity against highly-expressed LAT-1 (L-type amino acid transporter 1) in tumor cell, and a LAT-1 selective inhibitor useful as an anti-cancer agent.

BACKGROUND ART

In tumor cell, cellular uptake of sugar and amino acid is enhanced for the rapid growth and the increased intracellular metabolism. The uptake is achieved by the increased functional activity and expression of transporters which play roles in cellular uptake of the nutrients. Amino acid transporters which supply essential amino acids to tumor cell are considered to be the rate-limiting steps of tumor cell growth, and therefore, the tumor growth can be controlled by suppression of the function.

Amino acid transporters are classically-known as amino acid transport systems, and many transport systems have been identified based on diversity of amino acid molecules. In tumor cell, many of essential amino acids belonging to neutral amino acids are supplied to cell via a transport system called system L. The system L is a transport system which selectively transports neutral amino acids having a bulky side chain such as branched amino acids, aromatic amino acids and the like, and it has been known as amino acid uptake inhibitor BCH (2-aminobicyclo[2.2.1]heptane-2-carboxylic acid)-sensitive transport system in the 1960's (Non-Patent Document 1).

By subsequent study, system L has been identified as twelve-transmembrane protein LAT-1 of SLC7 family (Non-Patent Document 2). In addition, it has been demonstrated that single-transmembrane protein 4F2hc (4F2 heavy chain; 4F2 heavy chain; CD98; SLC3A2) is essential to maintain the LAT-1 activity. The complex of LAT-1 and 4F2hc, which is formed via a disulfide bond, $Na^+$-independently transports neutral amino acids having a bulky side chain such as leucine, isoleucine, valine, phenylalanine, tyrosine, tryptophan, methionine, histidine and the like, and is suppressed by the above-mentioned system L-specific inhibitor BCH, and functions as a transporter showing characteristics of classical system L (Non-Patent Documents 2 and 3).

LAT-1 expression in normal tissue is limited to in brain, placenta, bone marrow, testis and the like, and the expression level is high in fetus liver, but low in adult liver. Therefore, this fact suggests that LAT-1 is carcinoembryonic antigen (Non-Patent Documents 2 and 3). The partial LAT-1 sequence has been already reported as a cancer-related sequence TA1 (Tumor-associated gene 1) wherein the function is unidentified (Non-Patent Document 4). It has been demonstrated that the LAT-1 expression is increased together with 4F2hc expression and shows characteristic distribution in primary lesion and metastasis of many human malignant tumor tissue such as colorectal cancer, stomach cancer, breast cancer, pancreatic cancer, renal cancer, prostate cancer, larynx cancer, esophageal cancer, lung cancer, brain tumor, head and neck carcinoma, genital cancer, soft tissue sarcoma and the like (Non-Patent Documents 5 to 10). In addition, it has been demonstrated that the LAT-1 expression correlates with patient prognosis in malignant tumor, and LAT-1 high expression leads to poor prognosis (Non-Patent Documents 6 to 9). LAT-1-selective substrate, $^{123}$I-IMT (3-$^{123}$I-iodo-a-methyl-L-tyrosine) is used for SPECT (Single photon emission computed tomography) diagnosis of malignant tumor, and LAT-1-selective substrate, $^{18}$F-FAMT (L-[3-$^{18}$F]-a-methyltyrosine) is used for PET (positron emission tomography) diagnosis of malignant tumor (Non-Patent Documents 11 and 12). It has been demonstrated by PET using $^{18}$F-FAMT that $^{18}$F-FAMT accumulation correlates with LAT-1 protein expression (Non-Patent Documents 12 and 13). FAMT is accumulated selectively in malignant tumor, whereas poorly in benign lesion and normal tissue, and therefore, it has been conclusively demonstrated that LAT-1 is expressed selectively in malignant tumor (Non-Patent Document 12).

It has been demonstrated that the above-mentioned BCH shows tumor cell growth inhibitory effect in vitro and tumor enlargement inhibitory effect and survival advantage of cancer-bearing mice in vivo (Non-Patent Documents 9 and 14). In addition, tumor cell growth inhibitory effect in vitro and tumor enlargement inhibitory effect in vivo of amino acid derivative, LAT-1 competitive inhibitor KYT-0353 have been disclosed (Non-Patent Document 15 and Patent Document 1). Thus, it has been already demonstrated that anti-tumor effect is achieved by inhibition of LAT-1.

As LAT-1 inhibitors, the above-mentioned system L-specific inhibitor BCH has been synthesized in the 1960's. However, the inhibitor has low affinity and no LAT-1 selectivity. Recently, as an inhibitor having LAT-1 selective and high affinity, the above-mentioned KYT-0353 has been synthesized (Non-Patent Document 15 and Patent Document 1). However, both BCH and KYT-0353 are competitive inhibitors, and the actions are reduced in vivo having a high concentration of amino acid. Therefore, it is expected that high doses thereof are requested to achieve sufficient effects.

As compounds having a structure similar to that of the phenoxyalkylamine compounds of the present invention, for example, alkylamine compounds having a phenoxy group have been reported in Patent Document 2.

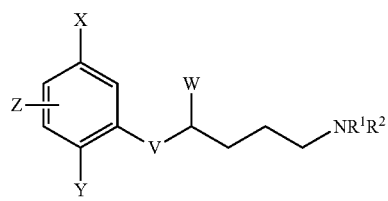

wherein
X and Y are each independently $C_{1-4}$ alkyl, $C_{1-4}$ alkoxy, halogen, $CF_3$, $OCF_3$ or the like,
m and p are each independently 0 or 2,
Z is H or F,
V is O, S(O)n or $NR^3$,
W is $C_{1-4}$ alkyl, $C_{2-4}$ alkenyl, $C_{2-4}$ alkynyl, $C_{3-4}$ cycloalkyl, a 4- to 8-membered saturated heterocyclic group or the like (each is optionally substituted by $C_{1-4}$ alkyl, $C_{1-4}$ alkoxy, $C_{1-4}$ alkylthio, halogen and the like), or phenyl or a 5- or 6-membered aromatic heterocyclic group (each is optionally substituted by halogen, $C_{1-4}$ alkyl, $C_{1-4}$ alkoxy, OH, CN and the like),
$R^1$ and $R^2$ are each independently H, $C_{1-4}$ alkyl or $C_{3-4}$ cycloalkyl, or $R^1$ and $R^2$ in combination form a 4- to 8-membered saturated nitrogen-containing heterocyclic group, and
$R^3$ is H or $C_{1-4}$ alkyl.

In addition, alkylamine compounds having a phenoxy group have also been reported in Patent Document 3.

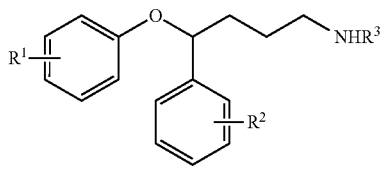

wherein
$R^1$ and $R^2$ are each independently H, halogen, $C_{1-4}$ alkyl, $C_{1-4}$ alkoxy, halo-substituted $C_{1-4}$ alkyl, halo-substituted $C_{1-4}$ alkoxy or OH, and
$R^3$ is $C_{1-4}$ alkyl.

DOCUMENT LIST

Patent Document

[Patent Document 1] WO 2008/081537
[Patent Document 2] WO 01/62713
[Patent Document 3] WO 2007/095756

Non-Patent Document

[Non-Patent Document 1] Physiol. Rev., 70, 43-77 (1990)
[Non-Patent Document 2] J. Biol. Chem., 273, 23629-23632 (1998)
[Non-Patent Document 3] Biochim. Biophys. Acta, 1514, 291-302 (2001)
[Non-Patent Document 4] Cancer Res., 55, 1152-1159 (1995)
[Non-Patent Document 5] Cancer Sci. 99, 2380-2386 (2008)
[Non-Patent Document 6] Br. J. Cancer 98, 742-748 (2008)
[Non-Patent Document 7] Pathol. Int. 59, 7-18, (2009)
[Non-Patent Document 8] Pathol. Int. 61, 281-289, (2011)
[Non-Patent Document 9] Int. J. Cancer 119, 484-492 (2006)
[Non-Patent Document 10] Cancer Sci. in press
[Non-Patent Document 11] J Nucl Med. 44, 244-246 (2003)
[Non-Patent Document 12] Clin Cancer Res. 13, 6369-6378 (2007)
[Non-Patent Document 13] Int. J. Cancer 124, 1152-1160 (2009)
[Non-Patent Document 14] Cancer Lett. 276, 95-101 (2009)
[Non-Patent Document 15] Cancer Sci. 101, 173-179 (2010)

SUMMARY OF THE INVENTION

Problems to be Solved by the Invention

The present invention aims to provide an anti-cancer agent having a LAT-1 selective inhibitory action.

Means of Solving the Problems

The present inventors have conducted intensive studies, and have found that the compound represented by the following formula has a selective inhibitory activity against LAT-1, and completed the present invention based on these findings.

Accordingly, the present invention provides the following.
[1] A compound represented by the formula (I):

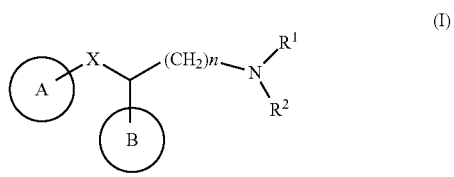

wherein
Ring A is an optionally substituted cyclic group,
Ring B is an optionally substituted cyclic group,
$R^1$ and $R^2$ are each independently a hydrogen atom, an optionally substituted alkyl group or an optionally substituted cycloalkyl group, or $R^1$ and $R^2$ in combination form an optionally substituted ring together with the nitrogen atom to which they are bonded,
X is O, S, S(O), S(O)$_2$ or NR$^3$ wherein R$^3$ is a hydrogen atom or an optionally substituted alkyl group, and
the $CH_2$ in —($CH_2$)n- is optionally replaced by O, S, S(O), S(O)$_2$ or NR$^4$ wherein R$^4$ is a hydrogen atom or an optionally substituted alkyl group, and n is an integer of 4 to 6, or a salt thereof (hereinafter sometimes to be referred to as compound (I)).
[2] The compound or salt of the above-mentioned [1], wherein Ring A is a $C_{6-14}$ aryl group, an aromatic heterocyclic group or a non-aromatic heterocyclic group, each optionally substituted.
[3] The compound or salt of the above-mentioned [1], wherein Ring A is optionally substituted phenyl.
[4] The compound or salt of the above-mentioned [1], wherein Ring B is an optionally substituted aromatic group.
[5] The compound or salt of the above-mentioned [1], wherein Ring B is phenyl or thienyl, each optionally substituted.
[6] The compound or salt of the above-mentioned [1], wherein $R^1$ and $R^2$ are each independently a hydrogen atom or a $C_{1-6}$ alkyl group, or $R^1$ and $R^2$ in combination form a 5- or 6-membered nitrogen-containing non-aromatic heterocycle together with the nitrogen atom to which they are bonded.
[7] The compound or salt of the above-mentioned [1], wherein $R^1$ and $R^2$ are each independently a hydrogen atom or a $C_{1-3}$ alkyl group.
[8] The compound or salt of the above-mentioned [1], wherein n is 4 or 5.
[9] The compound or salt of the above-mentioned [1], wherein n is 4.
[10] The compound or salt of the above-mentioned [1], wherein X is O, S, S(O), S(O)$_2$ or NH.
[11] The compound or salt of the above-mentioned [1], wherein X is O.
[12] The compound or salt of the above-mentioned [1], wherein the $CH_2$ in the —($CH_2$)n- is optionally replaced by O or S.
[13] The compound or salt of the above-mentioned [1], wherein the $CH_2$ in the —($CH_2$)n- is not replaced.
[14] A pharmaceutical composition comprising the compound or salt of any of the above-mentioned [1] to [13], and a pharmaceutically acceptable carrier.

[15] A LAT-1 inhibitor comprising the compound or salt of any of the above-mentioned [1] to [13].
[16] An anti-cancer agent comprising the compound or salt of any of the above-mentioned [1] to [13].
[17] The anti-cancer agent of the above-mentioned [16], wherein the cancer is pancreatic cancer or lung cancer.
[18] A compound represented by the formula (5):

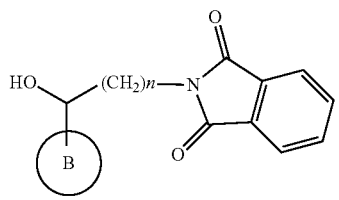

(5)

wherein
Ring B is an optionally substituted cyclic group, and
n is an integer of 4 to 6,
or a salt thereof.
[19] A compound represented by the formula (7):

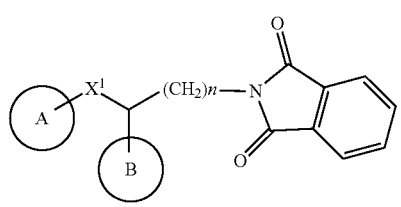

(7)

wherein
Ring A is an optionally substituted cyclic group,
Ring B is an optionally substituted cyclic group,
$X^1$ is O, S or $NR^3$ wherein $R^3$ is a hydrogen atom or an optionally substituted alkyl group, and
n is an integer of 4 to 6,
or a salt thereof.
[20] A compound represented by the formula (12):

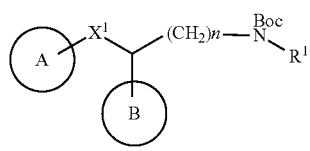

(12)

wherein
Ring A is an optionally substituted cyclic group,
Ring B is an optionally substituted cyclic group,
$R^1$ is a hydrogen atom, an optionally substituted alkyl group or an optionally substituted cycloalkyl group,
$X^1$ is O, S or $NR^3$ wherein $R^3$ is a hydrogen atom or an optionally substituted alkyl group, and
n is an integer of 4 to 6,
or a salt thereof.

Effect of the Invention

Since compound (I) has a selective inhibitory activity against highly-expressed LAT-1 in tumor cell, it is useful as an anti-cancer agent.

DETAILED DESCRIPTION OF THE INVENTION

The definition of each symbol in the formulas is explained in detail below.

Examples of the "halogen atom" in the present specification include a fluorine atom, a chlorine atom, a bromine atom and an iodine atom.

Examples of the "$C_{1-6}$ alkyl (group)" in the present specification include methyl, ethyl, propyl, isopropyl, butyl, isobutyl, sec-butyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl and the like.

Examples of the "$C_{1-10}$ alkyl group" in the present specification include methyl, ethyl, propyl, isopropyl, butyl, isobutyl, sec-butyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like.

Examples of the "$C_{2-6}$ alkenyl group" in the present specification include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl and the like.

Examples of the "$C_{2-6}$ alkynyl group" in the present specification include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like.

Examples of the "$C_{1-6}$ alkoxy (group)" in the present specification include methoxy, ethoxy, propoxy, isopropoxy, butoxy, isobutoxy, sec-butoxy, tert-butoxy and the like.

Examples of the "$C_{3-8}$ cycloalkyl (group)" in the present specification include cyclopropyl, cyclobutyl, cyclopentyl, cyclohexyl, cycloheptyl and cyclooctyl.

Examples of the "$C_{3-8}$ cycloalkenyl (group)" in the present specification include cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl) and cyclohexenyl (e.g., 2-cyclohexen-1-yl, 3-cyclohexen-1-yl).

Examples of the "$C_{4-8}$ cycloalkadienyl (group)" in the present specification include 2,4-cyclopentadien-1-yl, 2,4-cyclohexadien-1-yl, 2,5-cyclohexadien-1-yl and the like.

Examples of the "$C_{6-14}$ aryl (group)" in the present specification include phenyl, naphthyl, anthryl, phenanthryl, acenaphthylenyl, biphenylyl and the like. The "$C_{6-14}$ aryl (group)" is optionally fused with other ring(s), and examples thereof include fluorenyl, dihydronaphthyl, tetrahydronaphthyl and the like. Among them, a $C_{6-10}$ aryl group is preferable, and phenyl is particularly preferable.

Examples of the "$C_{7-13}$ aralkyl (group)" in the present specification include benzyl, phenethyl, naphthylmethyl, biphenylylmethyl and the like. Among them, a $C_{7-10}$ aralkyl group is preferable, and a benzyl group is particularly preferable.

Examples of the "heterocycle (group)" in the present specification include an aromatic heterocyclic group and a non-aromatic heterocyclic group.

Examples of the "aromatic heterocyclic group" in the present specification include a 4- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom and a nitrogen atom, and a fused aromatic heterocyclic group. Examples of the fused aromatic heterocyclic group include a group derived from a fused ring wherein a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, and the like.

Preferable examples of the aromatic heterocyclic group include
monocyclic aromatic heterocyclic groups such as furyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl, oxadiazolyl, thiadiazolyl, triazolyl, tetrazolyl, triazinyl and the like;
fused aromatic heterocyclic groups such as quinolyl, isoquinolyl, quinazolyl, quinoxalyl, benzofuranyl, benzothienyl, benzoxazolyl, benzisoxazolyl, benzothiazolyl, benzimidazolyl, benzotriazolyl, indolyl, indazolyl, carbazolyl, pyrrolopyrazinyl, imidazopyridinyl, thienopyridinyl, imidazopyrazinyl, pyrazolopyridinyl, pyrazolothienyl, pyrazolotriazinyl, pyridopyridinyl, thienopyridyl and the like;
and the like.

Examples of the non-aromatic heterocyclic group include a 4- to 7-membered (preferably 5- or 6-membered) monocyclic non-aromatic heterocyclic group containing, as a ring-constituting atom besides carbon atoms, 1 to 4 hetero atoms selected from an oxygen atom, a sulfur atom and a nitrogen atom, and a fused non-aromatic heterocyclic group. Examples of the fused non-aromatic heterocyclic group include a group derived from a fused ring wherein a ring corresponding to the 4- to 7-membered monocyclic non-aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, a group wherein the above-mentioned group is partially saturated, and the like.

Preferable examples of the non-aromatic heterocyclic group include
monocyclic non-aromatic heterocyclic groups such as azetidinyl, pyrrolidinyl, piperidinyl, morpholinyl, thiomorpholinyl, piperazinyl, hexamethyleniminyl, oxazolidinyl, thiazolidinyl, imidazolidinyl, oxazolinyl, thiazolinyl, imidazolinyl, dioxolyl, dioxolanyl, dihydrooxadiazolyl, pyranyl, tetrahydropyranyl, thiopyranyl, tetrahydrothiopyranyl, tetrahydrofuryl, pyrazolidinyl, pyrazolinyl, tetrahydropyrimidinyl, dihydrotriazolyl, tetrahydrotriazolyl and the like;
fused non-aromatic heterocyclic groups such as dihydroindolyl, dihydroisoindolyl, dihydrobenzofuranyl, dihydrobenzodioxinyl, dihydrobenzodioxepinyl, tetrahydrobenzofuranyl, chromenyl, dihydrochromenyl, dihydroquinolyl, tetrahydroquinolyl, dihydroisoquinolyl, tetrahydroisoquinolyl, dihydrophthalazinyl and the like;
and the like.

Each symbol in formula (I) is explained below.
In the formula (I), Ring A is an optionally substituted cyclic group.

Examples of the "cyclic group" of the "optionally substituted cyclic group" represented by Ring A include a $C_{3-8}$ cycloalkyl group, a $C_{3-8}$ cycloalkenyl group, a $C_{4-8}$ cycloalkadienyl group, a $C_{6-14}$ aryl group, a heterocyclic group and the like.

The "cyclic group" of the "optionally substituted cyclic group" represented by Ring A is preferably a $C_{6-14}$ aryl group (preferably phenyl, naphthyl), an aromatic heterocyclic group (preferably pyridyl, quinolyl) or a non-aromatic heterocyclic group (preferably tetrahydroquinolyl), more preferably an aromatic group [a $C_{6-14}$ aryl group (preferably phenyl, naphthyl) or an aromatic heterocyclic group (preferably pyridyl, quinolyl)], still more preferably a $C_{6-14}$ aryl group (preferably phenyl, naphthyl), particularly preferably phenyl.

Examples of the substituent of the "optionally substituted cyclic group" represented by Ring A include a $C_{1-6}$ alkyl group, a $C_{2-6}$ alkenyl group, a $C_{2-6}$ alkynyl group, a $C_{3-8}$ cycloalkyl group, a $C_{3-8}$ cycloalkenyl group, a $C_{4-8}$ cycloalkadienyl group, a $C_{6-14}$ aryl group, a $C_{7-13}$ aralkyl group, a $C_{6-14}$ aryl-$C_{2-6}$ alkenyl group, a heterocyclic group;
a hydroxy group, a $C_{1-6}$ alkoxy group, a $C_{2-6}$ alkenyloxy group, a $C_{2-6}$ alkynyloxy group, a $C_{3-8}$ cycloalkyloxy group, a $C_{3-8}$ cycloalkenyloxy group, a $C_{4-8}$ cycloalkadienyloxy group, a $C_{6-14}$ aryloxy group, a $C_{7-13}$ aralkyloxy group, a heterocyclyloxy group;
a formyl group, a $C_{1-6}$ alkyl-carbonyl group, a $C_{2-6}$ alkenyl-carbonyl group, a $C_{2-6}$ alkynyl-carbonyl group, a $C_{3-8}$ cycloalkyl-carbonyl group, a $C_{3-8}$ cycloalkenyl-carbonyl group, a $C_{4-8}$ cycloalkadienyl-carbonyl group, a $C_{6-14}$ aryl-carbonyl group, a $C_{7-13}$ aralkyl-carbonyl group, a heterocyclylcarbonyl group; a carboxy group, a $C_{1-6}$ alkoxy-carbonyl group, a $C_{2-6}$ alkenyloxy-carbonyl group, a $C_{2-6}$ alkynyloxy-carbonyl group, a $C_{3-8}$ cycloalkyloxy-carbonyl group, a $C_{3-8}$ cycloalkenyloxy-carbonyl group, a $C_{4-8}$ cycloalkadienyloxy-carbonyl group, a $C_{6-14}$ aryloxy-carbonyl group, a $C_{7-13}$ aralkyloxy-carbonyl group, a heterocyclyloxycarbonyl group;
a $C_{1-6}$ alkyl-carbonyloxy group, a $C_{2-6}$ alkenyl-carbonyloxy group, a $C_{2-6}$ alkynyl-carbonyloxy group, a $C_{3-8}$ cycloalkyl-carbonyloxy group, a $C_{3-8}$ cycloalkenyl-carbonyloxy group, a $C_{4-8}$ cycloalkadienyl-carbonyloxy group, a $C_{6-14}$ aryl-carbonyloxy group, a $C_{7-13}$ aralkyl-carbonyloxy group, a heterocyclylcarbonyloxy group;
a sulfanyl group, a $C_{1-6}$ alkylsulfanyl group, a $C_{2-6}$ alkenylsulfanyl group, a $C_{2-6}$ alkynylsulfanyl group, a $C_{3-8}$ cycloalkylsulfanyl group, a $C_{3-8}$ cycloalkenylsulfanyl group, a $C_{4-8}$ cycloalkadienylsulfanyl group, a $C_{6-14}$ arylsulfanyl group, a $C_{7-13}$ aralkylsulfanyl group, a heterocyclylsulfanyl group; a sulfinyl group, a $C_{1-6}$ alkylsulfinyl group, a $C_{2-6}$ alkenylsulfinyl group, a $C_{2-6}$ alkynylsulfinyl group, a $C_{3-8}$ cycloalkylsulfinyl group, a $C_{3-8}$ cycloalkenylsulfinyl group, a $C_{4-8}$ cycloalkadienylsulfinyl group, a $C_{6-14}$ arylsulfinyl group, a $C_{7-13}$ aralkylsulfinyl group, a heterocyclylsulfinyl group; a sulfonyl group (a sulfo group), $C_{1-6}$ alkylsulfonyl group, a $C_{2-6}$ alkenylsulfonyl group, a $C_{2-6}$ alkynylsulfonyl group, a $C_{3-8}$ cycloalkylsulfonyl group, a $C_{3-8}$ cycloalkenylsulfonyl group, a $C_{4-8}$ cycloalkadienylsulfonyl group, a $C_{6-14}$ arylsulfonyl group, a $C_{7-13}$ aralkylsulfonyl group, a heterocyclylsulfonyl group; a $C_{1-6}$ alkylsulfonyloxy group, a $C_{2-6}$ alkenylsulfonyloxy group, a $C_{2-6}$ alkynylsulfonyloxy group, a $C_{3-8}$ cycloalkylsulfonyloxy group, a $C_{3-8}$ cycloalkenylsulfonyloxy group, a $C_{4-8}$ cycloalkadienylsulfonyloxy group, a $C_{6-14}$ arylsulfonyloxy group, a $C_{7-13}$ aralkylsulfonyloxy group, a heterocyclylsulfonyloxy group;
an amino group, a mono or di-$C_{1-6}$ alkylamino group, a mono or di-$C_{2-6}$ alkenylamino group, a mono or di-$C_{2-6}$ alkynylamino group, a mono or di-$C_{3-8}$ cycloalkylamino group, a mono or di-$C_{3-8}$ cycloalkenylamino group, a mono or di-$C_{4-8}$ cycloalkadienylamino group, a mono or di-$C_{6-14}$ arylamino group, a mono or di-$C_{7-13}$ aralkylamino group, a mono or di-heterocyclylamino group; a carbamoyl group, a mono or di-$C_{1-6}$ alkylcarbamoyl group, a mono or di-$C_{2-6}$ alkenylcarbamoyl group, a mono or di-$C_{2-6}$ alkynylcarbamoyl group, a mono or di-$C_{3-8}$ cycloalkylcarbamoyl group, a mono or di-$C_{3-8}$ cycloalkenylcarbamoyl group, a mono or di-$C_{4-8}$ cycloalkadienylcarbamoyl group, a mono or di-$C_{6-14}$ arylcarbamoyl group, a mono or di-$C_{7-13}$ aralkylcarbamoyl group, a mono or di-heterocyclylcarbamoyl group;
a thiocarbamoyl group, a mono or di-$C_{1-6}$ alkylthiocarbamoyl group, a mono or di-$C_{2-6}$ alkenylthiocarbamoyl group, a mono or di-$C_{2-6}$ alkynylthiocarbamoyl group, a mono or di-$C_{3-8}$ cycloalkylthiocarbamoyl group, a mono or di-$C_{3-8}$ cycloalkenylthiocarbamoyl group, a mono or di-$C_{4-8}$ cycloalkadienylthiocarbamoyl group, a mono or di-$C_{6-14}$ arylthiocarbamoyl group, a mono or di-$C_{7-13}$ aralkylthiocarbamoyl group, a mono or di-heterocyclylthiocarbamoyl group;
a halogen atom;
a cyano group;
a nitro group;
an oxo group;
a thioxo group;
and the like. While the number of the substituents is not limited as long as it is a substitutable number, it is preferably 1 to 5, more preferably 1 to 3. When the number of the substituents is not less than 2, the respective substituents may be the same or different.

The above-mentioned substituent is optionally further substituted by the above-mentioned substituent(s). While the number of the substituents is not limited as long as it is a substitutable number, it is preferably 1 to 5, more preferably 1 to 3. When the number of the substituents is not less than 2, the respective substituents may be the same or different. Moreover, the substituent is optionally further substituted by a $C_{1-6}$ alkyl group, a $C_{2-6}$ alkenyl group, a $C_{2-6}$ alkynyl group, a $C_{3-8}$ cycloalkyl group, a $C_{3-8}$ cycloalkenyl group, a $C_{4-8}$ cycloalkadienyl group, a $C_{6-14}$ aryl group, a $C_{7-13}$ aralkyl group, a heterocyclic group, a halogen atom, a hydroxy group, a carboxy group, an amino group, a carbamoyl group, an cyano group, a nitro group, an oxo group and the like. While the number of the substituents is not limited as long as it is a substitutable number, it is preferably 1 to 5, more preferably 1 to 3. When the number of the substituents is not less than 2, the respective substituents may be the same or different.

The substituent of the "optionally substituted cyclic group" represented by Ring A is preferably selected from
(1) a halogen atom (preferably a fluorine atom, a chlorine atom),
(2) a $C_{1-6}$ alkyl group (preferably methyl, ethyl, isopropyl, sec-butyl, tert-butyl) optionally substituted by 1 to 3 substituents selected from
  (a) a halogen atom (preferably a fluorine atom),
  (b) a $C_{6-14}$ aryl group (preferably phenyl), and
  (c) a cyano group,
(3) a $C_{1-6}$ alkoxy group (preferably methoxy, ethoxy, propoxy) optionally substituted by 1 to 3 substituents selected from
  (a) a halogen atom (preferably a fluorine atom), and
  (b) a $C_{6-14}$ aryl group (preferably phenyl),
(4) a $C_{1-6}$ alkylsulfanyl group (preferably methylsulfanyl) optionally substituted by 1 to 3 halogen atoms (preferably a fluorine atom),
(5) a $C_{1-6}$ alkylsulfonyl group (preferably methylsulfonyl) optionally substituted by 1 to 3 halogen atoms (preferably a fluorine atom),
(6) a $C_{6-14}$ aryl group (preferably phenyl),
(7) a $C_{1-6}$ alkoxy-carbonyl group (preferably methoxycarbonyl),
(8) a cyano group,
(9) an nitro group,
(10) an oxo group
and the like.

The substituent is more preferably selected from
(1) a halogen atom (preferably a fluorine atom),
(2) a $C_{1-6}$ alkyl group (preferably methyl, sec-butyl) optionally substituted by 1 to 3 halogen atoms (preferably a fluorine atom),
(3) a $C_{1-6}$ alkoxy group (preferably methoxy) optionally substituted by 1 to 3 halogen atoms (preferably a fluorine atom)
and the like.

The substituent is still more preferably selected from
(1) a halogen atom (preferably a fluorine atom),
(2) a $C_{1-6}$ alkyl group (preferably methyl, sec-butyl) optionally substituted by 1 to 3 halogen atoms (preferably a fluorine atom),
(3) a $C_{1-6}$ alkoxy group (preferably methoxy) substituted by 1 to 3 halogen atoms (preferably a fluorine atom) and the like.

The substituent is particularly preferably selected from
(1) a $C_{1-6}$ alkyl group (preferably methyl) substituted by 1 to 3 halogen atoms (preferably a fluorine atom) (specifically trifluoromethyl)
and the like.

In another embodiment, the substituent is more preferably selected from
(1) a halogen atom (preferably a fluorine atom),
(2) a $C_{1-6}$ alkyl group (preferably methyl) optionally substituted by 1 to 3 halogen atoms (preferably a fluorine atom),
(3) a $C_{1-6}$ alkoxy group (preferably methoxy) optionally substituted by 1 to 3 halogen atoms (preferably a fluorine atom)
and the like.

The substituent is still more preferably selected from
(1) a halogen atom (preferably a fluorine atom),
(2) a $C_{1-6}$ alkyl group (preferably methyl) substituted by 1 to 3 halogen atoms (preferably a fluorine atom),
(3) a $C_{1-6}$ alkoxy group (preferably methoxy) substituted by 1 to 3 halogen atoms (preferably a fluorine atom)
and the like.

The substituent is particularly preferably selected from
(1) a $C_{1-6}$ alkoxy group (preferably methoxy) substituted by 1 to 3 halogen atoms (preferably a fluorine atom) (specifically trifluoromethoxy)
and the like.

Ring A is
preferably a $C_{6-14}$ aryl group (preferably phenyl, naphthyl), an aromatic heterocyclic group (preferably pyridyl, quinolyl) or a non-aromatic heterocyclic group (preferably tetrahydroquinolyl), each optionally substituted,
more preferably an optionally substituted aromatic group [a $C_{6-14}$ aryl group (preferably phenyl, naphthyl) or an aromatic heterocyclic group (preferably pyridyl, quinolyl)],
still more preferably an optionally substituted $C_{6-14}$ aryl group (preferably phenyl, naphthyl),
particularly preferably optionally substituted phenyl.

Ring A is specifically preferably a $C_{6-14}$ aryl group (preferably phenyl, naphthyl), an aromatic heterocyclic group (preferably pyridyl, quinolyl) or a non-aromatic heterocyclic group (preferably tetrahydroquinolyl) [preferably an aromatic group [a $C_{6-14}$ aryl group (preferably phenyl, naphthyl) or an aromatic heterocyclic group (preferably pyridyl, quinolyl)], still more preferably a $C_{6-14}$ aryl group (preferably phenyl, naphthyl), particularly preferably phenyl], each optionally substituted by 1 to 3 substituents selected from
(1) a halogen atom (preferably a fluorine atom, a chlorine atom),
(2) a $C_{1-6}$ alkyl group (preferably methyl, ethyl, isopropyl, sec-butyl, tert-butyl) optionally substituted by 1 to 3 substituents selected from
  (a) a halogen atom (preferably a fluorine atom),
  (b) a $C_{6-14}$ aryl group (preferably phenyl), and
  (c) a cyano group,
(3) a $C_{1-6}$ alkoxy group (preferably methoxy, ethoxy, propoxy) optionally substituted by 1 to 3 substituents selected from
  (a) a halogen atom (preferably a fluorine atom), and
  (b) a $C_{6-14}$ aryl group (preferably phenyl),
(4) a $C_{1-6}$ alkylsulfanyl group (preferably methylsulfanyl) optionally substituted by 1 to 3 halogen atoms (preferably a fluorine atom),
(5) a $C_{1-6}$ alkylsulfonyl group (preferably methylsulfonyl) optionally substituted by 1 to 3 halogen atoms (preferably a fluorine atom),
(6) a $C_{6-14}$ aryl group (preferably phenyl),
(7) a $C_{1-6}$ alkoxy-carbonyl group (preferably methoxycarbonyl),
(8) a cyano group,
(9) a nitro group, and
(10) an oxo group.

Ring A is specifically more preferably an aromatic group [a $C_{6-14}$ aryl group (preferably phenyl, naphthyl) or an aromatic heterocyclic group (preferably pyridyl, quinolyl)] [preferably a $C_{6-14}$ aryl group (preferably phenyl, naphthyl), particularly preferably phenyl] optionally substituted by 1 to 3 substituents selected from
(1) a halogen atom (preferably a fluorine atom, a chlorine atom),
(2) a $C_{1-6}$ alkyl group (preferably methyl, ethyl, isopropyl, sec-butyl, tert-butyl) optionally substituted by 1 to 3 substituents selected from
  (a) a halogen atom (preferably a fluorine atom),
  (b) a $C_{6-14}$ aryl group (preferably phenyl), and
  (c) a cyano group,
(3) a $C_{1-6}$ alkoxy group (preferably methoxy, ethoxy, propoxy) optionally substituted by 1 to 3 substituents selected from
  (a) a halogen atom (preferably a fluorine atom), and
  (b) a $C_{6-14}$ aryl group (preferably phenyl),
(4) a $C_{1-6}$ alkylsulfanyl group (preferably methylsulfanyl) optionally substituted by 1 to 3 halogen atoms (preferably a fluorine atom),
(5) a $C_{1-6}$ alkylsulfonyl group (preferably methylsulfonyl) optionally substituted by 1 to 3 halogen atoms (preferably a fluorine atom),
(6) a $C_{6-14}$ aryl group (preferably phenyl),
(7) a $C_{1-6}$ alkoxy-carbonyl group (preferably methoxycarbonyl),
(8) a cyano group, and
(9) a nitro group.

Ring A is specifically further more preferably a $C_{6-14}$ aryl group (preferably phenyl, naphthyl) [preferably phenyl] optionally substituted by 1 to 3 substituents selected from
(1) a halogen atom (preferably a fluorine atom, a chlorine atom),
(2) a $C_{1-6}$ alkyl group (preferably methyl, ethyl, isopropyl, sec-butyl, tert-butyl) optionally substituted by 1 to 3 substituents selected from
  (a) a halogen atom (preferably a fluorine atom),
  (b) a $C_{6-14}$ aryl group (preferably phenyl), and
  (c) a cyano group,
(3) a $C_{1-6}$ alkoxy group (preferably methoxy, ethoxy, propoxy) optionally substituted by 1 to 3 substituents selected from
  (a) a halogen atom (preferably a fluorine atom), and
  (b) a $C_{6-14}$ aryl group (preferably phenyl),
(4) a $C_{1-6}$ alkylsulfanyl group (preferably methylsulfanyl) optionally substituted by 1 to 3 halogen atoms (preferably a fluorine atom),
(5) a $C_{1-6}$ alkylsulfonyl group (preferably methylsulfonyl) optionally substituted by 1 to 3 halogen atoms (preferably a fluorine atom),
(6) a $C_{6-14}$ aryl group (preferably phenyl),
(7) a $C_{1-6}$ alkoxy-carbonyl group (preferably methoxycarbonyl),
(8) a cyano group, and
(9) a nitro group.

Ring A is specifically still more preferably phenyl optionally substituted by 1 to 3 substituents selected from
(1) a halogen atom (preferably a fluorine atom, a chlorine atom),
(2) a $C_{1-6}$ alkyl group (preferably methyl, ethyl, isopropyl, sec-butyl, tert-butyl) optionally substituted by 1 to 3 substituents selected from
  (a) a halogen atom (preferably a fluorine atom),
  (b) a $C_{6-14}$ aryl group (preferably phenyl), and
  (c) a cyano group,
(3) a $C_{1-6}$ alkoxy group (preferably methoxy, ethoxy, propoxy) optionally substituted by 1 to 3 substituents selected from
  (a) a halogen atom (preferably a fluorine atom), and
  (b) a $C_{6-14}$ aryl group (preferably phenyl),
(4) a $C_{1-6}$ alkylsulfanyl group (preferably methylsulfanyl) optionally substituted by 1 to 3 halogen atoms (preferably a fluorine atom),
(5) a $C_{1-6}$ alkylsulfonyl group (preferably methylsulfonyl) optionally substituted by 1 to 3 halogen atoms (preferably a fluorine atom),
(6) a $C_{6-14}$ aryl group (preferably phenyl),
(7) a $C_{1-6}$ alkoxy-carbonyl group (preferably methoxycarbonyl),
(8) a cyano group, and
(9) a nitro group.

Ring A is specifically even more preferably phenyl substituted by 1 or 2 substituents selected from
(1) a halogen atom (preferably a fluorine atom),
(2) a $C_{1-6}$ alkyl group (preferably methyl, sec-butyl) optionally substituted by 1 to 3 halogen atoms (preferably a fluorine atom), and
(3) a $C_{1-6}$ alkoxy group (preferably methoxy) optionally substituted by 1 to 3 halogen atoms (preferably a fluorine atom).

Ring A is specifically even still more preferably phenyl substituted by 1 or 2 substituents selected from
(1) a halogen atom (preferably a fluorine atom),
(2) a $C_{1-6}$ alkyl group (preferably methyl, sec-butyl) optionally substituted by 1 to 3 halogen atoms (preferably a fluorine atom), and
(3) a $C_{1-6}$ alkoxy group (preferably methoxy) substituted by 1 to 3 halogen atoms (preferably a fluorine atom).

Ring A is specifically particularly phenyl substituted by one substituent selected from (1) a $C_{1-6}$ alkyl group (preferably methyl) substituted by 1 to 3 halogen atoms (preferably a fluorine atom) (specifically trifluoromethyl) (particularly 4-trifluoromethylphenyl).

In another embodiment,

Ring A is specifically still more preferably phenyl substituted by 1 or 2 substituents selected from
(1) a halogen atom (preferably a fluorine atom),
(2) a $C_{1-6}$ alkyl group (preferably methyl) optionally substituted by 1 to 3 halogen atoms (preferably a fluorine atom), and
(3) a $C_{1-6}$ alkoxy group (preferably methoxy) optionally substituted by 1 to 3 halogen atoms (preferably a fluorine atom).

Ring A is specifically even more preferably phenyl substituted by 1 or 2 substituents selected from
(1) a halogen atom (preferably a fluorine atom),
(2) a $C_{1-6}$ alkyl group (preferably methyl) substituted by 1 to 3 halogen atoms (preferably a fluorine atom), and
(3) a $C_{1-6}$ alkoxy group (preferably methoxy) substituted by 1 to 3 halogen atoms (preferably a fluorine atom).

Ring A is specifically particularly phenyl substituted by one substituent selected from
(1) a $C_{1-6}$ alkoxy group (preferably methoxy) substituted by 1 to 3 halogen atoms (preferably a fluorine atom) (specifically trifluoromethoxy) (particularly 4-trifluoromethoxyphenyl).

In the formula (I), Ring B is an optionally substituted cyclic group.

Examples of the "optionally substituted cyclic group" represented by Ring B include those similar to the "optionally substituted cyclic group" represented by Ring A.

The "cyclic group" of the "optionally substituted cyclic group" represented by Ring B is preferably an aromatic group [a $C_{6-14}$ aryl group (preferably phenyl) or an aromatic heterocyclic group (preferably thienyl, furyl, thiazolyl, oxazolyl)], more preferably phenyl or thiazolyl, still more preferably phenyl.

The substituent of the "optionally substituted cyclic group" represented by Ring B is preferably selected from
(1) a halogen atom (preferably a fluorine atom),
(2) a $C_{1-6}$ alkyl group (preferably methyl),
(3) a $C_{1-6}$ alkoxy group (preferably methoxy) and the like.

The substituent is more preferably selected from
(1) a halogen atom (preferably a fluorine atom) and the like.

Ring B is preferably an optionally substituted aromatic group [a $C_{6-14}$ aryl group (preferably phenyl) or an aromatic heterocyclic group (preferably thienyl, furyl, thiazolyl, oxazolyl) (preferably phenyl or thiazolyl, more preferably phenyl)], more preferably phenyl or thiazolyl, each optionally substituted, still more preferably optionally substituted phenyl.

Ring B is specifically preferably an aromatic group [a $C_{6-14}$ aryl group (preferably phenyl) or an aromatic heterocyclic group (preferably thienyl, furyl, thiazolyl, oxazolyl) (preferably phenyl or thiazolyl, more preferably phenyl)] optionally substituted by 1 to 3 substituents selected from
(1) a halogen atom (preferably a fluorine atom),
(2) a $C_{1-6}$ alkyl group (preferably methyl), and
(3) a $C_{1-6}$ alkoxy group (preferably methoxy).

Ring B is specifically more preferably phenyl or thiazolyl (preferably phenyl), each optionally substituted by 1 to 3 substituents selected from
(1) a halogen atom (preferably a fluorine atom),
(2) a $C_{1-6}$ alkyl group (preferably methyl), and
(3) a $C_{1-6}$ alkoxy group (preferably methoxy).

Ring B is specifically further more preferably
(a) phenyl optionally substituted by 1 to 3 halogen atoms (preferably a fluorine atom), or
(b) thiazolyl.

Ring B is specifically still more preferably
(a) phenyl optionally substituted by 1 to 3 halogen atoms (preferably a fluorine atom).

Ring B is specifically particularly preferably unsubstituted phenyl.

In the formula (I), $R^1$ and $R^2$ are each independently a hydrogen atom, an optionally substituted alkyl group or an optionally substituted cycloalkyl group, or $R^1$ and $R^2$ in combination form an optionally substituted ring together with the nitrogen atom to which they are bonded.

The "alkyl group" of the "optionally substituted alkyl group" represented by $R^1$ or $R^2$ is preferably a $C_{1-10}$ alkyl group, more preferably a $C_{1-6}$ alkyl group, still more preferably a $C_{1-3}$ alkyl group, particularly preferably methyl.

Examples of the substituent of the "optionally substituted alkyl group" represented by $R^1$ or $R^2$ include a $C_{3-8}$ cycloalkyl group, a $C_{3-8}$ cycloalkenyl group, a $C_{4-8}$ cycloalkadienyl group, a $C_{6-14}$ aryl group, a heterocyclic group; a hydroxy group, a $C_{1-6}$ alkoxy group, a $C_{2-6}$ alkenyloxy group, a $C_{2-6}$ alkynyloxy group, a $C_{3-8}$ cycloalkyloxy group, a $C_{3-8}$ cycloalkenyloxy group, a $C_{4-8}$ cycloalkadienyloxy group, a $C_{6-14}$ aryloxy group, a $C_{7-13}$ aralkyloxy group, a heterocyclyloxy group;
a formyl group, a $C_{1-6}$ alkyl-carbonyl group, a $C_{2-6}$ alkenyl-carbonyl group, a $C_{2-6}$ alkynyl-carbonyl group, a $C_{3-8}$ cycloalkyl-carbonyl group, a $C_{3-8}$ cycloalkenyl-carbonyl group, a $C_{4-8}$ cycloalkadienyl-carbonyl group, a $C_{6-14}$ arylcarbonyl group, a $C_{7-13}$ aralkyl-carbonyl group, a heterocyclylcarbonyl group; a carboxy group, a $C_{1-6}$ alkoxy-carbonyl group, a $C_{2-6}$ alkenyloxy-carbonyl group, a $C_{2-6}$ alkynyloxy-carbonyl group, a $C_{3-8}$ cycloalkyloxy-carbonyl group, a $C_{3-8}$ cycloalkenyloxy-carbonyl group, a $C_{4-8}$ cycloalkadienyloxy-carbonyl group, a $C_{6-14}$ aryloxy-carbonyl group, a $C_{7-13}$ aralkyloxy-carbonyl group, a heterocyclyloxycarbonyl group;
a $C_{1-6}$ alkyl-carbonyloxy group, a $C_{2-6}$ alkenyl-carbonyloxy group, a $C_{2-6}$ alkynyl-carbonyloxy group, a $C_{3-8}$ cycloalkyl-carbonyloxy group, a $C_{3-8}$ cycloalkenyl-carbonyloxy group, a $C_{4-8}$ cycloalkadienyl-carbonyloxy group, a $C_{6-14}$ arylcarbonyloxy group, a $C_{7-13}$ aralkyl-carbonyloxy group, a heterocyclylcarbonyloxy group;
a sulfanyl group, a $C_{1-6}$ alkylsulfanyl group, a $C_{2-6}$ alkenylsulfanyl group, a $C_{2-6}$ alkynylsulfanyl group, a $C_{3-8}$ cycloalkylsulfanyl group, a $C_{3-8}$ cycloalkenylsulfanyl group, a $C_{4-8}$ cycloalkadienylsulfanyl group, a $C_{6-14}$ arylsulfanyl group, a $C_{7-13}$ aralkylsulfanyl group, a heterocyclylsulfanyl group; a sulfinyl group, a $C_{1-6}$ alkylsulfinyl group, a $C_{2-6}$ alkenylsulfinyl group, a $C_{2-6}$ alkynylsulfinyl group, a $C_{3-8}$ cycloalkylsulfinyl group, a $C_{3-8}$ cycloalkenylsulfinyl group, a $C_{4-8}$ cycloalkadienylsulfinyl group, a $C_{6-14}$ arylsulfinyl group, a $C_{7-13}$ aralkylsulfinyl group, a heterocyclylsulfinyl group; a sulfonyl group (a sulfo group), $C_{1-6}$ alkylsulfonyl group, a $C_{2-6}$ alkenylsulfonyl group, a $C_{2-6}$ alkynylsulfonyl group, a $C_{3-8}$ cycloalkylsulfonyl group, a $C_{3-8}$ cycloalkenylsulfonyl group, a $C_{4-8}$ cycloalkadienylsulfonyl group, a $C_{6-14}$ arylsulfonyl group, a $C_{7-13}$ aralkylsulfonyl group, a heterocyclylsulfonyl group; a $C_{1-6}$ alkylsulfonyloxy group, a $C_{2-6}$ alkenylsulfonyloxy group, a $C_{2-6}$ alkynylsulfonyloxy group, a $C_{3-8}$ cycloalkylsulfonyloxy group, a $C_{3-8}$ cycloalkenylsulfonyloxy group, a $C_{4-8}$ cycloalkadienylsulfonyloxy group, a $C_{6-14}$ arylsulfonyloxy group, a $C_{7-13}$ aralkylsulfonyloxy group, a heterocyclylsulfonyloxy group;
an amino group, a mono or di-$C_{1-6}$ alkylamino group, a mono or di-$C_{2-6}$ alkenylamino group, a mono or di-$C_{2-6}$ alkynylamino group, a mono or di-$C_{3-8}$ cycloalkylamino group, a mono or di-$C_{3-8}$ cycloalkenylamino group, a mono or di-$C_{4-8}$ cycloalkadienylamino group, a mono or di-$C_{6-14}$ arylamino group, a mono or di-$C_{7-13}$ aralkylamino group, a mono or di-heterocyclylamino group; a carbamoyl group, a mono or di-$C_{1-6}$ alkylcarbamoyl group, a mono or di-$C_{2-6}$ alkenylcarbamoyl group, a mono or di-$C_{2-6}$ alkynylcarbamoyl group, a mono or di-$C_{3-8}$ cycloalkylcarbamoyl group, a mono or di-$C_{3-8}$ cycloalkenylcarbamoyl group, a mono or di-$C_{4-8}$ cycloalkadienylcarbamoyl group, a mono or di-$C_{6-14}$ arylcarbamoyl group, a mono or di-$C_{7-13}$ aralkylcarbamoyl group, a mono or di-heterocyclylcarbamoyl group;

a thiocarbamoyl group, a mono or di-$C_{1-6}$ alkylthiocarbamoyl group, a mono or di-$C_{2-6}$ alkenylthiocarbamoyl group, a mono or di-$C_{2-6}$ alkynylthiocarbamoyl group, a mono or di-$C_{3-8}$ cycloalkylthiocarbamoyl group, a mono or di-$C_{3-8}$ cycloalkenylthiocarbamoyl group, a mono or di-$C_{4-8}$ cycloalkadienylthiocarbamoyl group, a mono or di-$C_{6-14}$ arylthiocarbamoyl group, a mono or di-$C_{7-13}$ aralkylthiocarbamoyl group, a mono or di-heterocyclylthiocarbamoyl group;

a halogen atom;
a cyano group;
a nitro group;
an oxo group;
a thioxo group;
and the like. While the number of the substituents is not limited as long as it is a substitutable number, it is preferably 1 to 5, more preferably 1 to 3. When the number of the substituents is not less than 2, the respective substituents may be the same or different.

The above-mentioned substituent is optionally further substituted by the above-mentioned substituent(s). While the number of the substituents is not limited as long as it is a substitutable number, it is preferably 1 to 5, more preferably 1 to 3. When the number of the substituents is not less than 2, the respective substituents may be the same or different. Moreover, the substituent is optionally further substituted by a $C_{1-6}$ alkyl group, a $C_{2-6}$ alkenyl group, a $C_{2-6}$ alkynyl group, a $C_{3-8}$ cycloalkyl group, a $C_{3-8}$ cycloalkenyl group, a $C_{4-8}$ cycloalkadienyl group, a $C_{6-14}$ aryl group, a $C_{7-13}$ aralkyl group, a heterocyclic group, a halogen atom, a hydroxy group, a carboxy group, an amino group, a carbamoyl group, a cyano group, a nitro group, an oxo group and the like. While the number of the substituents is not limited as long as it is a substitutable number, it is preferably 1 to 5, more preferably 1 to 3. When the number of the substituents is not less than 2, the respective substituents may be the same or different.

The "optionally substituted alkyl group" represented by $R^1$ or $R^2$ is preferably a $C_{1-10}$ alkyl group, more preferably a $C_{1-6}$ alkyl group, still more preferably a $C_{1-3}$ alkyl group, particularly preferably methyl.

The "cycloalkyl group" of the "optionally substituted cycloalkyl group" represented by $R^1$ or $R^2$ is preferably a $C_{3-8}$ cycloalkyl group.

Examples of the substituent of the "optionally substituted cycloalkyl group" represented by $R^1$ or $R^2$ include those similar to the substituent of the "optionally substituted cyclic group" represented by Ring A.

Examples of the "ring" of the "optionally substituted ring" formed by $R^1$ and $R^2$ in combination together with the nitrogen atom to which they are bonded include a 3- to 8-membered nitrogen-containing non-aromatic heterocycle, specifically aziridine, azetidine, pyrrolidine, piperidine, piperazine, morpholine, thiomorpholine, azepane, oxazepane, thioazepane, azocane and the like. The ring is preferably a 5- or 6-membered nitrogen-containing non-aromatic heterocycle, more preferably pyrrolidine or piperidine.

Examples of the substituent of the "ring" of the "optionally substituted ring" formed by $R^1$ and $R^2$ in combination together with the nitrogen atom to which they are bonded include those similar to the substituent of the "optionally substituted cyclic group" represented by Ring A.

The "optionally substituted ring" formed by $R^1$ and $R^2$ in combination together with the nitrogen atom to which they are bonded is preferably an unsubstituted 3- to 8-membered nitrogen-containing non-aromatic heterocycle, more preferably an unsubstituted 5- or 6-membered nitrogen-containing non-aromatic heterocycle, still more preferably unsubstituted pyrrolidine or unsubstituted piperidine.

$R^1$ and $R^2$ are preferably each independently a hydrogen atom or an optionally substituted alkyl group [preferably a $C_{1-10}$ alkyl group, more preferably a $C_{1-6}$ alkyl group, still more preferably a $C_{1-3}$ alkyl group, particularly preferably methyl], or $R^1$ and $R^2$ in combination form an optionally substituted 3- to 8-membered nitrogen-containing non-aromatic heterocycle together with the nitrogen atom to which they are bonded.

$R^1$ and $R^2$ are more preferably each independently a hydrogen atom or a $C_{1-6}$ alkyl group (preferably a $C_{1-3}$ alkyl group, more preferably methyl), or $R^1$ and $R^2$ in combination form an unsubstituted 5- or 6-membered nitrogen-containing non-aromatic heterocycle (preferably pyrrolidine, piperidine) together with the nitrogen atom to which they are bonded.

$R^1$ and $R^2$ are further more preferably each independently a hydrogen atom or a $C_{1-3}$ alkyl group (preferably methyl).

$R^1$ and $R^2$ are still more preferably each independently a hydrogen atom or methyl.

$R^1$ and $R^2$ are particularly preferably each independently a hydrogen atom.

X is O, S, S(O), S(O)$_2$ or NR$^3$ wherein R$^3$ is a hydrogen atom or an optionally substituted alkyl group.

Examples of the "optionally substituted alkyl group" represented by R$^3$ include those similar to the "optionally substituted alkyl group" represented by R$^1$ or R$^2$.

X is preferably O, S, S(O), S(O)$_2$ or NH, more preferably O.

The CH$_2$ in the —(CH$_2$)n- is optionally replaced by O, S, S(O), S(O)$_2$ or NR$^4$ wherein R$^4$ is a hydrogen atom or an optionally substituted alkyl group.

Examples of the "optionally substituted alkyl group" represented by R$^4$ include those similar to the "optionally substituted alkyl group" represented by R$^1$ or R$^2$.

Examples of the —(CH$_2$)n- (n is as defined above) wherein the CH$_2$ is replaced by O, S, S(O), S(O)$_2$ or NR$^4$ wherein R$^4$ is as defined above include
—O—(CH$_2$)$_3$—,
—S—(CH$_2$)$_3$—,
—S(O)—(CH$_2$)$_3$—,
—S(O)$_2$—(CH$_2$)$_3$—,
—NR$^4$—(CH$_2$)$_3$— wherein R$^4$ is as defined above,
—CH$_2$—O—(CH$_2$)$_2$—,
—CH$_2$—S—(CH$_2$)$_2$—,
—CH$_2$—S(O)—(CH$_2$)$_2$—,
—CH$_2$—S(O)$_2$—(CH$_2$)$_2$—,
—CH$_2$—NR$^4$—(CH$_2$)$_2$— wherein R$^4$ is as defined above,
—(CH$_2$)$_2$—O—CH$_2$—,
—(CH$_2$)$_2$—S—CH$_2$—,
—(CH$_2$)$_2$—S(O)—CH$_2$—,
—(CH$_2$)$_2$—S(O)$_2$—CH$_2$—,
—(CH$_2$)$_2$—NR$^4$—CH$_2$— wherein R$^4$ is as defined above,
—(CH$_2$)$_3$—O—, —(CH$_2$)$_3$—S—,
—(CH$_2$)$_3$—S(O)—,
—(CH$_2$)$_3$—S(O)$_2$—,
—(CH$_2$)$_3$—NR$^4$— wherein R$^4$ is as defined above,
—O—(CH$_2$)$_4$—,
—S—(CH$_2$)$_4$—,
—S(O)—(CH$_2$)$_4$—,
—S(O)$_2$—(CH$_2$)$_4$—,
—NR$^4$—(CH$_2$)$_4$— wherein R$^4$ is as defined above,
—CH$_2$—O—(CH$_2$)$_3$—,
—CH$_2$—S—(CH$_2$)$_3$—,
—CH$_2$—S(O)—(CH$_2$)$_3$—,
—CH$_2$—S(O)$_2$—(CH$_2$)$_3$—,
—CH$_2$—NR$^4$—(CH$_2$)$_3$— wherein R$^4$ is as defined above,
—(CH$_2$)$_2$—O—(CH$_2$)$_2$—,
—(CH$_2$)$_2$—S—(CH$_2$)$_2$—,
—(CH$_2$)$_2$—S(O)—(CH$_2$)$_2$—,
—(CH$_2$)$_2$—S(O)$_2$—(CH$_2$)$_2$—,
—(CH$_2$)$_2$—NR$^4$—(CH$_2$)$_2$— wherein R$^4$ is as defined above,
—(CH$_2$)$_3$—O—CH$_2$—,
—(CH$_2$)$_3$—S—CH$_2$—,
—(CH$_2$)$_3$—S(O)—CH$_2$—,
—(CH$_2$)$_3$—S(O)$_2$—CH$_2$—,
—(CH$_2$)$_3$—NR$^4$—CH$_2$— wherein R$^4$ is as defined above,
—(CH$_2$)$_4$—O—,
—(CH$_2$)$_4$—S—,
—(CH$_2$)$_4$—S(O)—,
—(CH$_2$)$_4$—S(O)$_2$—,
—(CH$_2$)$_4$—NR$^4$— wherein R$^4$ is as defined above,
—O—(CH$_2$)$_5$—,
—S—(CH$_2$)$_5$—,
—S(O)—(CH$_2$)$_5$—,
—S(O)$_2$—(CH$_2$)$_5$—,
—NR$^4$—(CH$_2$)$_5$— wherein R$^4$ is as defined above,
—CH$_2$—O—(CH$_2$)$_4$—,
—CH$_2$—S—(CH$_2$)$_4$—,
—CH$_2$—S(O)—(CH$_2$)$_4$—,
—CH$_2$—S(O)$_2$—(CH$_2$)$_4$—,
—CH$_2$—NR$^4$—(CH$_2$)$_4$— wherein R$^4$ is as defined above,
—(CH$_2$)$_2$—O—(CH$_2$)$_3$—,
—(CH$_2$)$_2$—S—(CH$_2$)$_3$—,
—(CH$_2$)$_2$—S(O)—(CH$_2$)$_3$—,
—(CH$_2$)$_2$—S(O)$_2$—(CH$_2$)$_3$—,
—(CH$_2$)$_2$—NR$^4$—(CH$_2$)$_3$— wherein R$^4$ is as defined above,
—(CH$_2$)$_3$—O—(CH$_2$)$_2$—,
—(CH$_2$)$_3$—S—(CH$_2$)$_2$—,
—(CH$_2$)$_3$—S(O)—(CH$_2$)$_2$—,
—(CH$_2$)$_3$—S(O)$_2$—(CH$_2$)$_2$—,
—(CH$_2$)$_3$—NR$^4$—(CH$_2$)$_2$— wherein R$^4$ is as defined above,
—(CH$_2$)$_4$—O—CH$_2$—,
—(CH$_2$)$_4$—S—CH$_2$—,
—(CH$_2$)$_4$—S(O)—CH$_2$—,
—(CH$_2$)$_4$—S(O)$_2$—CH$_2$—,
—(CH$_2$)$_4$—NR$^4$—CH$_2$— wherein R$^4$ is as defined above,
—(CH$_2$)$_5$—O—,
—(CH$_2$)$_5$—S—,
—(CH$_2$)$_5$—S(O)—,
—(CH$_2$)$_5$—S(O)$_2$—,
—(CH$_2$)$_5$—NR$^4$— wherein R$^4$ is as defined above
and the like.

The CH$_2$ of the —(CH$_2$)n- is preferably replaced by O or S (preferably —CH$_2$—O—(CH$_2$)$_2$—, —CH$_2$—S—(CH$_2$)$_2$—), or not replaced, more preferably not replaced.

In the formula (I), n is an integer of 4 to 6.

n is preferably 4 or 5, more preferably 4.

Preferable examples of compound (I) include the following compounds.

[Compound A]

Compound (I) wherein

Ring A is a $C_{6-14}$ aryl group (preferably phenyl, naphthyl), an aromatic heterocyclic group (preferably pyridyl, quinolyl) or a non-aromatic heterocyclic group (preferably tetrahydroquinolyl), each optionally substituted;

Ring B is an optionally substituted aromatic group [a $C_{6-14}$ aryl group (preferably phenyl) or an aromatic heterocyclic group (preferably thienyl, furyl, thiazolyl, oxazolyl) (preferably phenyl or thiazolyl, more preferably phenyl)];

R$^1$ and R$^2$ are each independently a hydrogen atom or an optionally substituted alkyl group [preferably a $C_{1-10}$ alkyl group, more preferably a $C_{1-6}$ alkyl group, still more preferably a $C_{1-3}$ alkyl group, particularly preferably methyl], or R$^1$ and R$^2$ in combination form an optionally substituted 3- to 8-membered nitrogen-containing non-aromatic heterocycle together with the nitrogen atom to which they are bonded;

X is O, S, S(O), S(O)$_2$ or NR$^3$ wherein R$^3$ is as defined above;

the CH$_2$ in the —(CH$_2$)n- is optionally replaced by O, S, S(O), S(O)$_2$ or NR$^4$ wherein R$^4$ is a hydrogen atom or an optionally substituted alkyl group; and n is an integer of 4 to 6.

[Compound B]

Compound (I) wherein

Ring A is a $C_{6-14}$ aryl group (preferably phenyl, naphthyl), an aromatic heterocyclic group (preferably pyridyl, quinolyl) or a non-aromatic heterocyclic group (preferably tetrahydroquinolyl) [preferably an aromatic group [a $C_{6-14}$ aryl group (preferably phenyl, naphthyl) or an aromatic heterocyclic group (preferably pyridyl, quinolyl)], still more preferably a $C_{6-14}$ aryl group (preferably phenyl, naphthyl), particularly preferably phenyl], each optionally substituted by 1 to 3 substituents selected from (1) a halogen atom (preferably a fluorine atom, a chlorine atom), (2) a $C_{1-6}$ alkyl group (preferably methyl, ethyl, isopropyl, sec-butyl, tert-butyl) optionally substituted by 1 to 3 substituents selected from (a) a halogen atom (preferably a fluorine atom), (b) a $C_{6-14}$ aryl group (preferably phenyl), and (c) a cyano group, (3) a $C_{1-6}$ alkoxy group (preferably methoxy, ethoxy, propoxy) optionally substituted by 1 to 3 substituents selected from (a) a halogen atom (preferably a fluorine atom), and (b) a $C_{6-14}$ aryl group (preferably phenyl), (4) a $C_{1-6}$ alkylsulfanyl group (preferably methylsulfanyl) optionally substituted by 1 to 3 halogen atoms (preferably a fluorine atom), (5) a $C_{1-6}$ alkylsulfonyl group (preferably methylsulfonyl) optionally substituted by 1 to 3 halogen atoms (preferably a fluorine atom), (6) a $C_{6-14}$ aryl group (preferably phenyl), (7) a $C_{1-6}$ alkoxy-carbonyl group (preferably methoxycarbonyl), (8) a cyano group, (9) a nitro group, and

(10) an oxo group;

Ring B is an aromatic group [a $C_{6-14}$ aryl group (preferably phenyl) or an aromatic heterocyclic group (preferably thienyl, furyl, thiazolyl, oxazolyl) (preferably phenyl or thiazolyl, more preferably phenyl)] optionally substituted by 1 to 3 substituents selected from (1) a halogen atom (preferably a fluorine atom), (2) a $C_{1-6}$ alkyl group (preferably methyl), and (3) a $C_{1-6}$ alkoxy group (preferably methoxy);

R¹ and R² are each independently a hydrogen atom or a C$_{1-6}$ alkyl group (preferably a C$_{1-3}$ alkyl group, more preferably methyl), or R¹ and R² in combination form an unsubstituted 5- or 6-membered nitrogen-containing non-aromatic heterocycle (preferably pyrrolidine, piperidine) together with the nitrogen atom to which they are bonded;
X is O, S, S(O), S(O)$_2$ or NH;
the CH$_2$ in the —(CH$_2$)n- is replaced by O or S (preferably —CH$_2$—O—(CH$_2$)$_2$—, —CH$_2$—S—(CH$_2$)$_2$—), or not replaced; and
n is 4 or 5.

[Compound C]
Compound (I) wherein
Ring A is phenyl substituted by 1 or 2 substituents selected from
(1) a halogen atom (preferably a fluorine atom),
(2) a C$_{1-6}$ alkyl group (preferably methyl, sec-butyl) optionally substituted by 1 to 3 halogen atoms (preferably a fluorine atom), and
(3) a C$_{1-6}$ alkoxy group (preferably methoxy) optionally substituted by 1 to 3 halogen atoms (preferably a fluorine atom);
Ring B is
(a) phenyl optionally substituted by 1 to 3 halogen atoms (preferably a fluorine atom), or
(b) thiazolyl;
R¹ and R² are both hydrogen atoms;
X is O;
the CH$_2$ in the —(CH$_2$)n- is not replaced; and
n is 4.

[Compound D]
Compound (I) wherein
Ring A is phenyl substituted by one substituent selected from
(1) a C$_{1-6}$ alkyl group (preferably methyl) substituted by 1 to 3 halogen atoms (preferably a fluorine atom) (specifically trifluoromethyl) (particularly 4-trifluoromethylphenyl);
Ring B is unsubstituted phenyl;
R¹ and R² are both hydrogen atoms;
X is O;
the CH$_2$ in the —(CH$_2$)n- is not replaced; and
n is 4.

[Compound E-1]
Compound (I) wherein
Ring A is phenyl substituted by 1 or 2 substituents selected from
(1) a halogen atom (preferably a fluorine atom),
(2) a C$_{1-6}$ alkyl group (preferably methyl) optionally substituted by 1 to 3 halogen atoms (preferably a fluorine atom), and
(3) a C$_{1-6}$ alkoxy group (preferably methoxy) optionally substituted by 1 to 3 halogen atoms (preferably a fluorine atom);
Ring B is unsubstituted phenyl;
R¹ and R² are both hydrogen atoms;
X is O;
the CH$_2$ in the —(CH$_2$)n- is not replaced; and
n is 4.

[Compound E-2]
Compound (I) wherein
Ring A is phenyl substituted by 1 or 2 substituents selected from
(1) a halogen atom (preferably a fluorine atom),
(2) a C$_{1-6}$ alkyl group (preferably methyl) substituted by 1 to 3 halogen atoms (preferably a fluorine atom), and
(3) a C$_{1-6}$ alkoxy group (preferably methoxy) substituted by 1 to 3 halogen atoms (preferably a fluorine atom);
Ring B is unsubstituted phenyl;
R¹ and R² are both hydrogen atoms;
X is O;
the CH$_2$ in the —(CH$_2$)n- is not replaced; and
n is 4.

[Compound E-3]
Compound (I) wherein
Ring A is phenyl substituted by one substituent selected from
(1) a C$_{1-6}$ alkoxy group (preferably methoxy) substituted by 1 to 3 halogen atoms (preferably a fluorine atom) (specifically trifluoromethoxy) (particularly 4-trifluoromethoxyphenyl);
Ring B is unsubstituted phenyl;
R¹ and R² are both hydrogen atoms;
X is O;
the CH$_2$ in the —(CH$_2$)n- is not replaced; and
n is 4.

[Compound E-4]
5-Phenyl-5-[4-(trifluoromethyl)phenoxy]pentan-1-amine or a salt thereof.
5-[3-Fluoro-4-(trifluoromethyl)phenoxy]-5-phenylpentan-1-amine or a salt thereof.
5-Phenyl-5-[4-(trifluoromethoxy)phenoxy]pentan-1-amine or a salt thereof.

[Compound E-5]
(R)-5-Phenyl-5-[4-(trifluoromethyl)phenoxy]pentan-1-amine or a salt thereof (preferably fumarate).
(S)-5-Phenyl-5-[4-(trifluoromethyl)phenoxy]pentan-1-amine or a salt thereof (preferably fumarate).
(R)-5-[3-Fluoro-4-(trifluoromethyl)phenoxy]-5-phenylpentan-1-amine or a salt thereof (preferably fumarate).
(S)-5-[3-Fluoro-4-(trifluoromethyl)phenoxy]-5-phenylpentan-1-amine or a salt thereof (preferably fumarate).
(R)-5-Phenyl-5-[4-(trifluoromethoxy)phenoxy]pentan-1-amine or a salt thereof (preferably fumarate).
(S)-5-Phenyl-5-[4-(trifluoromethoxy)phenoxy]pentan-1-amine or a salt thereof (preferably fumarate).

When compound (I) is in the form of a salt, examples of the salt include metal salts, ammonium salts, salts with an organic base, salts with an inorganic acid, salts with an organic acid, salts with a basic or acidic amino acid, and the like. Preferable examples of the metal salt include alkaline metal salts such as sodium salt, potassium salt and the like; alkaline earth metal salts such as calcium salt, magnesium salt, barium salt and the like; aluminum salt, and the like. Preferable examples of the salt with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with an inorganic acid include salts with hydrochloric acid, hydrobromic acid, nitric acid, sulfuric acid, phosphoric acid and the like. Preferable examples of the salt with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with a basic amino acid include salts with arginine, lysine, ornithine and the like. Preferable examples of the salt with an acidic amino acid include salts with aspartic acid, glutamic acid and the like.

Among the above-mentioned salts, pharmaceutically acceptable salts are preferable. When compound (I) has an acidic functional group, examples thereof include inorganic salts such as alkali metal salts (e.g., sodium salt, potassium salt etc.), alkaline-earth metal salts (e.g., calcium salt, magnesium salt etc.) and the like, ammonium salt and the like. When compound (I) has a basic functional group, examples thereof include salts with a inorganic acid such as hydrochloric acid, hydrobromic acid, nitric acid, sulfuric acid, phosphoric acid and the like, and salts with an organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

The production method of the compound of the present invention is explained below.

The production method of compound (I) is explained below by referring to representative production methods, which are not limited.

Compound (I) can be produced according to the method shown in the following Reaction Schemes 1-6 or method analogous thereto, or the like.

Each raw material compound may be in the form of a salt as long as it does not inhibit the reaction. Examples of the salt include those similar to the salt of compound (I).

Raw material compounds can be commercially available, or can be produced according to a method known per se or a method analogous thereto, unless otherwise referred to specific production method.

Compound (Ia), which is compound (I) wherein X is O, S or $NR^3$ wherein $R^3$ is as defined above and $R^1$ and $R^2$ are both hydrogen atoms, and compound (Ia'), which is compound (I) wherein X is S(O) or $S(O)_2$ and $R^1$ and $R^2$ are both hydrogen atoms, can be produced according to the method shown in Reaction Scheme 1.

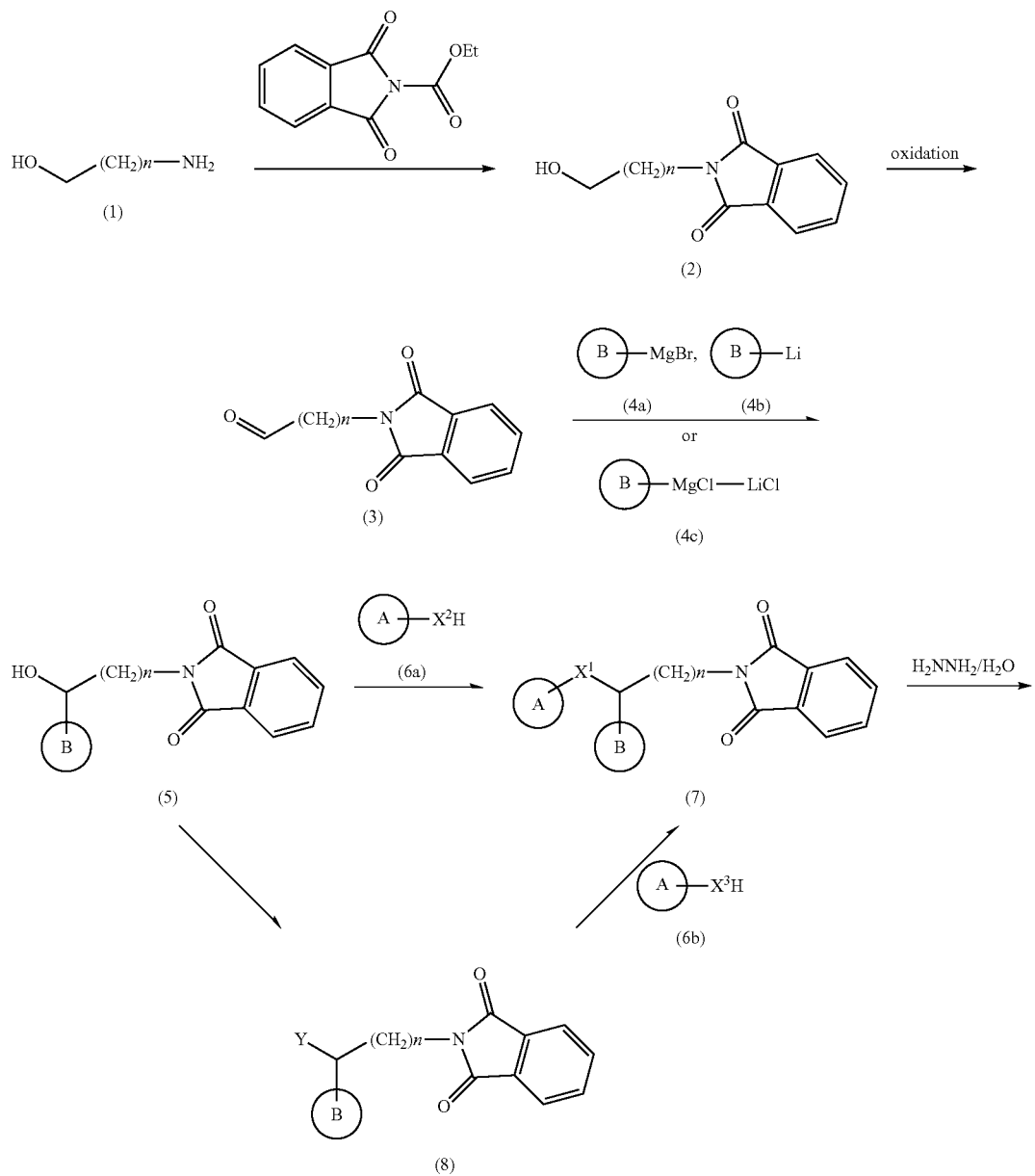

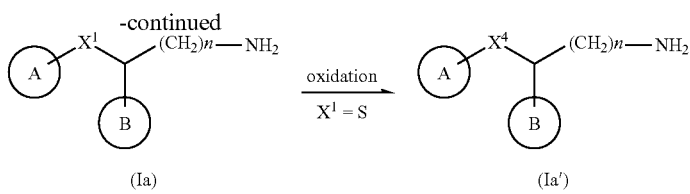

wherein $X^1$ is O, S or $NR^3$ wherein $R^3$ is as defined above, $X^2$ is O or S, $X^3$ is $NR^3$ wherein $R^3$ is as defined above, $X^4$ is S(O) or $S(O)_2$, Y is a halogen atom, and the other symbols are as defined above.

Compound (2) can be produced by reacting compound (1) with ethyl 1,3-dioxoisoindole-2-carboxylate in the presence of a base, in an inert solvent.

The amount of the ethyl 1,3-dioxoisoindole-2-carboxylate to be used is generally 1 to 5 equivalent, preferably 1 to 2 equivalent, relative to compound (1).

Examples of the base include potassium carbonate, sodium carbonate and the like. The amount of the base to be used is generally 1 to 5 equivalent, preferably 1 to 2 equivalent, relative to compound (1).

Examples of the inert solvent include ether solvents such as tetrahydrofuran (THF), diethyl ether, diisopropyl ether, tert-butyl methyl ether, 1,4-dioxane, 1,2-dimethoxyethane and the like, and the like.

The reaction temperature is generally 0° C. to 100° C., preferably 0° C. to 25° C.

The reaction time is generally 30 min to 24 hr, preferably 30 min to 2 hr.

Compound (3) can be produced by subjecting compound (2) to oxidation.

The oxidation reaction is carried out by oxidizing compound (2) with dimethyl sulfoxide in the presence of an activator and a tertiary amine, in an inert solvent.

The amount of the dimethyl sulfoxide to be used is generally 1 to 5 equivalent, preferably 1 to 2 equivalent, relative to compound (2).

Examples of the activator include pyridine-sulfur trioxide complex, oxalyl chloride, trifluoroacetic anhydride, N,N'-dicyclohexylcarbodiimide (DCC), 1-ethyl-3-(dimethylaminopropyl)carbodiimide and the like. The amount of the activator to be used is generally 1 to 5 equivalent, preferably 1 to 2 equivalent, relative to the dimethyl sulfoxide.

Examples of the tertiary amine include triethylamine, diisopropylethylamine, N-methylmorpholine, 1,8-diazabicyclo[5.4.0]undec-7-ene (DBU), 1,5-diazabicyclo[4.3.0]non-5-ene (DBN), pyridine, 2,6-lutidine and the like. The amount of the tertiary amine to be used is generally 1 to 5 equivalent, preferably 1 to 2 equivalent, relative to compound (2).

Examples of the inert solvent include halogenated hydrocarbon solvents such as dichloromethane, chloroform, 1,2-dichloroethane, carbon tetrachloride and the like; ether solvents such as diethyl ether, diisopropyl ether, tert-butyl methyl ether, tetrahydrofuran (THF), 1,4-dioxane, 1,2-dimethoxyethane and the like, and the like.

The reaction temperature is generally 0° C. to 50° C., preferably 0° C. to 25° C.

The reaction time is generally 30 min to 24 hr, preferably 30 min to 2 hr.

Compound (5) can be produced by reacting compound (3) with compound (4a), compound (4b) or compound (4c) in an inert solvent.

The amount of compound (4a), compound (4b) or compound (4c) to be used is generally 1 to 10 equivalent, preferably 1 to 2 equivalent, relative to compound (3).

Examples of the inert solvent include ether solvents such as tetrahydrofuran (THF), diethyl ether, diisopropyl ether, tert-butyl methyl ether, 1,4-dioxane, 1,2-dimethoxyethane and the like, and the like.

The reaction temperature is generally 0° C. to 100° C., preferably 0° C. to 25° C.

The reaction time is generally 30 min to 24 hr, preferably 30 min to 2 hr.

Compound (7) wherein $X^1$ is O or S can be produced by reacting compound (5) with compound (6a) in the presence of an azodicarboxylic acid diester and triphenylphosphine, in an inert solvent.

The amount of compound (6a) to be used is generally 1 to 5 equivalent, preferably 1 to 2 equivalent, relative to compound (5).

Examples of the azodicarboxylic acid diester include diethyl azodicarboxylate, diisopropyl azodicarboxylate and the like. The amount of the azodicarboxylic acid diester to be used is generally 1 to 5 equivalent, preferably 1 to 2 equivalent, relative to compound (5).

The amount of the triphenylphosphine to be used is generally 1 to 5 equivalent, preferably 1 to 2 equivalent, relative to compound (5).

Examples of the inert solvent include ether solvents such as tetrahydrofuran (THF), diethyl ether, diisopropyl ether, tert-butyl methyl ether, 1,4-dioxane, 1,2-dimethoxyethane and the like, and the like.

The reaction temperature is generally 0° C. to 50° C., preferably 0° C. to 25° C.

The reaction time is generally 30 min to 24 hr, preferably 30 min to 2 hr.

Compound (7) wherein $X^1$ is $NR^3$ wherein $R^3$ is as defined above can be produced by converting compound (5) to compound (8) by halogenation, and then reacting compound (8) with compound (6b) in the presence of a base, in an inert solvent.

The halogenation reaction of compound (5) is carried out by using a halogenating agent in the presence of triphenylphosphine, in an inert solvent.

Examples of the halogenating agent include tetrabromomethane, tetrachloromethane and the like. The amount of the halogenating agent to be used is generally 1 to 5 equivalent, preferably 1 to 2 equivalent, relative to compound (5).

The amount of the triphenylphosphine to be used is generally 1 to 5 equivalent, preferably 1 to 2 equivalent, relative to compound (5).

Examples of the inert solvent include ether solvents such as tetrahydrofuran (THF), diethyl ether, diisopropyl ether, tert-butyl methyl ether, 1,4-dioxane, 1,2-dimethoxyethane and the like, and the like.

The reaction temperature is generally 0° C. to 50° C., preferably 0° C. to 25° C.

The reaction time is generally 30 min to 24 hr, preferably 30 min to 2 hr.

In the reaction of compound (8) with compound (6b), the amount of compound (6b) to be used is generally 1 to 5 equivalent, preferably 1 to 2 equivalent, relative to compound (8)

Examples of the base include triethylamine, diisopropylethylamine, N-methylmorpholine, 1,8-diazabicyclo[5.4.0]undec-7-ene (DBU), 1,5-diazabicyclo[4.3.0]non-5-ene (DBN), pyridine, 2,6-lutidine and the like. The amount of the base to be used is generally 1 to 5 equivalent, preferably 1 to 2 equivalent, relative to compound (8).

Examples of the inert solvent include ether solvents such as tetrahydrofuran (THF), diethyl ether, diisopropyl ether, tert-butyl methyl ether, 1,4-dioxane, 1,2-dimethoxyethane and the like; aprotic polar solvents such as 1,3-dimethyl-2-imidazolidinone and the like, and the like.

The reaction temperature is generally 0° C. to 50° C., preferably 0° C. to 25° C.

The reaction time is generally 30 min to 24 hr, preferably 30 min to 2 hr.

Compound (Ia) can be produced by reacting compound (7) with hydrazine in an inert solvent.

The hydrazine is generally used in the form of a hydrate. The amount of the hydrazine to be used is generally 1 to 10 equivalent, preferably 1 to 3 equivalent, relative to compound (7).

Examples of the inert solvent include alcohol solvents such as methanol, ethanol, propanol, 2-propanol, butanol, isobutanol, tert-butanol and the like; water and the like.

The reaction temperature is generally 0° C. to 100° C., preferably 50° C. to 90° C.

The reaction time is generally 30 min to 24 hr, preferably 30 min to 4 hr.

Compound (Ia') can be produced by subjecting compound (Ia) wherein $X^1$ is S to oxidation.

The oxidation reaction is carried out by using an oxidizing agent in an inert solvent.

Examples of the oxidizing agent include m-chloroperbenzoic acid, sodium periodate and the like. The amount of the oxidizing agent to be used is generally 1 to 5 equivalent, preferably 1 to 2 equivalent, relative to compound (Ia).

Examples of the inert solvent include halogenated hydrocarbon solvents such as dichloromethane, chloroform, 1,2-dichloroethane, carbon tetrachloride and the like; alcohol solvents such as methanol, ethanol, propanol, 2-propanol, butanol, isobutanol, tert-butanol and the like, and the like.

The reaction temperature is generally 0° C. to 100° C., preferably 50° C. to 90° C.

The reaction time is generally 30 min to 24 hr, preferably 30 min to 4 hr.

Compound (Ib), which is compound (I) wherein X is O, S or $NR^3$ wherein $R^3$ is as defined above and $R^2$ is a hydrogen atom, and compound (Ib'), which is compound (I) wherein X is S(O) or $S(O)_2$ and $R^2$ is a hydrogen atom, can be produced according to the method shown in Reaction Scheme 2.

Compound (Ic), which is compound (I) wherein X is O, S or $NR^3$ wherein $R^3$ is as defined above and $R^2$ is an optionally substituted alkyl group or an optionally substituted cycloalkyl group, and compound (Ic'), which is compound (I) wherein X is S(O) or $S(O)_2$ and $R^2$ is an optionally substituted alkyl group or an optionally substituted cycloalkyl group, can be produced according to the method shown in Reaction Scheme 2.

Scheme 2

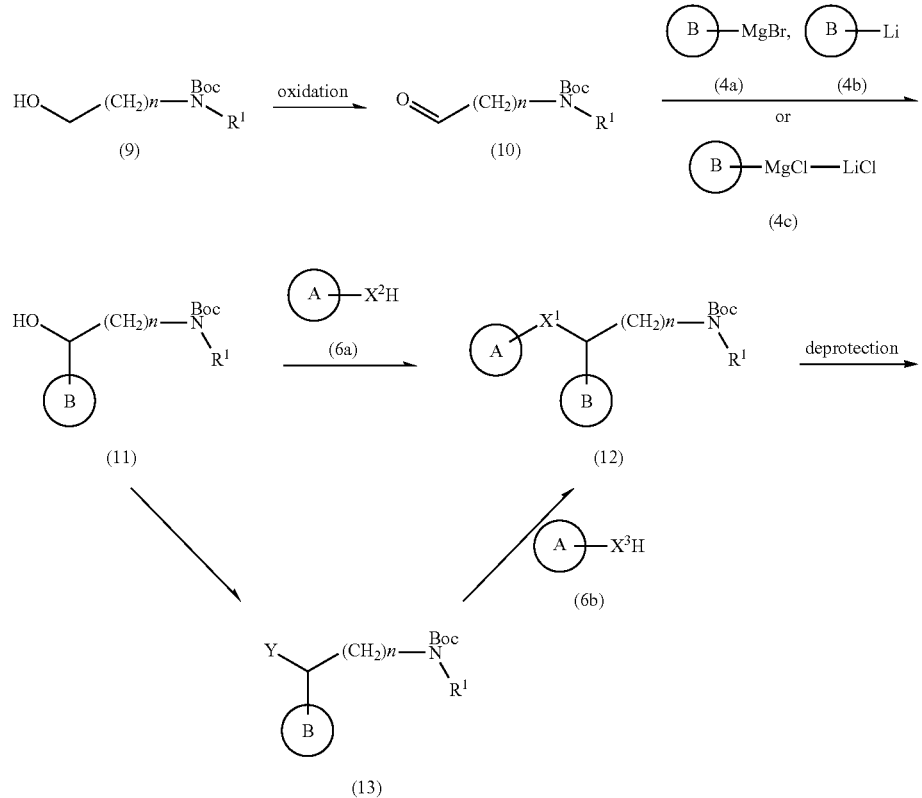

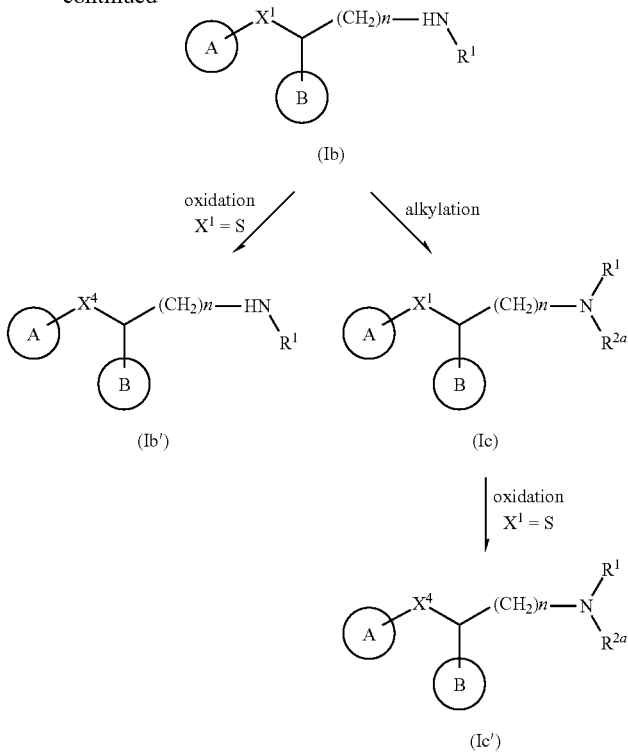

wherein $R^{2a}$ is an optionally substituted alkyl group or an optionally substituted cycloalkyl group, and the other symbols are as defined above.

Compound (10) can be produced by subjecting compound (9) to oxidation. The reaction can be carried out in the same manner as in the production of compound (3) from compound (2) in Reaction Scheme 1.

Compound (11) can be produced by reacting compound (10) with compound (4a), compound (4b) or compound (4c) in an inert solvent. The reaction can be carried out in the same manner as in the production of compound (5) from compound (3) and compound (4a), compound (4b) or compound (4c) in Reaction Scheme 1.

Compound (12) wherein $X^1$ is O or S can be produced by reacting compound (11) with compound (6a) in the presence of an azodicarboxylic acid diester and triphenylphosphine, in an inert solvent. The reaction can be carried out in the same manner as in the production of compound (7) from compound (5) and compound (6a) in Reaction Scheme 1.

Compound (12) wherein $X^1$ is $NR^3$ wherein $R^3$ is as defined above can be produced by converting compound (11) to compound (13) by halogenation, and then reacting compound (13) with compound (6b) in the presence of a base, in an inert solvent. The reaction can be carried out in the same manner as in the production of compound (7) by the conversion of compound (5) to compound (8) followed by the reaction with compound (6b).

Compound (Ib) can be produced by subjecting compound (12) to deprotection.

The deprotection reaction is carried out by reacting compound (12) with an acid.

Examples of the acid include hydrochloric acid, trifluoroacetic acid, methanesulfonic acid, toluenesulfonic acid and the like. The amount of the acid to be used is generally 1 to 100 equivalent, preferably 1 to 10 equivalent, relative to compound (12).

The reaction is carried out without solvent or in an inert solvent. Examples of the inert solvent include ester solvents such as methyl acetate, ethyl acetate, n-butyl acetate, tert-butyl acetate and the like, ether solvents such as 1,4-dioxane, 1,2-dimethoxyethane and the like, and the like.

The reaction temperature is generally 0° C. to 50° C., preferably 0° C. to 25° C.

The reaction time is generally 30 min to 24 hr, preferably 30 min to 3 hr.

Compound (Ic) can be produced by subjecting compound (Ib) to an alkylation (including cycloalkylation) in an inert solvent.

The alkylation is carried out by subjecting compound (Ib) to a reductive amination with an aldehyde or a ketone corresponding to $R^{2a}$ in the presence of a reducing agent, in an inert solvent. Where necessary, this reaction is carried out in the presence of an acid.

The amount of the aldehyde or ketone corresponding to $R^{2a}$ to be used is generally 1 to 10 equivalent, preferably 1 to 2 equivalent, relative to compound (Ib).

Examples of the reducing agent include formic acid, borohydride reagents such as sodium borohydride, sodium cyanoborohydride, sodium triacetoxyborohydride and the like, and the like. The amount of the reducing agent to be used is generally 1 to 10 equivalent, preferably 1 to 2 equivalent, relative to compound (Ib).

Examples of the acid include formic acid, acetic acid and the like. The amount of the acid to be used is generally 1 to 10 equivalent, preferably 1 to 2 equivalent, relative to compound (Ib).

Examples of the inert solvent include alcohol solvents such as methanol, ethanol, propanol, 2-propanol, butanol, isobutanol, tert-butanol and the like; water and the like.

The reaction temperature is generally 0° C. to 50° C., preferably 0° C. to 25° C.

The reaction time is generally 30 min to 24 hr, preferably 30 min to 2 hr.

The alkylation can also be carried out by reacting compound (Ib) with a halide corresponding to $R^{2a}$ in the presence of a base.

The amount of the halide corresponding to $R^{2a}$ to be used is generally 1 to 10 equivalent, preferably 1 to 2 equivalent, relative to compound (Ib).

Examples of the base include inorganic bases such as sodium hydroxide, potassium hydroxide, lithium hydroxide, barium hydroxide, sodium carbonate, potassium carbonate, cesium carbonate, sodium hydrogencarbonate, potassium hydrogencarbonate and the like; and organic bases such as triethylamine, diisopropylethylamine, N-methylmorpholine, DBU (1,8-diazabicyclo[5.4.0]undec-7-ene), DBN (1,5-diazabicyclo[4.3.0]non-5-ene), pyridine, 2,6-lutidine and the like. The amount of the base to be used is generally 1 to 10 equivalent, preferably 1 to 2 equivalent, relative to compound (Ib).

Examples of the inert solvent include ether solvents such as tetrahydrofuran (THF), diethyl ether, diisopropyl ether, tert-butyl methyl ether, 1,4-dioxane, 1,2-dimethoxyethane and the like, and the like.

The reaction temperature is generally 0° C. to 50° C., preferably 0° C. to 25° C.

The reaction time is generally 30 min to 24 hr, preferably 30 min to 2 hr.

Compound (Ib') can be produced by subjecting compound (Ib) wherein $X^1$ is S to oxidation. The reaction can be carried out in the same manner as in the production of compound (Ia') from compound (Ia) in Reaction Scheme 1.

Compound (Ic') can be produced by subjecting compound (Ic) wherein $X^1$ is S to oxidation. The reaction can be carried out in the same manner as in the production of compound (Ia') from compound (Ia) in Reaction Scheme 1.

Compound (Ib"), which is compound (I) wherein X is O, S or $NR^3$ wherein $R^3$ is as defined above, $R^1$ is an optionally substituted alkyl group or an optionally substituted cycloalkyl group and $R^2$ is a hydrogen atom, and compound (Ib'''), which is compound (I) wherein X is S(O) or $S(O)_2$, $R^1$ is an optionally substituted alkyl group or an optionally substituted cycloalkyl group and $R^2$ is a hydrogen atom, can be produced according to the method shown in Reaction Scheme 3.

Compound (Ic"), which is compound (I) wherein X is O, S or $NR^3$ wherein $R^3$ is as defined above and $R^1$ and $R^2$ are each independently an optionally substituted alkyl group or an optionally substituted cycloalkyl group, and compound (Ic'''), which is compound (I) wherein X is S(O) or $S(O)_2$ and $R^1$ and $R^2$ are each independently an optionally substituted alkyl group or an optionally substituted cycloalkyl group, can be produced according to the method shown in Reaction Scheme 3.

Scheme 3

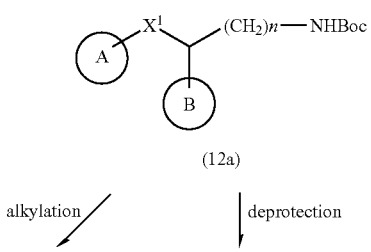

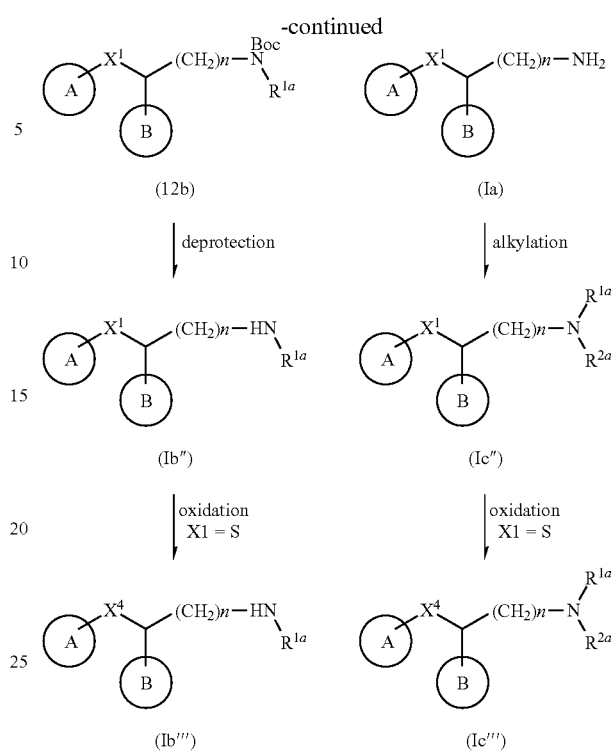

wherein $R^{1a}$ is an optionally substituted alkyl group or an optionally substituted cycloalkyl group, and the other symbols are as defined above.

Compound (Ia) can be produced by subjecting compound (12a) to deprotection. The reaction can be carried out in the same manner as in the production of compound (Ib) from compound (12) in Reaction Scheme 2.

Compound (Ic") can be produced by subjecting compound (Ia) to alkylation. The reaction can be carried out in the same manner as in the production of compound (Ic) from compound (Ib) in Reaction Scheme 2.

Compound (12b) can be produced by subjecting compound (12a) to alkylation. The reaction can be carried out in the same manner as in the method using a halide, from among the production of compound (Ic) from compound (Ib) in Reaction Scheme 2.

Compound (Ib") can be produced by subjecting compound (12b) to deprotection. The reaction can be carried out in the same manner as in the production of compound (Ib) from compound (12) in Reaction Scheme 2.

Compound (Ib''') can be produced by subjecting compound (Ib") wherein $X^1$ is S to oxidation. The reaction can be carried out in the same manner as in the production of compound (Ia') from compound (Ia) in Reaction Scheme 1.

Compound (Ic''') can be produced by subjecting compound (Ic") wherein $X^1$ is S to oxidation. The reaction can be carried out in the same manner as in the production of compound (Ia') from compound (Ia) in Reaction Scheme 1.

Compound (Id), which is compound (I) wherein X is O, S or $NR^3$ wherein $R^3$ is as defined above and $R^1$ and $R^2$ in combination form a 3- to 8-membered nitrogen-containing non-aromatic heterocycle together with the nitrogen atom to which they are bonded, and compound (Id'), which is compound (I) wherein X is S(O) or $S(O)_2$ and $R^1$ and $R^2$ in combination form a 3- to 8-membered nitrogen-containing non-aromatic heterocycle together with the nitrogen atom to which they are bonded, can be produced according to the method shown in Reaction Scheme 4.

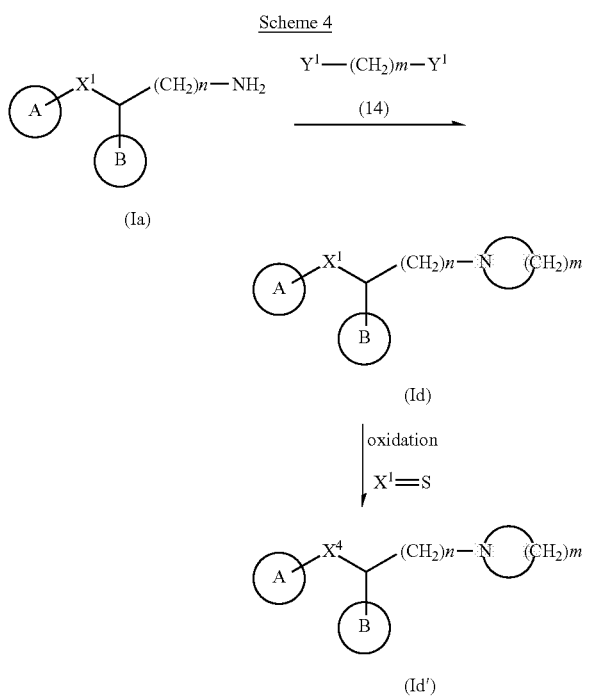

wherein $Y^1$ is a halogen atom, m is an integer of 2 to 7, and the other symbols are as defined above.

Compound (Id) can be produced by reacting compound (Ia) with compound (14) in the presence of a base, in an inert solvent.

The amount of compound (14) to be used is generally 1 to 10 equivalent, preferably 1 to 2 equivalent, relative to compound (Ia).

Examples of the base include inorganic bases such as sodium hydroxide, potassium hydroxide, lithium hydroxide, barium hydroxide, sodium carbonate, potassium carbonate, cesium carbonate, sodium hydrogencarbonate, potassium hydrogencarbonate and the like; and organic bases such as triethylamine, diisopropylethylamine, N-methylmorpholine, DBU (1,8-diazabicyclo[5.4.0]undec-7-ene), DBN (1,5-diazabicyclo[4.3.0]non-5-ene), pyridine, 2,6-lutidine and the like. The amount of the base to be used is generally 2 to 20 equivalent, preferably 2 to 4 equivalent, relative to compound (Ia).

Examples of the inert solvent include ether solvents such as tetrahydrofuran (THF), diethyl ether, diisopropyl ether, tert-butyl methyl ether, 1,4-dioxane, 1,2-dimethoxyethane and the like; nitrile solvents such as acetonitrile and the like, and the like.

The reaction temperature is generally 0° C. to 50° C., preferably 0° C. to 25° C.

The reaction time is generally 30 min to 24 hr, preferably 30 min to 2 hr.

Compound (Id') can be produced by subjecting compound (Id) wherein $X^1$ is S to oxidation. The reaction can be carried out in the same manner as in the production of compound (Ia') from compound (Ia) in Reaction Scheme 1.

Compound (Ie), which is compound (I) wherein X is O, S or $NR^3$ wherein $R^3$ is as defined above and the $CH_2$ in —$(CH_2)$n- is replaced by O, S, S(O), $S(O)_2$ or $NR^4$ wherein $R^4$ is as defined above, and compound (Ie'), which is compound (I) wherein X is S(O) or $S(O)_2$ and the $CH_2$ in —$(CH_2)$n- is replaced by O, S, S(O), $S(O)_2$ or $NR^4$ wherein $R^4$ is as defined above, can be produced according to the method shown in Reaction Scheme 5.

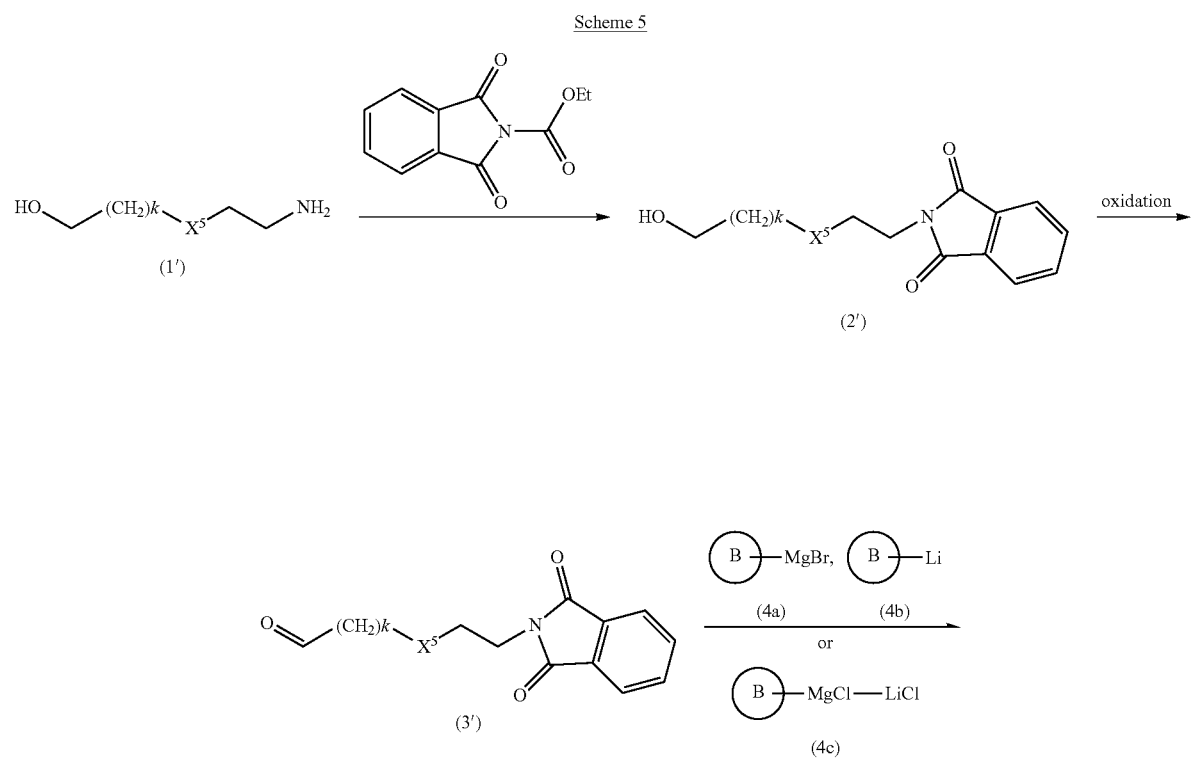

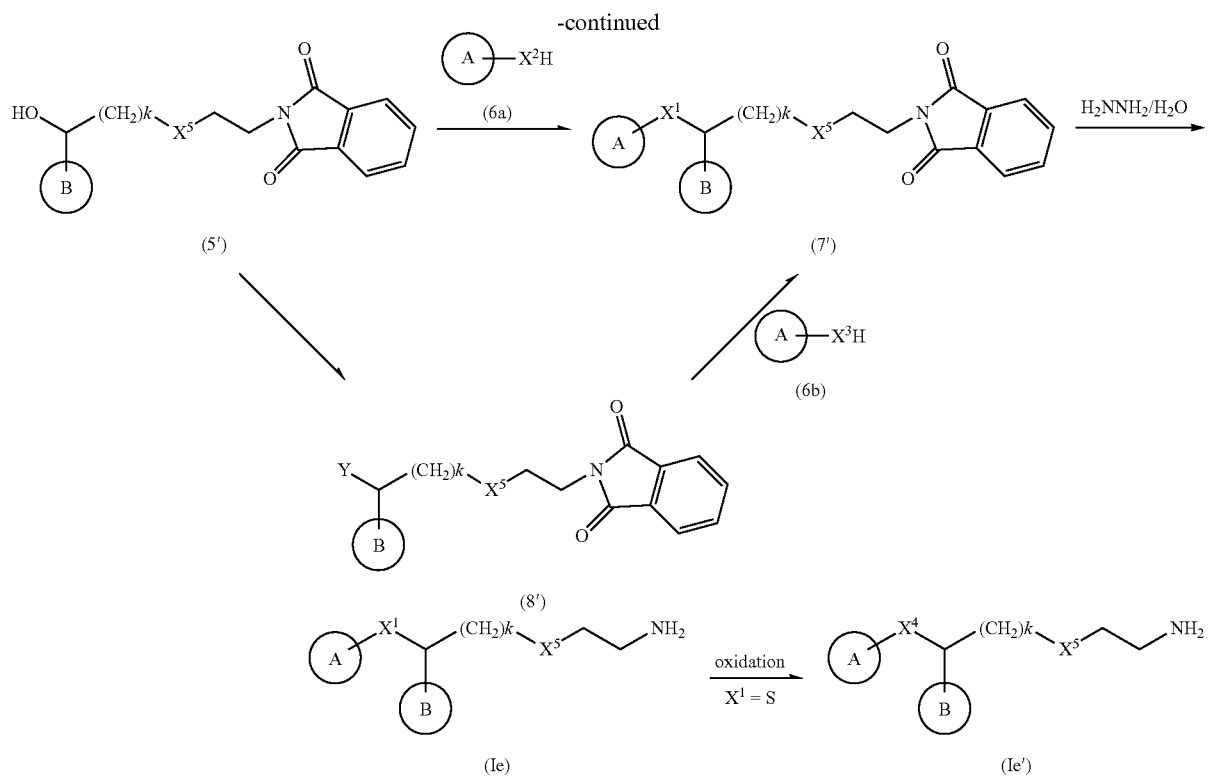

wherein $X^5$ is O, S, S(O), S(O)$_2$ or NR$^4$ wherein R$^4$ is as defined above, k is an integer of 1 to 3, and the other symbols are as defined above.

Compound (2') can be produced by reacting compound (1') with ethyl 1,3-dioxoisoindole-2-carboxylate in the presence of a base, in an inert solvent. The reaction can be carried out in the same manner as in the production of compound (2) from compound (1) and ethyl 1,3-dioxoisoindole-2-carboxylate in Reaction Scheme 1.

Compound (3') can be produced by subjecting compound (2') to oxidation. The reaction can be carried out in the same manner as in the production of compound (3) from compound (2) in Reaction Scheme 1.

Compound (5') can be produced by reacting compound (3') with compound (4a), compound (4b) or compound (4c) in an inert solvent. The reaction can be carried out in the same manner as in the production of compound (5) from compound (3) and compound (4a), compound (4b) or compound (4c) in Reaction Scheme 1.

Compound (7') wherein $X^1$ is O or S can be produced by reacting compound (5') with compound (6a) in the presence of an azodicarboxylic acid diester and triphenylphosphine, in an inert solvent. The reaction can be carried out in the same manner as in the production of compound (7) from compound (5) and compound (6a) in Reaction Scheme 1.

Compound (7') wherein $X^1$ is NR$^3$ wherein R$^3$ is as defined above can be produced by converting compound (5') to compound (8') by halogenation, and then reacting compound (8') with compound (6b) in the presence of a base, in an inert solvent. The reaction can be carried out in the same manner as in the production of compound (7) by the conversion of compound (5) to compound (8) followed by the reaction with compound (6b).

Compound (Ie) can be produced by reacting compound (7') with hydrazine in an inert solvent. The reaction can be carried out in the same manner as in the production of compound (Ia) from compound (7) and hydrazine in Reaction Scheme 1.

Compound (Ie') can be produced by subjecting compound (Ie) wherein $X^1$ is S to oxidation. The reaction can be carried out in the same manner as in the production of compound (Ia') from compound (Ia) in Reaction Scheme 1.

Compound (Ie') wherein $X^5$ is S(O) or S(O)$_2$ can also be produced by subjecting compound (Ie) wherein $X^1$ and $X^5$ are S to oxidation. The reaction can be carried out in the same manner as in the production of compound (Ia') from compound (Ia) in Reaction Scheme 1.

Compound (1), compound (1'), compound (4a), compound (4b), compound (4c), compound (6a), compound (6b), compound (9) and compound (14) which are raw material compounds, may be a commercially available product, or can also be produced according to a method known per se.

Optically active compound (If) and (If'), which are compound (I) wherein X is O or S and R$^1$ and R$^2$ are both hydrogen atoms, and optically active compound (If'') and (If'''), which are compound (I) wherein X is S(O) or S(O)$_2$ and R$^1$ and R$^2$ are both hydrogen atoms, can be produced according to the method shown in Reaction Scheme 6.

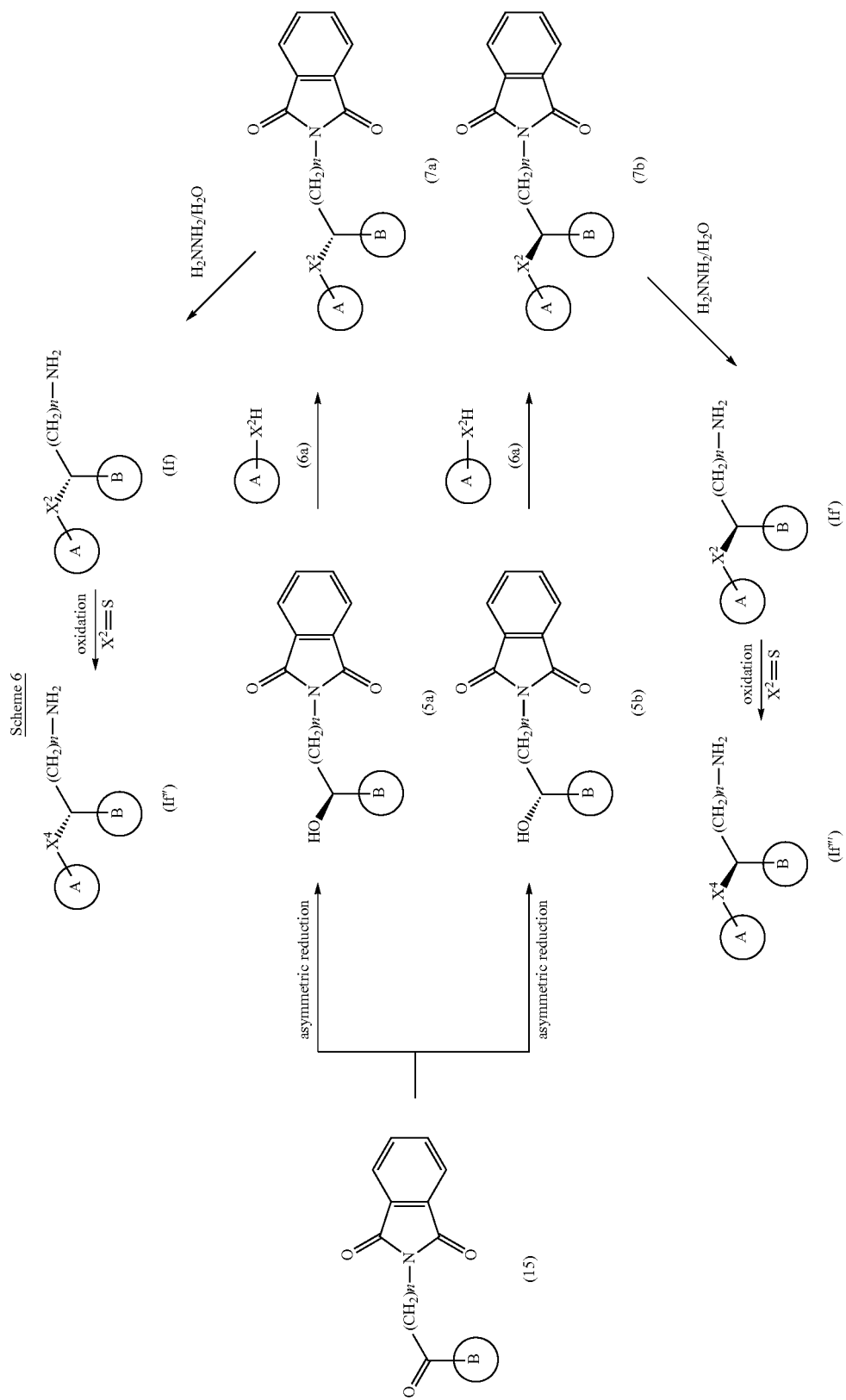

wherein each symbol is as defined above.

Compound (5a) or compound (5b) can be produced by subjecting compound (15) to an asymmetric reduction reaction, respectively.

The asymmetric reduction reaction is carried out by reducing compound (15) with an asymmetric reducing agent in an inert solvent according to a method known per se, or by reducing compound (15) with a hydrogenating agent in the presence of an asymmetric catalyst.

Examples of the asymmetric reducing agent for compound (5a) include (−)-B-chlorodiisopinocampheylborane ((−)-IPC$_2$BCl)

Examples of the asymmetric reducing agent for compound (5b) include (+)-B-chlorodiisopinocampheylborane ((+)-IPC$_2$BCl)

Compound (If) or compound (If') can be produced by reacting compound (7a) or compound (7b) with hydrazine in an inert solvent, respectively. The reaction can be carried out in the same manner as in the production of compound (Ia) from compound (7) in Reaction Scheme 1.

Compound (If") or compound (If'") can be produced by subjecting compound (If) or compound (If') wherein $X^2$ is S to oxidation, respectively. The reaction can be carried out in the same manner as in the production of compound (Ia') from compound (Ia) in Reaction Scheme 1.

Compound (15) which is a raw material compound may be a commercially available product, or can also be produced according to a method known per se.

Compound (5a) and compound (5b) can also be produced according to the method shown in Reaction Scheme 7.

Scheme 7

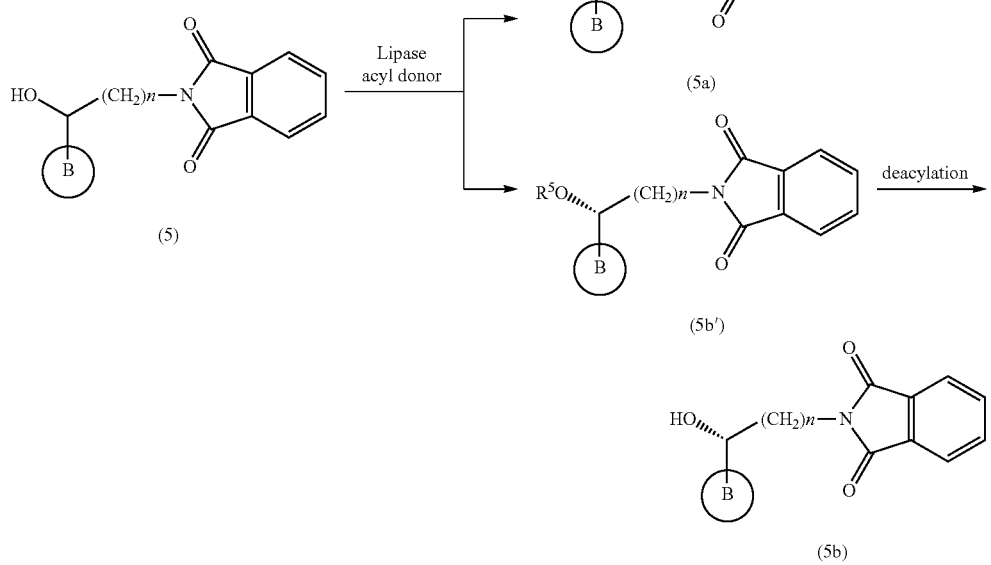

wherein $R^5$ is an alkanoyl group derived from acyl donor, and the other symbols are as defined above.

Compound (5a) and compound (5b') can be produced by reacting compound (5) with an acyl donor (e.g., vinyl acetate, etc.) in the presence of a suitable lipase (e.g., lipase PS "Amano" (Amano Enzyme Inc., etc.), in an inert solvent.

The amount of the acyl donor to be used is generally 2 to 10 equivalent, preferably 5 to 8 equivalent, relative to compound (5).

Examples of the inert solvent include ether solvents such as tetrahydrofuran (THF), diethyl ether, diisopropyl ether, tert-butyl methyl ether, 1,4-dioxane, 1,2-dimethoxyethane and the like, and the like.

The reaction temperature is generally 20° C. to 50° C., preferably 30° C. to 40° C.

The reaction time is generally 36 hr to 120 hr, preferably 72 hr to 96 hr.

The amount of the asymmetric reducing agent to be used is generally 2 to 5 equivalent, preferably 2 to 3 equivalent, relative to compound (15).

Examples of the inert solvent include ether solvents such as tetrahydrofuran (THF), diethyl ether, diisopropyl ether, tert-butyl methyl ether, 1,4-dioxane, 1,2-dimethoxyethane and the like; hydrocarbon solvents such as pentane, hexane, heptane and the like, and mixed solvents thereof.

The reaction temperature is generally 0° C. to room temperature, preferably 0° C. to 10° C.

The reaction time is generally 60 min to 24 hr, preferably 60 min to 3 hr.

Compound (7a) or compound (7b) can be produced by reacting compound (5a) or compound (5b) with compound (6a) in the presence of an azodicarboxylic acid diester and triphenylphosphine, in an inert solvent, respectively. The reaction can be carried out in the same manner as in the production of compound (7) from compound (5) in Reaction Scheme 1.

Compound (5b) can be produced by subjecting compound (5b') to deacylation in the presence of a base, in an inert solvent.

Examples of the base include inorganic bases such as sodium hydroxide, potassium hydroxide, lithium hydroxide, barium hydroxide, sodium carbonate, potassium carbonate, cesium carbonate, sodium hydrogencarbonate, potassium hydrogencarbonate and the like. The amount of the base to be used is generally 1 to 5 equivalent, preferably 1 to 3 equivalent, relative to compound (5b').

Examples of the inert solvent include alcohol solvents such as methanol, ethanol, propanol, 2-propanol, butanol, isobutanol, tert-butanol and the like; water and the like.

The reaction temperature is generally 0° C. to 50° C., preferably 0° C. to 30° C.

The reaction time is generally 30 min to 24 hr, preferably 60 min to 5 hr.

In each reaction of the synthesis of the objective compound and raw material compound, when the raw material compound has an amino group, a carboxyl group or a hydroxy group as a substituent, a protecting group generally used in peptide chemistry and the like may be introduced into these substituents. By removing the protecting group as necessary after the reaction, the objective compound can be obtained.

Examples of the protecting group include those described in "Protective Groups in Organic Synthesis, 3rd Edition", Wiley-Interscience, 1999, Theodora W. Greene, Peter G. M. Wuts.

Examples of the amino-protecting group include a formyl group, a $C_{1-6}$ alkyl-carbonyl group (e.g., acetyl, propionyl groups etc.), a phenylcarbonyl group, a $C_{1-6}$ alkyl-oxycarbonyl group (e.g., methoxycarbonyl, ethoxycarbonyl groups etc.), an aryloxycarbonyl group (e.g., a phenyloxycarbonyl group etc.), a $C_{7-10}$ aralkyl-carbonyl group (e.g., a benzyloxycarbonyl group etc.), a benzyl group, a benzhydryl group, a trityl group, a phthaloyl group and the like, each of which optionally has substituent(s). Examples of the substituent include a halogen atom (e.g., fluorine, chlorine, bromine, iodine atoms etc.), a $C_{1-6}$ alkyl-carbonyl group (e.g., acetyl, propionyl, butylcarbonyl groups etc.), a nitro group and the like, and the number of the substituents is about 1 to 3.

Examples of the carboxyl-protecting group include a $C_{1-6}$ alkyl group (e.g., methyl, ethyl, n-propyl, isopropyl, n-butyl, tert-butyl groups etc.), a phenyl group, a trityl group, a silyl group and the like, each of which optionally has substituent(s). Examples of the substituent include a halogen atom (e.g., fluorine, chlorine, bromine, iodine atoms etc.), a formyl group, a $C_{1-6}$ alkyl-carbonyl group (e.g., acetyl, propionyl, butylcarbonyl groups etc.), a nitro group and the like, and the number of the substituents is about 1 to 3.

Examples of the hydroxy-protecting group include a $C_{1-6}$ alkyl group (e.g., methyl, ethyl, n-propyl, isopropyl, n-butyl, tert-butyl groups etc.), a phenyl group, a $C_{7-10}$ aralkyl group (e.g., a benzyl group etc.), a formyl group, a $C_{1-6}$ alkyl-carbonyl group (e.g., acetyl, propionyl groups etc.), an aryloxycarbonyl group (e.g., a phenyloxycarbonyl group etc.), a $C_{7-10}$ aralkyl-carbonyl group (e.g., a benzyloxycarbonyl group etc.), a pyranyl group, a furanyl group, a silyl group and the like, each of which optionally has substituent(s). Examples of the substituent include a halogen atom (e.g., fluorine, chlorine, bromine, iodine atoms etc.), a $C_{1-6}$ alkyl group, a phenyl group, a $C_{7-10}$ aralkyl group, a nitro group and the like, and the number of the substituents is about 1 to 4.

These protecting groups can be removed according to a method known per se or the method described in "Protective Groups in Organic Synthesis, 3rd Edition", Wiley-Interscience, 1999, Theodora W. Greene, Peter G. M. Wuts or the like, or method analogous thereto. Specifically, a method by treating with acid, base, reduction, ultraviolet rays, hydrazine, phenylhydrazine, sodium N-methyldithiocarbamate, tetrabutylammonium fluoride, palladium acetate and the like can be employed.

In the above-mentioned method, when compound (I) is obtained in a free form, it may be converted to a salt with an inorganic acid (hydrochloric acid, sulfuric acid, hydrobromic acid etc.), an organic acid (methanesulfonic acid, benzenesulfonic acid, toluenesulfonic acid, oxalic acid, fumaric acid, maleic acid, tartaric acid etc.), an inorganic base (alkali metals such as sodium, potassium and the like; alkaline-earth metals such as calcium, magnesium and the like, aluminium, ammonium etc.) or an organic base (trimethylamine, triethylamine, pyridine, picoline, ethanolamine, diethanolamine, triethanolamine, dicyclohexyl amine, N,N'-dibenzylethylenediamine etc.) and the like, according to a conventional method. When compound (I) is obtained as a salt, it may also be converted to a free form or other salt according to a conventional method.

In the above-mentioned each reaction, when the raw material compound can be in the form of a salt, the compound can be used as a salt. Examples of the salt include those similar to the salt of compound (I).

Compound (I) of the present invention obtained by the above-mentioned method can be isolated and purified according to a conventional separation means (e.g., recrystallization, distillation, chromatography etc.).

When compound (I) has an optical isomer, a stereoisomer, a positional isomer or a rotamer, these are also encompassed in compound (I), and can be obtained as a single product according to synthetic method and separation method known per se (concentration, solvent extraction, column chromatography, recrystallization etc.). For example, when compound (I) has an optical isomer, each optical isomer resolved from compound (I) is encompassed in compound (I).

The optical isomer can be produced according to a method known per se. Specifically, the optical isomer can be obtained by using an optically active synthetic intermediate, or by subjecting the racemic final product to optical resolution according to a conventional method.

Compound (I) may be a crystal, and the crystal form may be single or a mixture of crystal forms, both of which are encompassed in compound (I). The crystal can be produced according to a crystallization method known per se.

Compound (I) may be a hydrate, a non-hydrate, a solvate or a non-solvate.

Since the present invention compound shows low toxicity, and can be used directly or in the form of a pharmaceutical composition by mixing with a pharmacologically acceptable carrier and the like, as an agent for the prophylaxis or treatment of various diseases mentioned below in a mammal (e.g., human, mouse, rat, rabbit, dog, cat, cow, horse, pig, monkey).

Examples of the pharmacologically acceptable carrier include various organic or inorganic carrier substances conventionally used as preparation materials, which are added as excipient, lubricant, binder or disintegrant for solid preparations; as solvent, solubilizing agent, suspending agent, isotonicity agent, buffer or soothing agent for liquid preparation, and the like. Where necessary, preparation additives such as preservative, antioxidant, colorant, sweetener and the like can also be used.

Preferable examples of the excipient include lactose, sucrose, D-mannitol, D-sorbitol, starch, pregelatinized starch, dextrin, microcrystalline cellulose, low-substituted hydroxypropyl cellulose, sodium carboxymethylcellulose, gum arabic, pullulan, light anhydrous silicic acid, synthetic aluminum silicate and magnesium aluminate metasilicate.

Preferable examples of the lubricant include magnesium stearate, calcium stearate, talc and colloidal silica.

Preferable examples of the binder include pregelatinized starch, sucrose, gelatin, gum arabic, methylcellulose, carboxymethylcellulose, sodium carboxymethylcellulose, microcrystalline cellulose, sucrose, D-mannitol, trehalose, dextrin, pullulan, hydroxypropyl cellulose, hydroxypropyl methylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropyl cellulose.

Preferable examples of the solvent include water for injection, physiological saline, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, laurylaminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethyl cellulose, hydroxyethyl cellulose, hydroxypropyl cellulose; polysorbates and polyoxyethylene hydrogenated castor oils.

Preferable examples of the isotonicity agent include sodium chloride, glycerol, D-mannitol, D-sorbitol and glucose.

Preferable examples of the buffer include buffers such as phosphates, acetates, carbonates, citrates and the like.

Preferable examples of the soothing agent include benzyl alcohol.

Preferable examples of the preservative include p-hydroxybenzoates, chlorobutanol, benzyl alcohol, phenethyl alcohol, dehydroacetic acid and sorbic acid.

Preferable examples of the antioxidant include sulfites and ascorbic acid.

Preferable examples of the colorant include water-soluble edible tar pigments (e.g., Food Color Red Nos. 2 and 3, Food Color Yellow Nos. 4 and 5, Food Color Blue Nos. 1 and 2), water insoluble lake pigments (e.g., aluminum salts of the above-mentioned water-soluble edible tar pigment) and natural pigments (e.g., β-carotene, chlorophyll, red iron oxide).

Preferable examples of the sweetening agent include saccharin sodium, dipotassium glycyrrhizinate, aspartame and stevia.

Examples of the dosage form of the pharmaceutical composition include oral preparations such as tablet (including sugar-coated tablet, film-coated tablet, sublingual tablet, orally disintegrating tablet), capsules (including soft capsule, microcapsule), granule, powder, troche, syrup, emulsion, suspension, films (e.g., orally disintegrable films) and the like; and parenteral agents such as injection (e.g., subcutaneous injection, intravenous injection, intramuscular injection, intraperitoneal injection, drip infusion), external preparations (e.g., dermal preparation, ointment), suppository (e.g., rectal suppository, vaginal suppository), pellet, nasal preparation, pulmonary preparation (inhalant), eye drop and the like.

These can be respectively safely administered orally or parenterally (e.g., topically, rectally, intravenously administered).

These preparations may be a release control preparation (e.g., sustained-release microcapsule) such as an immediate-release preparation, a sustained-release preparation and the like.

The pharmaceutical composition can be produced according to a method conventionally used in the field of pharmaceutical formulation, for example, the method described in the Japanese Pharmacopoeia, and the like.

While the content of the compound of the present invention in the pharmaceutical composition varies depending on the dosage form, dose of the compound of the present invention and the like, it is, for example, about 0.1 to 100 wt %.

During production of an oral preparation, coating may be applied as necessary for the purpose of masking of taste, enteric property or durability.

Examples of the coating base to be used for coating include sugar coating base, water-soluble film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the water-soluble film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, iron sesquioxide and the like can be used.

The compound of the present invention shows low toxicity (e.g., acute toxicity, chronic toxicity, genetic toxicity, reproductive toxicity, cardiotoxicity, carcinogenicity) and a few side effects. Therefore, it can be used as an agent for the prophylaxis or treatment or a diagnostic of various diseases in a mammal (e.g., human, bovine, horse, dog, cat, monkey, mouse, rat).

Since the present invention compound has an excellent LAT-1 inhibitory activity, it is useful as an agent for the prophylaxis or treatment of cancer wherein LAT-1 is expressed in tumor cell, for example, pancreatic cancer, lung cancer, colorectal cancer, breast cancer, prostate cancer, brain tumor, stomach cancer, esophageal cancer, liver cancer, skin cancer, choriocarcinoma, renal cancer, head and neck cancer, tongue cancer, metastatic cancer or invasive cancer, particularly pancreatic cancer or lung cancer.

The dose of the compound of the present invention varies depending on the administration subject, route of administration, target disease, symptoms, etc. For example, when it is administered orally to an adult patient, its dose is about 0.01 to 100 mg/kg body weight per dose, preferably 0.05 to 30 mg/kg body weight per dose, more preferably 0.1 to 10 mg/kg body weight per dose, which is desirably administered once to 3 times a day.

EXAMPLES

The present invention is explained in detail in the following by referring to Reference examples, Examples, Formulation Examples and Experimental Examples, which are merely exemplified and not to be construed as limitative, and the invention may be changed within the scope of the present invention.

Example 1: Synthesis of 5-phenyl-5-[4-(trifluoromethyl)phenoxy]pentan-1-amine (1) Synthesis of 2-(5-hydroxypentyl)isoindole-1,3-dione 5-Aminopentan-1-ol (1.8 g) was dissolved in tetrahydrofuran (17 ml), potassium carbonate (1.1 g) and ethyl 1,3-dioxoisoindole-2-carboxylate (3.9 g) were added thereto under ice-cooling, and the mixture was stirred at room temperature for 10 min. To the reaction solution was added water, and the mixture was extracted with ethyl acetate. The organic layer was washed with saturated brine, and dried over anhydrous sodium sulfate. The solution was filtered, and the filtrate was concentrated under reduced pressure to give the title compound (5.0 g) as a colorless liquid.

$^1$H-NMR (400 MHz, CDCl$_3$) δ:7.82-7.87 (m, 2H), 7.69-7.73 (m, 2H), 3.71 (t, J=7.2 Hz, 2H), 3.65 (t, J=6.4 Hz, 2H), 1.59-1.66 (m, 2H), 1.42-1.47 (m, 2H)

(2) Synthesis of 5-(1,3-dioxoisoindol-2-yl)pentanal 2-(5-Hydroxypentyl)isoindole-1,3-dione (5.0 g) was dissolved in methylene chloride (17 ml), dimethyl sulfoxide (2.6 g), triethylamine (3.4 g) and pyridine-sulfur trioxide complex (4.2 g) were added thereto under ice-cooling, and the mixture was stirred at the same temperature for 50 min. The organic layer was washed successively with water and saturated brine, and dried over anhydrous sodium sulfate. The solution was filtered, and the filtrate was concentrated under reduced pressure to give the title compound (4.1 g) as a pale-orange liquid.

$^1$H-NMR (400 MHz, CDCl$_3$) δ:9.77 (s, 1H), 7.82-7.86 (m, 2H), 7.70-7.73 (m, 2H), 3.72 (t, J=6.8 Hz, 2H), 2.49-2.53 (m, 2H), 1.68-1.73 (m, 4H), 1.42-1.47 (m, 2H).

(3) Synthesis of 2-(5-hydroxy-5-phenylpentyl)isoindole-1,3-dione 5-(1,3-Dioxoisoindol-2-yl)pentanal (4.1 g) was dissolved in tetrahydrofuran (35 ml), 2.0M phenylmagnesium bromide-tetrahydrofuran solution (8.5 ml) was added dropwise thereto under ice-cooling, and the mixture was stirred at the same temperature for 10 min. To the reaction solution was added saturated aqueous ammonium chloride solution, and the mixture was extracted with ethyl acetate. The organic layer was washed with saturated brine, and dried over anhydrous sodium sulfate. The solution was filtered, and the filtrate was concentrated under reduced pressure. The obtained residue was purified by silica gel column chromatography (hexane:ethyl acetate=2:1) to give the title compound (1.8 g, yield of three steps: 34.1%) as a colorless liquid.

$^1$H-NMR (400 MHz, CDCl$_3$) δ:7.81-7.84 (m, 2H), 7.69-7.73 (m, 2H), 7.31-7.34 (m, 4H), 7.24-7.27 (m, 1H), 4.65-4.69 (m, 1H), 3.67 (t, J=7.2 Hz, 2H), 1.69-1.83 (m, 4H), 1.45-1.56 (m, 1H), 1.32-1.42 (m, 1H).

(4) Synthesis of 2-(5-phenyl-5-[4-(trifluoromethyl)phenoxy]pentyl)isoindole-1,3-dione 2-(5-Hydroxy-5-phenylpentyl)isoindole-1,3-dione (184 mg) was dissolved in tetrahydrofuran (6 ml), 4-(trifluoromethyl)phenol (176 mg), triphenylphosphine (290 mg) and 2.2M diethyl azadicarboxylate-toluene solution (510 μl) were added thereto under ice-cooling, and the mixture was stirred at the same temperature for 1 hr. The reaction solution was concentrated under reduced pressure, and the obtained residue was purified by silica gel column chromatography (hexane:ethyl acetate=10:1) to give the title compound (193 mg, yield: 71.6%) as a colorless liquid.

$^1$H-NMR (400 MHz, CDCl$_3$) δ:7.82-7.84 (m, 2H), 7.70-7.73 (m, 2H), 7.40 (d, J=8.4 Hz, 2H), 7.28-7.33 (m, 4H), 7.23-7.27 (m, 1H), 6.86 (d, J=8.8 Hz, 2H), 5.12 (dd, J=8.0, 5.2 Hz, 1H), 3.68 (t, J=7.2 Hz, 2H), 2.02-2.11 (m, 1H), 1.85-1.95 (m, 1H), 1.70-1.76 (m, 2H), 1.56-1.63 (m, 1H), 1.43-1.51 (m, 1H).

(5) Synthesis of 5-phenyl-5-[4-(trifluoromethyl)phenoxy]pentan-1-amine 2-(5-Phenyl-5-[4-(trifluoromethyl)phenoxy]pentyl)isoindole-1,3-dione (193 mg) was dissolved in ethanol (4 ml), hydrazine monohydrate (29 μl) was added thereto, and the mixture was stirred at 90° C. for 2 hr. The reaction solution was concentrated under reduced pressure, the solid was removed by filtration, and the obtained residue was purified by preparative chromatography (acetonitrile (0.05% TFA): water (0.05% TFA)=1:9 to 9:1). The main fractions were collected, saturated aqueous sodium hydrogencarbonate solution was added thereto, and the mixture was extracted with diethyl ether. The organic layer was washed with saturated brine, and dried over anhydrous sodium sulfate. The solution was filtered, the filtrate was concentrated under reduced pressure, and the residue was dried to give the title compound (76 mg, yield: 55.5%) as a pale-yellow liquid.

$^1$H-NMR (400 MHz, CDCl$_3$) δ:7.42 (d, J=8.8 Hz, 2H), 7.29-7.35 (m, 4H), 7.24-7.28 (m, 1H), 6.88 (d, J=8.8 Hz, 2H), 5.13 (dd, J=8.0, 5.2 Hz, 1H), 2.72 (t, J=7.2 Hz, 2H), 1.98-2.06 (m, 1H), 1.82-1.88 (m, 1H), 1.52-1.59 (m, 3H), 1.41-1.48 (m, 1H).

MS(ESI) m/z: 324.4 [MH$^+$], C$_{18}$H$_{20}$OF$_3$NO requires 323.35.

Example 2: Synthesis of 5-phenyl-5-[4-(trifluoromethyl)phenoxy]pentan-1-amine fumarate 5-Phenyl-5-[4-(trifluoromethyl)phenoxy]pentan-1-amine (30 mg) was dissolved in ethyl acetate (4 ml), and an ethanol solution (1 ml) of fumaric acid (11 mg) was added thereto. The mixture was stirred at room temperature for 30 min, and the resulting crystals were collected by filtration, washed with ethyl acetate, and dried under reduced pressure to give the title compound (23 mg, yield: 54.9%) as a white solid.

$^1$H-NMR (400 MHz, DMSO-$d_6$) δ:7.55 (d, J=8.8 Hz, 2H), 7.39-7.42 (m, 2H), 7.33-7.36 (m, 2H), 7.24-7.28 (m, 1H), 7.06 (d, J=8.4 Hz, 2H), 6.42 (s, 2H), 5.43 (dd, J=7.6, 5.2 Hz, 1H), 2.75 (t, J=7.2 Hz, 2H), 1.92-1.97 (m, 1H), 1.77-1.83 (m, 1H), 1.56-1.63 (m, 2H), 1.47-1.53 (m, 1H), 1.35-1.41 (m, 1H).

Example 3: Synthesis of 5-phenyl-5-[2-chloro-4-(trifluoromethyl)phenoxy]pentan-1-amine (1) Synthesis of 2-(5-phenyl-5-[2-chloro-4-(trifluoromethyl)phenoxy]pentyl)isoindole-1,3-dione The title compound (227 mg, yield: 81.1%) was obtained as a colorless liquid by using 2-(5-hydroxy-5-phenylpentyl)isoindole-1,3-dione (177 mg), 2-chloro-4-(trifluoromethyl)phenol (224 mg), triphenylphosphine (301 mg) and 2.2M diethyl azadicarboxylate-toluene solution (525 μl) in the same manner as in Step (4) of Example 1.

$^1$H-NMR (400 MHz, CDCl$_3$) δ:7.82-7.84 (m, 2H), 7.70-7.73 (m, 2H), 7.55 (d, J=1.6 Hz, 1H), 7.29-7.35 (m, 4H), 7.24-7.28 (m, 1H), 6.74 (d, J=8.8 Hz, 2H), 5.18 (dd, J=8.0, 4.8 Hz, 1H), 3.69 (t, J=7.2 Hz, 2H), 2.10-2.20 (m, 1H), 1.89-1.98 (m, 1H), 1.72-1.77 (m, 2H), 1.47-1.69 (m, 2H).

(2) Synthesis of 5-phenyl-5-[2-chloro-4-(trifluoromethyl)phenoxy]pentan-1-amine

The title compound (15 mg, yield: 8.7%) was obtained as a yellow liquid by using 2-(5-phenyl-5-[2-chloro-4-(trifluoromethyl)phenoxy]pentyl)isoindole-1,3-dione (227 mg) and hydrazine monohydrate (31.8 al) in the same manner as in Step (5) of Example 1.

$^1$H-NMR (400 MHz, CDCl$_3$) δ:7.60 (d, J=2.0 Hz, 1H), 7.33-7.36 (m, 4H), 7.26-7.29 (m, 2H), 6.75 (d, J=8.8 Hz, 1H), 5.19 (dd, J=8.0, 4.8 Hz, 1H), 2.74 (t, J=6.8 Hz, 2H), 2.07-2.13 (m, 1H), 1.87-1.94 (m, 1H), 1.50-1.64 (m, 4H).

MS(ESI) m/z: 358.3 [MH$^+$], $C_{18}H_{19}ClF_3NO$ requires 357.11.

Example 4: Synthesis of N-methyl-5-phenyl-5-[4-(trifluoromethyl)phenoxy]pentan-1-amine (1) Synthesis of tert-butyl N-methyl-N-(5-oxopentyl)carbamate The title compound (310 mg) was obtained as a yellow liquid by using tert-butyl N-methyl-N-(5-hydroxypentyl)carbamate (294.9 mg), dimethyl sulfoxide (308 mg), triethylamine (399 mg) and pyridine-sulfur trioxide complex (625 mg) in the same manner as in Step (2) of Example 1.

(2) Synthesis of tert-butyl N-methyl-N-(5-phenyl-5-hydroxypentyl) carbamate

The title compound (171 mg, yield of two steps: 42.8%) was obtained as a yellow liquid by using tert-butyl N-methyl-N-(5-oxopentyl)carbamate (310 mg) and 2.0M phenylmagnesium bromide-tetrahydrofuran solution (6.8 ml) in the same manner as in Step (3) of Example 1.

$^1$H-NMR (400 MHz, CDCl$_3$) δ:7.33-7.35 (m, 4H), 7.26-7.29 (m, 1H), 4.65-4.69 (m, 1H), 3.12-3.28 (m, 2H), 2.81 (s, 3H), 1.80-1.85 (m, 2H), 1.48-1.56 (m, 2H), 1.44 (s, 9H), 1.35-1.48 (m, 2H).

(3) Synthesis of tert-butyl N-methyl-N-(5-phenyl-5-[4-(trifluoromethyl)phenoxy]pentyl)carbamate The title compound (210 mg, yield: 82.8%) was obtained as a pale-yellow liquid by using tert-butyl N-methyl-N-(5-phenyl-5-hydroxypentyl)carbamate (171 mg), 4-(trifluoromethyl)phenol (300 mg), triphenylphosphine (473 mg) and 2.2M diethyl azadicarboxylate-toluene solution (842 μl) in the same manner as in Step (4) of Example 1.

$^1$H-NMR (400 MHz, CDCl$_3$) δ:7.42 (d, J=8.8 Hz, 2H), 7.32-7.35 (m, 4H), 7.26-7.29 (m, 1H), 6.88 (d, J=8.4 Hz, 2H), 5.12 (dd, J=8.0, 4.8 Hz, 1H), 3.10-3.18 (m, 2H), 2.81 (s, 3H), 2.00-2.10 (m, 1H), 1.82-1.88 (m, 1H), 1.43 (s, 9H), 1.35-1.58 (m, 4H).

(4) Synthesis of N-methyl-5-phenyl-5-[4-(trifluoromethyl)phenoxy]pentan-1-amine tert-Butyl N-methyl-N-(5-phenyl-5-[4-(trifluoromethyl)phenoxy]pentyl)carbamate (210 mg) was ice-cooled, 4N hydrogen chloride-ethyl acetate solution (4.8 ml) was added thereto, and the mixture was stirred at the same temperature for 2 hr. To the reaction solution saturated was added aqueous sodium hydrogencarbonate solution, and the mixture was extracted with ethyl acetate. The organic layer was washed with saturated brine, and dried over anhydrous sodium sulfate. The solution was filtered, and the filtrate was concentrated under reduced pressure. The obtained residue was purified by preparative chromatography (acetonitrile (0.05% TFA):water (0.05% TFA)=1:9 to 9:1). The main fractions were collected, saturated aqueous sodium hydrogencarbonate solution was added thereto, and the mixture was extracted with diethyl ether. The organic layer was washed with saturated brine, and dried over anhydrous sodium sulfate. The solution was filtered, the filtrate was concentrated under reduced pressure, and the residue was dried to give the title compound (45 mg, yield: 27.9%) as a pale-brown liquid.

$^1$H-NMR (400 MHz, CDCl$_3$) δ:7.42 (d, J=8.4 Hz, 2H), 7.30-7.35 (m, 4H), 7.24-7.28 (m, 1H), 6.88 (d, J=8.8 Hz, 2H), 5.13 (dd, J=8.0, 4.8 Hz, 1H), 2.60 (t, J=6.4 Hz, 2H), 2.43 (s, 3H), 2.02-2.05 (m, 1H), 1.84-1.88 (m, 1H), 1.43-1.58 (m, 4H).

MS(ESI) m/z: 338.3 [MH$^+$], $C_{19}H_{22}F_3NO$ requires 337.17.

Example 5: Synthesis of N,N-dimethyl-5-phenyl-5-[4-(trifluoromethyl)phenoxy]pentan-1-amine To N-Methyl-5-phenyl-5-[4-(trifluoromethyl)phenoxy]pentan-1-amine (23 mg) were added 37% aqueous formaldehyde solution (1 ml) and formic acid (499 mg), and the mixture was stirred at 70° C. for 2 days. To the reaction solution was added water, and the mixture was washed with diethyl ether. To the aqueous layer was added saturated aqueous sodium hydrogencarbonate solution, and the mixture was extracted with diethyl ether. The organic layer was washed with saturated brine, and dried over anhydrous sodium sulfate. The solution was filtered, the filtrate was concentrated under reduced pressure, and the residue was dried to give the title compound (13 mg, yield: 51.9%) as a yellow liquid.

$^1$H-NMR (400 MHz, CDCl$_3$) δ:7.42 (d, J=8.8 Hz, 2H), 7.31-7.34 (m, 4H), 7.24-7.28 (m, 1H), 6.88 (d, J=8.4 Hz, 2H), 5.12 (dd, J=8.0, 5.2 Hz, 1H), 2.23 (t, J=7.2 Hz, 2H), 2.20 (s, 6H), 1.99-2.06 (m, 1H), 1.82-1.88 (m, 1H), 1.36-1.55 (m, 4H).
MS(ESI) m/z: 352.3 [MH$^+$], C$_{20}$H$_{24}$F$_3$NO requires 351.18.

Example 6: Synthesis of 6-phenyl-6-[4-(trifluoromethyl)phenoxy]hexan-1-amine (1) Synthesis of tert-butyl N-(6-oxohexyl)carbamate The title compound (4.7 g) was obtained as a yellow liquid by using tert-butyl N-(6-hydroxyhexyl)carbamate (3.2 g), dimethyl sulfoxide (3.4 g), triethylamine (4.4 g) and pyridine-sulfur trioxide complex (7.0 g) in the same manner as in Step (2) of Example 1.

(2) Synthesis of tert-butyl N-(6-phenyl-6-hydroxyhexyl)carbamate

The title compound (1.9 g, yield of two steps: 45.1%) was obtained as a yellow liquid by using tert-butyl N-(6-oxohexyl)carbamate (4.7 g) and 2.0M phenylmagnesium bromide-tetrahydrofuran solution (73 ml) in the same manner as in Step (3) of Example 1.
$^1$H-NMR (400 MHz, CDCl$_3$) δ:7.34-7.35 (m, 4H), 7.26-7.29 (m, 1H), 4.62-4.69 (m, 1H), 4.49 (s, 1H), 3.08-3.15 (m, 2H), 1.78-1.83 (m, 1H), 1.67-1.76 (m, 1H), 1.45-1.50 (m, 4H), 1.44 (s, 9H), 1.33-1.35 (m, 2H).

(3) Synthesis of tert-butyl N-(6-phenyl-6-[4-(trifluoromethyl)phenoxy]hexyl)carbamate The title compound (313 mg, yield: 76.9%) was obtained as a pale-yellow liquid by using tert-butyl N-(6-phenyl-6-hydroxyhexyl)carbamate (273 mg), 4-(trifluoromethyl)phenol (250 mg), triphenylphosphine (407 mg) and 2.2M diethyl azadicarboxylate-toluene solution (719 μl) in the same manner as in Step (4) of Example 1.
$^1$H-NMR (400 MHz, CDCl$_3$) δ:7.42 (d, J=8.8 Hz, 2H), 7.29-7.35 (m, 4H), 7.26-7.29 (m, 1H), 6.88 (d, J=8.8 Hz, 2H), 5.11 (dd, J=8.0, 5.2 Hz, 1H), 4.49 (s, 1H), 3.04-3.18 (m, 2H), 1.96-2.06 (m, 1H), 1.38-1.88 (m, 1H), 1.43 (s, 9H), 1.38-1.61 (m, 6H).

(4) Synthesis of 6-phenyl-6-[4-(trifluoromethyl)phenoxy]hexan-1-amine

The title compound (69 mg, yield: 40.7%) was obtained as a pale-yellow liquid by using tert-butyl N-(6-phenyl-6-[4-(trifluoromethyl)phenoxy]hexyl)carbamate (210 mg) and 4N hydrogen chloride-ethyl acetate solution (4.8 ml) in the same manner as in Step (4) of Example 4.
$^1$H-NMR (400 MHz, CDCl$_3$) δ:7.42 (d, J=8.4 Hz, 2H), 7.33-7.35 (m, 4H), 7.24-7.32 (m, 1H), 6.88 (d, J=8.4 Hz, 2H), 5.12 (dd, J=7.6, 5.2 Hz, 1H), 2.67 (t, J=6.8 Hz, 2H), 1.97-2.05 (m, 1H), 1.81-1.87 (m, 1H), 1.34-1.51 (m, 6H).
MS(ESI) m/z: 338.3 [MH$^+$], C$_{19}$H$_{22}$F$_3$NO requires 337.17.

Example 7: Synthesis of 6-phenyl-6-[2-chloro-4-(trifluoromethyl)phenoxy]hexan-1-amine (1) Synthesis of tert-butyl N-(6-phenyl-6-[2-chloro-4-(trifluoromethyl)phenoxy]hexyl)carbamate The title compound (606 mg, yield: 73.9%) was obtained as a pale-yellow liquid by using tert-butyl N-(6-phenyl-6-hydroxyhexyl)carbamate (510 mg), 2-chloro-4-(trifluoromethyl)phenol (660 mg), triphenylphosphine (860 mg) and 2.2M diethyl azadicarboxylate-toluene solution (1.5 ml) in the same manner as in Step (4) of Example 1.
$^1$H-NMR (400 MHz, CDCl$_3$) δ:7.60 (d, J=2.0 Hz, 1H), 7.31-7.36 (m, 4H), 7.25-7.29 (m, 2H), 6.75 (d, J=8.4 Hz, 1H), 5.18 (dd, J=7.6, 5.2 Hz, 1H), 4.49 (s, 1H), 3.08-3.12 (m, 2H), 2.04-2.16 (m, 1H), 1.85-1.92 (m, 1H), 1.44 (s, 9H), 1.33-1.61 (m, 6H).

(2) Synthesis of 6-phenyl-6-[2-chloro-4-(trifluoromethyl)phenoxy]hexan-1-amine

The title compound (87 mg, yield: 37.0%) was obtained as a pale-yellow liquid by using tert-butyl N-(6-phenyl-6-[2-chloro-4-(trifluoromethyl)phenoxy]hexyl)carbamate (300 mg) and 4N hydrogen chloride-ethyl acetate solution (3.2 ml) in the same manner as in Step (4) of Example 4.
$^1$H-NMR (400 MHz, CDCl$_3$) δ:7.60 (d, J=1.6 Hz, 1H), 7.31-7.37 (m, 4H), 7.25-7.29 (m, 2H), 6.76 (d, J=8.8 Hz, 1H), 5.18 (dd, J=7.6, 5.2 Hz, 1H), 2.69 (t, J=6.8 Hz, 2H), 2.07-2.71 (m, 1H), 1.87-1.93 (m, 1H), 1.36-1.63 (m, 6H).
MS(ESI) m/z: 372.3 [MH$^+$], C$_{19}$H$_{21}$ClF$_3$NO requires 371.13.

Example 8: Synthesis of N,N-dimethyl-6-phenyl-6-[4-(trifluoromethyl)phenoxy]hexan-1-amine The title compound (8 mg, yield: 17.7%) was obtained as a pale-yellow liquid by using 6-phenyl-6-[4-(trifluoromethyl)phenoxy]hexan-1-amine (40 mg), 37% aqueous formaldehyde solution (2 ml) and formic acid (1100 mg) in the same manner as in Example 5.
$^1$H-NMR (400 MHz, CDCl$_3$) δ:7.42 (d, J=8.8 Hz, 2H), 7.30-7.35 (m, 4H), 7.24-7.28 (m, 1H), 6.88 (d, J=8.4 Hz, 2H), 5.12 (dd, J=8.0, 5.2 Hz, 1H), 2.24 (t, J=7.2 Hz, 2H), 2.21 (s, 6H), 1.99-2.03 (m, 1H), 1.81-1.87 (m, 1H), 1.23-1.51 (m, 6H).
MS(ESI) m/z: 366.3 [MH$^+$], C$_{21}$H$_{26}$F$_3$NO requires 365.2.

Example 9: Synthesis of N-methyl-6-phenyl-6-[4-(trifluoromethyl)phenoxy]hexan-1-amine (1) Synthesis of tert-butyl N-methyl-N-(6-phenyl-6-[4-(trifluoromethyl)phenoxy]hexyl)carbamate tert-Butyl N-(6-phenyl-6-[4-(trifluoromethyl)phenoxy]hexyl)carbamate (104 mg) was dissolved in tetrahydrofuran (4.7 ml), 60% sodium hydride (27 mg) was added thereto under ice-cooling, and the mixture was stirred at room temperature for 30 min. Methyl iodide (168 mg) was added thereto under ice-cooling, and the mixture was stirred overnight at room temperature. To the reaction solution was added water, and the mixture was extracted with ethyl acetate. The organic layer was washed with saturated brine, and dried over anhydrous sodium sulfate. The solution was filtered, and the filtrate was concentrated under reduced pressure. The obtained residue was purified by silica gel column chromatography (hexane:ethyl acetate=10:1) to give the title compound (64 mg, yield: 59.8%) as a colorless liquid.
$^1$H-NMR (400 MHz, CDCl$_3$) δ:7.42 (d, J=8.4 Hz, 2H), 7.30-7.35 (m, 4H), 7.24-7.28 (m, 1H), 6.88 (d, J=8.8 Hz, 2H), 5.11 (dd, J=7.6, 4.8 Hz, 1H), 3.15-3.23 (m, 2H), 2.81 (s, 3H), 1.99-2.03 (m, 1H), 1.79-1.88 (m, 1H), 1.44 (s, 9H), 1.33-1.54 (m, 6H).

(2) Synthesis of N-methyl-6-phenyl-6-[4-(trifluoromethyl)phenoxy]hexan-1-amine The title compound (19 mg, yield: 38.5%) was obtained as a pale-yellow liquid by using tert-butyl N-methyl-N-(6-phenyl-6-[4-(trifluoromethyl)phenoxy]hexyl)carbamate (64 mg) and 4N hydrogen chloride-ethyl acetate solution (1.4 ml) in the same manner as in Step (4) of Example 4.

$^1$H-NMR (400 MHz, CDCl$_3$) δ:7.43 (d, J=8.4 Hz, 2H), 7.30-7.35 (m, 4H), 7.24-7.28 (m, 1H), 6.88 (d, J=8.4 Hz, 2H), 5.12 (dd, J=7.6, 4.8 Hz, 1H), 2.57 (t, J=6.8 Hz, 2H), 2.43 (s, 3H), 1.99-2.03 (m, 1H), 1.81-1.87 (m, 1H), 1.33-1.54 (m, 6H).

MS(ESI) m/z: 352.3 [MH$^+$], C$_{20}$H$_{24}$F$_3$NO requires 351.18.

Examples 10 to 47

The compounds of Examples 10 to 47 were obtained in the same manner as in Example 1.

Example 48: Synthesis of 5-(thiophen-2-yl)-5-[4-(trifluoromethyl)phenoxy]pentan-1-amine

(1) Synthesis of 2-[5-hydroxy-5-(thiophen-2-yl)pentyl]-isoindole-1,3-dione 5-(1,3-Dioxoisoindol-2-yl)pentane (13.7 g) synthesized in Step (2) of Example 1 was dissolved in tetrahydrofuran (160 ml), 1.0M 2-thienyllithium-tetrahydrofuran solution (14 ml) was added dropwise thereto under ice-cooling, and the mixture was stirred at the same temperature for 10 min. To the reaction solution was added saturated aqueous ammonium chloride solution, and the mixture was extracted with ethyl acetate. The organic layer was washed with saturated brine, and dried over anhydrous sodium sulfate. The solution was filtered, and the filtrate was concentrated under reduced pressure. The obtained residue was purified by silica gel column chromatography (hexane:ethyl acetate=2:1) to give the title compound (0.9 g).

(2) Synthesis of 5-(thiophen-2-yl)-5-[4-(trifluoromethyl)phenoxy]pentan-1-amine The title compound (70 mg) was obtained by using 2-[5-hydroxy-5-(thiophen-2-yl)pentyl]-isoindole-1,3-dione (185 mg) in the same manner as in Steps (4) and (5) of Example 1.

Examples 49 to 54

The compounds of Examples 49 to 54 were obtained in the same manner as in Example 48.

Example 55: Synthesis of 5-(furan-2-yl)-5-[4-(trifluoromethyl)phenoxy]pentan-1-amine

(1) Synthesis of 2-[5-hydroxy-5-(furan-2-yl)pentyl]-isoindole-1,3-dione

Furan (420 mg) was dissolved in tetrahydrofuran (4 ml), and the mixture was cooled to −78° C. 1.6M n-Butyllithium-hexane solution (2.6 ml) was added dropwise thereto, and the mixture was stirred at the same temperature for 30 min. To the reaction solution was added dropwise a tetrahydrofuran solution (8 ml) of 5-(1,3-dioxoisoindol-2-yl)pentanal (1.1 g) synthesized in Step (2) of Example 1, and the mixture was stirred for 5 min. To the reaction solution was added water, and the mixture was extracted with ethyl acetate. The organic layer was washed with saturated brine, and dried over anhydrous sodium sulfate. The solution was filtered, and the filtrate was concentrated under reduced pressure. The obtained residue was purified by silica gel column chromatography (hexane:ethyl acetate=3:1) to give the title compound (135 mg).

(2) Synthesis of 5-(furan-2-yl)-5-[4-(trifluoromethyl)phenoxy]pentan-1-amine The title compound (22 mg) was obtained by using 2-[5-hydroxy-5-(furan-2-yl)pentyl]-isoindole-1,3-dione (135 mg) in the same manner as in Steps (4) and (5) of Example 1.

Example 56: Synthesis of 5-(1,3-thiazol-2-yl)-5-[4-(trifluoromethyl)phenoxy]pentan-1-amine

(1) Synthesis of 2-[5-hydroxy-5-(1,3-thiazol-2-yl)pentyl]-isoindole-1,3-dione 2-Bromothiazole (213 mg) was dissolved in tetrahydrofuran (15 ml), 1.3M isopropylmagnesium chloride-lithium chloride complex-tetrahydrofuran solution (2 ml) was added thereto under ice-cooling, and the mixture was stirred for 10 min. A solution of 5-(1,3-dioxoisoindol-2-yl)pentanal (330 mg) synthesized in Step (2) of Example 1 in tetrahydrofuran (2 ml) was added dropwise thereto, and the mixture was stirred at the same temperature for 1.5 hr. To the reaction solution was added saturated aqueous ammonium chloride solution, and the mixture was extracted with ethyl acetate. The organic layer was washed with saturated brine, and dried over anhydrous sodium sulfate. The solution was filtered, and the filtrate was concentrated under reduced pressure. The obtained residue was purified by silica gel column chromatography (hexane:ethyl acetate=2:1) to give the title compound (196 mg).

(2) Synthesis of 5-(1,3-thiazol-2-yl)-5-[4-(trifluoromethyl)phenoxy]pentan-1-amine The title compound (13 mg) was obtained by using 2-[5-hydroxy-5-(1,3-thiazol-2-yl)pentyl]-isoindole-1,3-dione (196 mg) in the same manner as in Steps (4) and (5) of Example 1.

Example 57: Synthesis of 5-(1,3-oxazol-2-yl)-5-[4-(trifluoromethyl)phenoxy]pentan-1-amine The compound of Example 57 was obtained in the same manner as in Example 56.

Example 58: Synthesis of 5-phenyl-5-{[4-(trifluoromethyl)phenyl]sulfanyl}pentan-1-amine

(1) Synthesis of 2-(5-phenyl-5-{[4-(trifluoromethyl)phenyl]sulfanyl}pentyl)isoindole-1,3-dione 2-(5-Hydroxy-5-phenylpentyl)isoindole-1,3-dione (1.1 g) synthesized in Step (3) of Example 1 was dissolved in tetrahydrofuran (35 ml), 4-(trifluoromethyl)thiophenol (1.1 g), triphenylphosphine (1.5 g) and 2.2M diethyl azadicarboxylate-toluene solution (2.7 ml) were added thereto under ice-cooling, and the mixture was stirred at the same temperature for 1 hr, and then overnight at room temperature.

The reaction solution was concentrated under reduced pressure, and the obtained residue was purified by silica gel column chromatography (hexane:ethyl acetate=10:1) to give the title compound (636 mg).

(2) Synthesis of 5-phenyl-5-{[4-(trifluoromethyl)phenyl]sulfanyl}pentan-1-amine

The title compound (41 mg) was obtained by using 2-(5-phenyl-5-{[4-(trifluoromethyl)phenyl]sulfanyl}pentyl)isoindole-1,3-dione (228 mg) in the same manner as in Step (5) of Example 1.

Example 59: Synthesis of 5-phenyl-5-{[4-(trifluoromethyl)phenyl]sulfonyl}pentan-1-amine 5-Phenyl-5-{[4-(trifluoromethyl)phenyl]sulfanyl}pentan-1-amine (84 mg) was dissolved in dichloromethane (2.5 ml), m-chloroperbenzoic acid (193 mg) was added thereto under ice-cooling, and the mixture was stirred at the same temperature for 1 hr. The reaction solution was concentrated under reduced pressure, and the obtained residue was purified by preparative chromatography (acetonitrile (0.05% TFA):water (0.05% TFA)=1:9 to 9:1). The main fractions were collected, saturated aqueous sodium hydrogencarbonate solution was added thereto, and the mixture was extracted with diethyl ether. The organic layer was washed with saturated brine, and dried over anhydrous sodium sulfate. The solution was filtered, the filtrate was concentrated under reduced pressure, and the residue was dried to give the title compound (24 mg).

Example 60: Synthesis of 5-phenyl-5-{[4-(trifluoromethyl)phenyl]sulfinyl}pentan-1-amine 5-Phenyl-5-{[4-(trifluoromethyl)phenyl]sulfanyl}pentan-1-amine) (85 mg) was dissolved in methanol (10 ml), sodium periodate (320 mg) was added thereto under ice-cooling, and the mixture was stirred at room temperature for 1 hr. The reaction solution was concentrated under reduced pressure, and the obtained residue was purified by preparative chromatography (acetonitrile (0.05% TFA):water (0.05% TFA)=1:9 to 9:1). The main fractions were collected, saturated aqueous sodium hydrogencarbonate solution was added thereto, and the mixture was extracted with diethyl ether. The organic layer was washed with saturated brine, and dried over anhydrous sodium sulfate. The solution was filtered, the filtrate was concentrated under reduced pressure, and the residue was dried to give the title compound (20 mg).

Example 61: Synthesis of 5-phenyl-5-{[4-(trifluoromethyl)phenyl]amino}pentan-1-amine (1) Synthesis of 2-(5-bromo-5-phenylpentyl)isoindole-1,3-dione 2-(5-Hydroxy-5-phenylpentyl)isoindole-1,3-dione (2.2 g) synthesized in Step (3) of Example 1 was dissolved in tetrahydrofuran (70 ml), carbon tetrabromide (5.1 g) and triphenylphosphine (4.1 g) were added thereto, and the mixture was stirred at room temperature for 20 min. The reaction solution was concentrated under reduced pressure, and the obtained residue was purified by silica gel column chromatography (hexane:ethyl acetate=5:1) to give the title compound (2.2 g).

(2) Synthesis of 2-(5-phenyl-5-{[4-(trifluoromethyl)phenyl]amino}pentyl)isoindole-1,3-dione 2-(5-Bromo-5-phenylpentyl)isoindole-1,3-dione (1.2 g) was dissolved in 1,3-dimethyl-2-imidazolidinone (30 ml), 4-(trifluoromethyl)aniline (1.1 g) was added thereto, and the mixture was stirred at 100° C. for 3 hr. The reaction solution was allowed to be cooled, water was added thereto, and the mixture was extracted with ethyl acetate. The organic layer was washed with saturated brine, and dried over anhydrous sodium sulfate. The solution was filtered, and the filtrate was concentrated under reduced pressure. The obtained residue was purified by silica gel column chromatography (hexane:ethyl acetate=5:1) to give the title compound (397 mg).

(3) Synthesis of 5-phenyl-5-{[4-(trifluoromethyl)phenyl]amino}pentan-1-amine

The title compound (18 mg) was obtained by using 2-(5-phenyl-5-{[4-(trifluoromethyl)phenyl]amino}pentyl)isoindole-1,3-dione (397 mg) in the same manner as in Step (5) of Example 1.

Example 62: Synthesis of 2-({2-phenyl-2-[4-(trifluoromethyl)phenoxy]ethyl}sulfanyl)ethanamine (1) Synthesis of 2-{2-[(2-hydroxyethyl)sulfanyl]ethyl}isoindole-1,3-dione The title compound (13.9 g) was obtained as a yellow liquid by using 2-[(2-aminoethyl)sulfanyl]ethanol (5.3 g), potassium carbonate (3.0 g) and ethyl 1,3-dioxoisoindole-2-carboxylate (9.6 g) in the same manner as in Step (1) of Example 1.

(2) Synthesis of {[2-(1,3-dioxo-1,3-dihydroisoindol-2-yl)ethyl]sulfanyl}acetaldehyde The title compound (7.5 g) was obtained as a white solid by using 2-{2-[(2-hydroxyethyl)sulfanyl]ethyl}isoindole-1,3-dione (13.9 g), dimethyl sulfoxide (6.8 g), triethylamine (8.8 g) and pyridine-sulfur trioxide complex (10.4 g) in the same manner as in Step (2) of Example 1.

(3) Synthesis of 2-{2-[(2-hydroxy-2-phenylethyl)sulfanyl]ethyl}isoindole-1,3-dione The title compound (405 mg) was obtained as a pale-yellow liquid by using {[2-(1,3-dioxo-1,3-dihydroisoindol-2-yl)ethyl]sulfanyl}acetaldehyde (974 mg) and 2.0M phenylmagnesium bromide-tetrahydrofuran solution (2.0 ml) in the same manner as in Step (3) of Example 1.

(4) Synthesis of 2-[2-({2-phenyl-2-[4-(trifluoromethyl)phenoxy]ethyl}sulfanyl)ethyl]isoindole-1,3-dione The title compound (199 mg) was obtained as a pale-yellow liquid by using 2-{2-[(2-hydroxy-2-phenylethyl)sulfanyl]ethyl}isoindole-1,3-dione (405 mg), 4-(trifluoromethyl)phenol (305 mg), triphenylphosphine (462 mg) and 2.2M diethyl azadicarboxylate-toluene solution (844 µl) in the same manner as in Step (4) of Example 1.

(5) Synthesis of 2-({2-phenyl-2-[4-(trifluoromethyl)phenoxy]ethyl}sulfanyl)ethanamine The title compound (21 mg) was obtained as a colorless liquid by using 2-[2-({2-phenyl-2-[4-(trifluoromethyl) phenoxy]ethyl}sulfanyl)ethyl]isoindole-1,3-dione (199 mg) and hydrazine monohydrate (26 µl) in the same manner as in Step (5) of Example 1.

Example 63: Synthesis of 2-{2-phenyl-2-[4-(trifluoromethyl)phenoxy]ethoxy}ethanamine (1) Synthesis of 2-[2-(2-hydroxyethoxy)ethyl]isoindole-1,3-dione The title compound (8.0 g) was obtained by using 2-(2-aminoethoxy)ethanol (5.0 g), potassium carbonate (3.3 g) and ethyl 1,3-dioxoisoindole-2-carboxylate (10.4 g) in the same manner as in Step (1) of Example 1.

(2) Synthesis of [2-(1,3-dioxo-1,3-dihydroisoindol-2-yl)ethoxy]acetaldehyde

The title compound (1.8 g) was obtained by using 2-[2-(2-hydroxyethoxy)ethyl]isoindole-1,3-dione (3.0 g), dimethyl sulfoxide (2.0 g), triethylamine (2.5 g) and pyridine-sulfur trioxide complex (3.3 g) in the same manner as in Step (2) of Example 1.

(3) Synthesis of 2-[2-(2-hydroxy-2-phenylethoxy)ethyl]isoindole-1,3-dione

The title compound (694 mg) was obtained by using [2-(1,3-dioxo-1,3-dihydroisoindol-2-yl)ethoxy]acetaldehyde (1.8 g) and 2.0M phenylmagnesium bromide-tetrahydrofuran solution (3.9 ml) in the same manner as in Step (3) of Example 1.

(4) Synthesis of 2-(2-{2-phenyl-2-[4-(trifluoromethyl)phenoxy]ethoxy}ethyl)isoindole-1,3-dione The title compound (284 mg) was obtained by using 2-[2-(2-hydroxy-2-phenylethoxy)ethyl]isoindole-1,3-dione (267 mg), 4-(trifluoromethyl)phenol (253 mg), triphenylphosphine (369 mg) and 2.2M diethyl azadicarboxylate-toluene solution (675 µl) in the same manner as in Step (4) of Example 1.

(5) Synthesis of 2-{2-phenyl-2-[4-(trifluoromethyl)phenoxy]ethoxy}ethanamine

The title compound (144 mg) was obtained by using 2-(2-{2-phenyl-2-[4-(trifluoromethyl)phenoxy]ethoxy}ethyl)isoindole-1,3-dione (279 mg) and hydrazine monohydrate (56 µl) in the same manner as in Step (5) of Example 1.

Example 64: Synthesis of 1-{5-phenyl-5-[4-(trifluoromethyl)phenoxy]pentyl}piperidine 5-Phenyl-5-[4-(trifluoromethyl)phenoxy]pentan-1-amine (349 mg) synthesized in Example 1 was dissolved in acetonitrile (22 ml), diisopropylethylamine (292 mg) and 1,5-dibromopentane (173 mg) were added thereto, and the mixture was stirred overnight at 70° C. The reaction solution was concentrated under reduced pressure, and the obtained residue was purified by silica gel column chromatography (hexane:ethyl acetate=10:1) to give the title compound (138 mg).

Example 65: Synthesis of 1-{5-phenyl-5-[4-(trifluoromethyl)phenoxy]pentyl}pyrrolidine 5-Phenyl-5-[4-(trifluoromethyl)phenoxy]pentan-1-amine (295 mg) synthesized in Example 1 was dissolved in acetonitrile (20 ml), diisopropylethylamine (248 mg) and 1,4-dibromobutane (138 mg) were added thereto, and the mixture was stirred overnight at 70° C. The reaction solution was concentrated under reduced pressure, and the obtained residue was purified by silica gel column chromatography (hexane:ethyl acetate=10:1) to give the title compound (68 mg).

Example 66: Synthesis of (R)-5-phenyl-5-[4-(trifluoromethyl)phenoxy]pentan-1-amine fumarate (1) Synthesis of (S)-2-(5-hydroxy-5-phenylpentyl)isoindole-1,3-dione and (R)-2-(5-acetoxy-5-phenylpentyl)isoindole-1,3-dione 2-(5-Hydroxy-5-phenylpentyl)isoindole-1,3-dione (2.2 g) obtained in Step (3) of Example 1 was dissolved in diisopropyl ether (70 ml), vinyl acetate (3.95 ml) and lipase PS-IM (Amano, 2.2 g) were added thereto, and the mixture was stirred at room temperature for 2 days, and then at 35° C. for 3 days. The reaction solution was filtered, and the obtained residue was purified by silica gel column chromatography (hexane:ethyl acetate=3:1 to 1:1) to give (S)-2-(5-hydroxy-5-phenylpentyl)isoindole-1,3-dione (0.9 g) as a white solid and (R)-2-(5-acetoxy-5-phenylpentyl)isoindole-1,3-dione (1.5 g) as a colorless liquid, respectively.

(Optical Purity Measurement)

The optical purity was confirmed as follows. (S)-2-(5-Hydroxy-5-phenylpentyl)isoindole-1,3-dione was reacted with acetic anhydride in pyridine to give (S)-2-(5-acetoxy-5-phenylpentyl)isoindole-1,3-dione, and the optical purity of this compound was confirmed by analyzing using chiral column under the following analysis condition.

<Result of Analysis>
(R)-2-(5-acetoxy-5-phenylpentyl)isoindole-1,3-dione optical purity: 93% ee, retention time: 12.0 min
(S)-2-(5-acetoxy-5-phenylpentyl)isoindole-1,3-dione optical purity: 93% ee, retention time: 15.2 min <Chiral Column Analysis Condition>
column: Chiralcel (registered trademark) OJ-H (Daicel, 4.6×150 mm)
measurement wavelength: 230 nm
flow rate: 1.0 ml/min
temperature: 40° C.
mobile phase: n-hexane/IPA=8/2

(2) Synthesis of (R)-2-(5-phenyl-5-[4-(trifluoromethyl)phenoxy]pentyl)isoindole-1,3-dione (S)-2-(5-Hydroxy-5-phenylpentyl) isoindole-1,3-dione (480.5 mg) was dissolved in tetrahydrofuran (15 ml), 4-(trifluoromethyl)phenol (392.2 mg) and triphenylphosphine (618.8 mg) were added thereto under ice-cooling, and the mixture was stirred. 2.2M Diethyl azodicarboxylate-toluene solution (1.1 ml) was added dropwise thereto, and the mixture was stirred at room temperature for 1 hr. The reaction solution was concentrated under reduced pressure, and the obtained residue was purified by silica gel column chromatography (hexane:ethyl acetate=8:1) to give the title compound (573.0 mg) as a colorless liquid $^1$H NMR (400 MHz, CDCl$_3$): δ: 7.83-7.84 (m, 2H), 7.70-7.72 (m, 2H), 7.40 (d, J=8.4 Hz, 2H), 7.23-7.33 (m, 5H), 6.86 (d, J=8.4 Hz, 2H), 5.12 (dd, J=8.0, 5.2 Hz, 1H), 3.68 (t, J=7.6 Hz, 2H), 2.01-2.10 (m, 1H), 1.85-1.94 (m, 1H), 1.70-1.76 (m, 2H), 1.43-1.66 (m, 2H).

(3) Synthesis of (R)-5-phenyl-5-[4-(trifluoromethyl) phenoxy]pentan-1-amine (R)-2-(5-Phenyl-5-[4-(trifluoromethyl)phenoxy]pentyl) isoindole-1,3-dione (563.0 mg) was dissolved in ethanol (12 ml), hydrazine monohydrate (154.0 µl) was added thereto, and the mixture was stirred at 90° C. for 3.5 hr. The solid was removed by filtration, the filtrate was concentrated under reduced pressure, and the obtained residue was purified by silica gel column chromatography (hexane:ethyl acetate=3:1→hexane:ethyl acetate:methanol=3:1:0.1) to give the title compound (354.7 mg) as a colorless liquid.

$^1$H NMR (400 MHz, CDCl$_3$): δ: 7.42 (d, J=8.8 Hz, 2H), 7.26-7.35 (m, 5H), 6.88 (d, J=8.8 Hz, 2H), 5.12 (dd, J=8.0, 5.2 Hz, 1H), 2.76 (t, J=7.6 Hz, 2H), 1.99-2.07 (m, 1H), 1.82-1.89 (m, 1H), 1.54-1.60 (m, 3H), 1.42-1.50 (m, 1H).

MS(ESI) m/z: 324.1 [MH$^+$], C18H20F3NO requires 323.35.

(4) Synthesis of (R)-5-phenyl-5-[4-(trifluoromethyl) phenoxy]pentan-1-amine fumarate (R)-5-Phenyl-5-[4-(trifluoromethyl)phenoxy]pentan-1-amine (354.7 mg) was dissolved in ethanol (10 ml), fumaric acid (115.8 mg) was added thereto, and the mixture was stirred at room temperature for 15 min. The reaction solution was filtered, and the filtrate was concentrated under reduced pressure. To the obtained residue was added ethyl acetate (10 ml), and the mixture was stirred at room temperature for 10 min. The solid was collected by filtration, washed with ethyl acetate, and dried under reduced pressure to give the title compound (273.3 mg) as a white solid.

$^1$H NMR (400 MHz, DMSO-d$_6$): δ: 7.55 (d, J=8.8 Hz, 2H), 7.33-7.41 (m, 4H), 7.24-7.28 (m, 1H), 7.06 (d, J=8.4 Hz, 2H), 6.42 (s, 2H), 5.43 (dd, J=7.6, 5.2 Hz, 1H), 2.75 (t, J=7.2 Hz, 2H), 1.91-1.96 (m, 1H), 1.76-1.85 (m, 1H), 1.56-1.63 (m, 2H), 1.46-1.53 (m, 1H), 1.34-1.42 (m, 1H).

MS(ESI) m/z: 324.4 [MH+], C18H20F3NO requires 323.35.

Example 67: Synthesis of (S)-5-phenyl-5-[4-(trifluoromethyl)phenoxy]pentan-1-amine fumarate

(1) Synthesis of (R)-2-(5-hydroxy-5-phenylpentyl) isoindole-1,3-dione (R)-2-(5-Acetoxy-5-phenylpentyl)isoindole-1,3-dione (1.5 g) obtained in Step (1) of Example 66 was dissolved in methanol (40 ml), potassium carbonate (1.2 g) was added thereto under ice-cooling, and the mixture was stirred at room temperature for 4 hr. To the reaction solution was added water, and the mixture was extracted with ethyl acetate. The organic layer was washed with saturated brine, and dried over anhydrous sodium sulfate. The solution was filtered, and the filtrate was concentrated under reduced pressure to give the title compound (1.2 g) as a white solid.

$^1$H NMR (400 MHz, CDCl$_3$): δ: 7.83-7.84 (m, 2H), 7.70-7.71 (m, 2H), 7.26-7.33 (m, 5H), 4.66-4.69 (m, 1H), 3.67 (t, J=6.8 Hz, 2H), 1.68-1.84 (m, 4H), 1.45-1.53 (m, 1H), 1.32-1.45 (m, 1H).

(2) Synthesis of (S)-2-(5-phenyl-5-[4-(trifluoromethyl)phenoxy]pentyl)isoindole-1,3-dione (R)-2-(5-Hydroxy-5-phenylpentyl)isoindole-1,3-dione (300.1 mg) was dissolved in tetrahydrofuran (10 ml), 4-(trifluoromethyl)phenol (240.5 mg) and triphenylphosphine (385.9 mg) were added thereto under ice-cooling, and the mixture was stirred. 2.2M Diethyl azodicarboxylate-toluene solution (682 µl) was added dropwise thereto, and the mixture was stirred at room temperature for 2 hr. The reaction solution was concentrated under reduced pressure, and the obtained residue was purified by silica gel column chromatography (hexane:ethyl acetate=8:1) to give the title compound (396.5 mg) as a colorless liquid.

$^1$H NMR (400 MHz, CDCl$_3$): δ: 7.81-7.84 (m, 2H), 7.69-7.73 (m, 2H), 7.40 (d, J=8.8 Hz, 2H), 7.23-7.31 (m, 5H), 6.86 (d, J=8.8 Hz, 2H), 5.12 (dd, J=8.0, 4.8 Hz, 1H), 3.68 (t, J=7.6 Hz, 2H), 2.03-2.09 (m, 1H), 1.85-1.94 (m, 1H), 1.70-1.76 (m, 2H), 1.54-1.63 (m, 1H), 1.43-1.53 (m, 1H).

(3) Synthesis of (S)-5-phenyl-5-[4-(trifluoromethyl) phenoxy]pentan-1-amine (S)-2-(5-Phenyl-5-[4-(trifluoromethyl)phenoxy]pentyl) isoindole-1,3-dione (382.7 mg) was dissolved in ethanol (8.5 ml), hydrazine monohydrate (104.8 µl) was added thereto, and the mixture was stirred at 90° C. for 2.5 hr. The solid was removed by filtration, the filtrate was concentrated under reduced pressure, and the obtained residue was purified by silica gel column chromatography (hexane:ethyl acetate=3:1→hexane:ethyl acetate:methanol=3:1:0.1) to give the title compound (237.1 mg) as a colorless liquid.

$^1$H NMR (400 MHz, CDCl$_3$): δ: 7.42 (d, J=8.8 Hz, 2H), 7.24-7.35 (m, 5H), 6.88 (d, J=8.8 Hz, 2H), 5.12 (dd, J=8.0, 5.2 Hz, 1H), 2.74 (t, J=7.2 Hz, 2H), 1.99-2.06 (m, 1H), 1.82-1.89 (m, 1H), 1.53-1.56 (m, 3H), 1.45-1.50 (m, 1H).

MS(ESI) m/z: 324.1 [MH$^+$], C18H20F3NO requires 323.35.

(4) Synthesis of (S)-5-phenyl-5-[4-(trifluoromethyl) phenoxy]pentan-1-amine fumarate (S)-5-Phenyl-5-[4-(trifluoromethyl)phenoxy]pentan-1-amine (237.1 mg) was dissolved in ethanol (7 ml), fumaric acid (79.8 mg) was added thereto, and the mixture was stirred at room temperature for 15 min. The reaction solution was filtered, and the filtrate was concentrated under reduced pressure. To the obtained residue was added ethyl acetate (5 ml), and the mixture was stirred at room temperature for 10 min. The solid was collected by filtration, washed with ethyl acetate, and dried under reduced pressure to give the title compound (163.5 mg) as a white solid.

$^1$H NMR (400 MHz, DMSO-d$_6$): δ: 7.55 (d, J=8.8 Hz, 2H), 7.33-7.41 (m, 4H), 7.24-7.28 (m, 1H), 7.06 (d, J=8.4 Hz, 2H), 6.39 (s, 2H), 5.43 (dd, J=8.0, 5.6 Hz, 1H), 2.75 (t, J=6.8 Hz, 2H), 1.91-1.96 (m, 1H), 1.78-1.85 (m, 1H), 1.46-1.62 (m, 3H), 1.34-1.42 (m, 1H).

MS(ESI) m/z: 324.1 [MH+], C18H20F3NO requires 323.35.

Example 68: Synthesis of (R)-5-[3-fluoro-4-(trifluoromethyl)phenoxy]-5-phenylpentan-1-amine fumarate The compound of Example 68 was obtained by using (S)-2-(5-hydroxy-5-phenylpentyl) isoindole-1,3-dione obtained in Step (1) of Example 66 and 3-fluoro-4-(trifluoromethyl)phenol instead of 4-(trifluoromethyl)phenol in the same manner as in Step (2) of Example 66, and then in the same manner as in Steps (3) and (4) of Example 66.

Example 69: Synthesis of (S)-5-[3-fluoro-4-(trifluoromethyl)phenoxy]-5-phenylpentan-1-amine fumarate The compound of Example 69 was obtained by using (R)-2-(5-hydroxy-5-phenylpentyl)isoindole-1,3-dione obtained in Step (1) of Example 67 and 3-fluoro-4-(trifluoromethyl)phenol instead of 4-(trifluoromethyl)phenol in the same manner as in Step (2) of Example 67, and then in the same manner as in Steps (3) and (4) of Example 67.

Example 70: Synthesis of (R)-5-phenyl-5-[4-(trifluoromethoxy) phenoxy]pentan-1-amine fumarate

(1) Synthesis of 5-chloro-1-phenylpentan-1-one

Aluminium chloride (141.9 g) was dissolved in methylene chloride (480 ml), 5-chloropentanoyl chloride (150.2 g) was added dropwise thereto under ice-cooling, and the mixture was stirred for 10 min. A dichloromethane solution (120 ml) of benzene (83.1 g) was added dropwise thereto, and the mixture was stirred at room temperature for 4 hr. The reaction solution was added dropwise to a mixture of 36% hydrochloric acid (90 g) and ice (200 g), and the mixture was extracted with ethyl acetate. The organic layer was washed successively with water and saturated brine, and dried over anhydrous sodium sulfate. The solution was filtered, and the filtrate was concentrated under reduced pressure to give the title compound (184.0 g) as a pale-yellow solid.

$^1$H NMR (400 MHz, CDCl$_3$): δ: 7.95-7.97 (m, 2H), 7.55-7.59 (m, 1H), 7.45-7.49 (m, 2H), 3.59 (t, J=6.4 Hz, 2H), 3.02 (t, J=6.8 Hz, 2H) 1.85-1.96 (m, 4H).

(2) Synthesis of 2-(5-oxo-5-phenylpentyl)isoindole-1,3-dione

5-Chloro-1-phenylpentan-1-one (184.0 g) was dissolved in N,N-dimethylformamide (920 ml), phthalimide (151.4 g) and potassium carbonate (258.6 g) were added thereto, and the mixture was stirred at 80° C. for 4 hr. The reaction solution was allowed to be cooled, water was added thereto, and the mixture was extracted with ethyl acetate. The organic layer was washed successively with water and saturated brine, and dried over anhydrous sodium sulfate. The solution was filtered, and the filtrate was concentrated under reduced pressure. To the obtained crude substance (284 g) was added diisopropyl ether (2840 ml), and the mixture was stirred at room temperature for 4 hr. The solid was collected by filtration, washed with diisopropyl ether, and dried under reduced pressure to give the title compound (193.0 g) as a pale-yellow solid.

$^1$H NMR (400 MHz, CDCl$_3$): δ: 7.94-7.96 (m, 2H), 7.83-7.86 (m, 2H), 7.70-7.73 (m, 2H), 7.53-7.57 (m, 1H), 7.43-7.47 (m, 2H), 3.75-3.77 (m, 2H), 3.04-3.07 (m, 2H) 1.79-1.82 (m, 4H).

(3) Synthesis of (S)-2-(5-hydroxy-5-phenylpentyl)isoindole-1,3-dione 2-(5-Oxo-5-phenylpentyl)isoindole-1,3-dione (50.2 g) was dissolved in tetrahydrofuran (500 ml), (−)-B-diisopinocampheylchloroborane (1.7M heptane solution) (200 ml) was dropwise thereto over 40 min under ice-cooling, and the mixture was stirred at room temperature for 90 min. The reaction solution was ice-cooled, methanol (100 ml) was added thereto, and the mixture was concentrated under reduced pressure. The residue was purified by silica gel column chromatography (hexane:ethyl acetate=3:1→2:1). The obtained objective product was dissolved in ethyl acetate (100 ml), hexane (300 ml) was added thereto, and the mixture was stirred overnight at room temperature. The precipitated crystals were collected by filtration, washed with ethyl acetate:hexane (1:3), and dried under reduced pressure to give the title compound (28.2 g) as a white solid.

$^1$H NMR (400 MHz, CDCl$_3$): δ: 7.82-7.85 (m, 2H), 7.70-7.73 (m, 2H), 7.25-7.34 (m, 5H), 4.65-4.70 (m, 1H), 3.67 (t, J=7.2 Hz, 2H), 1.68-1.90 (m, 4H), 1.48-1.58 (m, 1H), 1.36-1.44 (m, 1H). $[\alpha]_{25}^D$ −16.3° (c 0.86, CHCl$_3$)

(Optical Purity Measurement)

The optical purity of the title compound was confirmed as follows. The title compound was reacted with acetic anhydride in pyridine to give (S)-2-(5-acetoxy-5-phenylpentyl)isoindole-1,3-dione, and the optical purity of this compound was confirmed as 98% ee by analyzing using chiral column under the condition in a manner similar to Step (1) of Example 66.

(4) Synthesis of (R)-2-(5-phenyl-5-[4-(trifluoromethoxy) phenoxy]pentyl) isoindole-1,3-dione (S)-2-(5-Hydroxy-5-phenylpentyl)isoindole-1,3-dione (27.3 g) was dissolved in toluene (880 ml), 4-(trifluoromethoxy)phenol (22.4 g) and triphenylphosphine (34.9 g) were added thereto under ice-cooling, and the mixture was stirred. 1.9M Diisopropyl azodicarboxylate-toluene solution (71 ml) was added dropwise thereto, and the mixture was stirred at room temperature for 4 hr. The reaction solution was concentrated under reduced pressure, and the obtained residue was purified by silica gel column chromatography (hexane:ethyl acetate=10:1) to give the title compound (34.1 g) as a colorless liquid.

$^1$H NMR (400 MHz, CDCl$_3$): δ: 7.81-7.84 (m, 2H), 7.69-7.73 (m, 2H), 7.23-7.39 (m, 5H), 7.00 (d, J=8.8 Hz, 2H), 6.77-6.80 (m, 2H), 5.02 (dd, J=8.0, 5.2 Hz, 1H), 3.66 (t, J=7.2 Hz, 2H), 1.98-2.07 (m, 1H), 1.83-1.91 (m, 1H), 1.71-1.75 (m, 2H), 1.43-1.69 (m, 2H).

(5) Synthesis of (R)-5-phenyl-5-[4-(trifluoromethoxy)phenoxy]pentan-1-amine (R)-2-(5-Phenyl-5-[4-(trifluoromethoxy)phenoxy]pentyl)isoindole-1,3-dione (34.1 g) was dissolved in ethanol (600 ml), hydrazine monohydrate (6.8 ml) was added thereto, and the mixture was stirred at 85° C. for 4 hr. The solid was removed by filtration, and the filtrate was concentrated under reduced pressure. Ethyl acetate (500 ml) and hexane (500 ml) were added thereto, and the mixture was washed successively with saturated aqueous sodium hydrogencarbonate solution, 0.005M hydrochloric acid, saturated aqueous sodium hydrogencarbonate solution, and dried over anhydrous sodium sulfate. The solution was filtered, the filtrate was concentrated under reduced pressure, and the obtained residue was purified by silica gel column chromatography (hexane:ethyl acetate=3:1→hexane:ethyl acetate:methanol=3:1:0.1) to give the title compound (22.4 g) as a colorless liquid.

$^1$H NMR (400 MHz, CDCl$_3$): δ: 7.24-7.36 (m, 5H), 7.02 (d, J=8.8 Hz, 2H), 6.79-6.82 (m, 2H), 5.03 (dd, J=8.0, 5.2 Hz, 1H), 2.69 (t, J=6.8 Hz, 2H), 1.97-2.03 (m, 1H), 1.81-1.86 (m, 1H), 1.48-1.51 (m, 4H).

MS(ESI) m/z: 340.1 [MH$^+$], C18H20F3NO2 requires 339.14.

(6) Synthesis of (R)-5-phenyl-5-[4-(trifluoromethoxy)phenoxy]pentan-1-amine fumarate (R)-5-Phenyl-5-[4-(trifluoromethoxy)phenoxy]pentan-1-amine (19.3 g) was dissolved in ethanol (1150 ml), fumaric acid (6.0 g) was added thereto, and the mixture was stirred at room temperature for 30 min. The reaction solution was filtered, and the filtrate was concentrated under reduced pressure. To the obtained residue was added ethyl acetate:hexane=1:1 (500 ml), and the mixture was stirred at room temperature for 2 hr. The solid was collected by filtration, washed with ethyl acetate:hexane (1:1), and dried under reduced pressure to give the title compound (21.3 g) as a white solid.

$^1$H NMR (400 MHz, DMSO-$d_6$): δ: 7.32-7.41 (m, 4H), 7.24-7.27 (m, 1H), 7.18 (d, J=8.4 Hz, 2H), 6.94-6.98 (m, 2H), 6.43 (s, 2H), 5.31 (dd, J=7.6, 5.2 Hz, 1H), 2.75 (t, J=7.2 Hz, 2H), 1.88-1.93 (m, 1H), 1.74-1.80 (m, 1H), 1.56-1.63 (m, 2H), 1.47-1.56 (m, 1H), 1.33-1.42 (m, 1H).

MS(ESI) m/z: 340.1 [MH$^+$], C18H20F3NO2 requires 339.14.

Example 71: Synthesis of (S)-5-phenyl-5-[4-(trifluoromethoxy)phenoxy]pentan-1-amine fumarate The compound of Example 71 was obtained by using (R)-2-(5-hydroxy-5-phenylpentyl)isoindole-1,3-dione obtained in Step (1) of Example 67 and 4-(trifluoromethoxy)phenol instead of 4-(trifluoromethyl)phenol in the same manner as in Step (2) of Example 67, and then in the same manner as in Steps (3) and (4) of Example 67.

Examples 72 and 73

The compounds of Examples 72 and 73 were obtained in the same manner as in Example 1.

The structure formulas and NMR and MS data of the compounds of Examples are shown in Tables 1 to 18.

TABLE 1

| Ex. | Structural Formula | NMR MS |
|---|---|---|
| 1 | 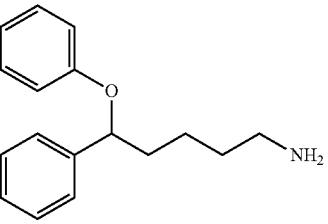 | (CDCl3) δ: 7.42 (d, J = 8.8 Hz, 2H), 7.29-7.35 (m, 4H), 7.24-7.28 (m, 1H), 6.88 (d, J = 8.8 Hz, 2H), 5.13 (dd, J = 8.0, 5.2 Hz, 1H), 2.72 (t, J = 7.2 Hz, 2H), 1.98-2.06 (m, 1H), 1.82-1.88 (m, 1H), 1.52-1.59 (m, 3H), 1.41-1.48 (m, 1H). MS(ESI) m/z: 324.4 [MH+], C18H20F3NO requires 323.35. |
| 2 | 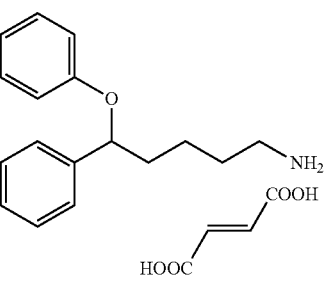 | (DMSO-d6) δ: 7.55 (d, J = 8.8 Hz, 2H), 7.39-7.42 (m, 2H), 7.33-7.36 (m, 2H), 7.24-7.28 (m, 1H), 7.06 (d, J = 8.4 Hz, 2H), 6.42 (s, 2H), 5.43 (dd, J = 7.6, 5.2 Hz, 1H), 2.75 (t, J = 7.2 Hz, 2H), 1.92-1.97 (m, 1H), 1.77-1.83 (m, 1H), 1.56-1.63 (m, 2H), 1.47-1.53 (m, 1H), 1.35-1.41 (m, 1H). MS(ESI) m/z: 324.4 [MH+], C18H20F3NO requires 323.35. |
| 3 | 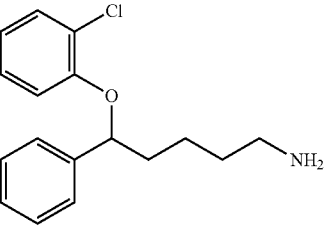 [SMILES: NCCCCC(Oc1ccccc1C(F)(F)F)c1ccccc1] | (CDCl3) δ: 7.60 (d, J = 2.0 Hz, 1H), 7.31-7.36 (m, 4H), 7.26-7.29 (m, 2H), 6.75 (d, J = 8.8 Hz, 1H), 5.19 (dd, J = 7.6, 5.2 Hz, 1H), 2.74 (t, J = 6.8 Hz, 2H), 2.07-2.13 (m, 1H), 1.87-1.94 (m, 1H), 1.46-1.64 (m, 4H). MS(ESI) m/z: 358.3 [MH+], C18H19ClF3NO requires 357.11 |
| 4 | 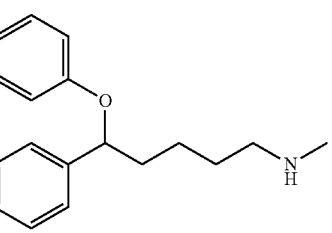 | (CDCl3) δ: 7.42 (d, J = 8.4 Hz, 2H), 7.30-7.35 (m, 4H), 7.24-7.28 (m, 1H), 6.88 (d, J = 8.8 Hz, 2H), 5.13 (dd, J = 8.0, 4.8 Hz, 1H), 2.60 (t, J = 6.4 Hz, 2H), 2.43 (s, 3H), 2.02-2.05 (m, 1H), 1.84-1.88 (m, 1H), 1.43-1.58 (m, 4H). MS(ESI) m/z: 338.3 [MH+], C19H22F3NO requires 337.17. |

TABLE 2

| Ex. | Structural Formula | NMR(CDCl3) MS |
|---|---|---|
| 5 | 4-CF3-C6H4-O-CH(C6H5)-CH2CH2CH2CH2-N(CH3)2 | δ: 7.42 (d, J = 8.8 Hz, 2H), 7.31-7.34 (m, 4H), 7.24-7.28 (m, 1H), 6.88 (d, J = 8.4 Hz, 2H), 5.12 (dd, J = 8.0, 5.2 Hz, 1H), 2.23 (t, J = 7.2 Hz, 2H), 2.20 (s, 6H), 1.99-2.06 (m, 1H), 1.82-1.88 (m, 1H), 1.36-1.55 (m, 4H). MS(ESI) m/z: 352.3 [MH+], C20H24F3NO requires 351.18. |
| 6 | 4-CF3-C6H4-O-CH(C6H5)-(CH2)5-NH2 | δ: 7.42 (d, J = 8.4 Hz, 2H), 7.33-7.35 (m, 4H), 7.24-7.32 (m, 1H), 6.88 (d, J = 8.4 Hz, 2H), 5.12 (dd, J = 7.6, 5.2 Hz, 1H), 2.67 (t, J = 6.8 Hz, 2H), 1.97-2.05 (m, 1H), 1.81-1.87 (m, 1H), 1.34-1.61 (m, 6H). MS(ESI) m/z: 338.3 [MH+], C19H22F3NO requires 337.17. |
| 7 | 4-CF3-2-Cl-C6H3-O-CH(C6H5)-(CH2)5-NH2 | δ: 7.60 (d, J = 1.6 Hz, 1H), 7.31-7.37 (m, 4H), 7.25-7.29 (m, 2H), 6.76 (d, J = 8.8 Hz, 1H), 5.18 (dd, J = 7.6, 5.2 Hz, 1H), 2.69 (t, J = 6.8 Hz, 2H), 2.07-2.11 (m, 1H), 1.87-1.93 (m, 1H), 1.36-1.63 (m, 6H). MS(ESI) m/z: 372.3 [MH+], C19H21ClF3NO requires 371.13. |
| 8 | 4-CF3-C6H4-O-CH(C6H5)-(CH2)5-N(CH3)2 | δ: 7.42 (d, J = 8.8 Hz, 2H), 7.30-7.35 (m, 4H), 7.24-7.28 (m, 1H), 6.88 (d, J = 8.4 Hz, 2H), 5.12 (dd, J = 8.0, 5.2 Hz, 1H), 2.24 (t, J = 7.2 Hz, 2H), 2.21 (s, 6H), 1.99-2.03 (m, 1H), 1.81-1.87 (m, 1H), 1.23-1.51 (m, 6H). MS(ESI) m/z: 366.3 [MH+], C21H28F3NO requires 365.2. |

TABLE 3

| Ex. | Structural Formula | NMR(CDCl3) MS |
|---|---|---|
| 9 | 4-CF3-C6H4-O-CH(C6H5)-(CH2)5-NH(CH3) | δ: 7.43 (d, J = 8.4 Hz, 2H), 7.30-7.35 (m, 4H), 7.24-7.28 (m, 1H), 6.88 (d, J = 8.4 Hz, 2H), 5.12 (dd, J = 7.6, 4.8 Hz, 1H), 2.57 (t, J = 6.8 Hz, 2H), 2.43 (s, 3H), 1.99-2.03 (m, 1H), 1.81-1.87 (m, 1H), 1.33-1.54 (m, 6H). MS(ESI) m/z: 352.3 [MH+], C20H24F3NO requires 351.18. |
| 10 | 4-CF3-C6H4-O-CH(4-CH3-C6H4)-(CH2)4-NH2 | δ: 7.41 (d, J = 8.8 Hz, 2H), 7.18 (d, J = 8.4 Hz, 2H), 7.12 (d, J = 8.0 Hz, 2H), 6.87 (d, J = 8.4 Hz, 2H), 5.09 (dd, J = 8.0, 4.8 Hz, 1H), 2.81 (t, J = 6.8 Hz, 2H), 2.31 (s, 3H), 1.96-2.03 (m, 1H), 1.80-1.87 (m, 1H), 1.45-1.65 (m, 4H). MS(ESI) m/z: 338.3 [MH+], C19H22F3NO requires 337.17. |

TABLE 3-continued

| Ex. | Structural Formula | NMR(CDCl3) MS |
|---|---|---|
| 11 | (4-CF3-phenyl)-O-CH(4-F-phenyl)-CH2CH2CH2CH2-NH2 | δ: 7.43 (d, J = 8.8 Hz, 2H), 7.26-7.30 (m, 2H), 7.00-7.04 (m, 2H), 6.86 (d, J = 8.8 Hz, 2H), 5.12 (dd, J = 7.6, 5.2 Hz, 1H), 2.79 (t, J = 7.2 Hz, 2H), 1.96-2.04 (m, 1H), 1.79-1.87 (m, 1H), 1.42-1.64 (m, 4H).<br>MS(ESI) m/z: 342.2 [MH+], C18H19F4NO requires 341.14. |
| 12 | (4-CF3-phenyl)-O-CH(3-F-phenyl)-CH2CH2CH2CH2-NH2 | δ: 7.44 (d, J = 8.8 Hz, 2H), 7.27-7.33 (m, 1H), 7.09 (d, J = 7.6 Hz, 1H), 7.01-7.04 (m, 1H), 6.93-6.98 (m, 1H), 6.87 (d, J = 8.4 Hz, 2H), 5.12 (dd, J = 7.6, 5.2 Hz, 1H), 2.76 (t, J = 7.2 Hz, 2H), 1.97-2.01 (m, 1H), 1.83-1.87 (m, 1H), 1.43-1.57 (m, 4H).<br>MS(ESI) m/z: 342.2 [MH+], C18H19F4NO requires 341.14. |

TABLE 4

| Ex. | Structural Formula | NMR(CDCl3) MS |
|---|---|---|
| 13 | (4-CF3-phenyl)-O-CH(4-MeO-phenyl)-CH2CH2CH2CH2-NH2 | δ: 7.42(d, J = 8.8 Hz, 2H), 7.22-7.24(m, 2H), 6.85-6.89(m, 4H), 5.08(dd, J = 7.6, 5.2 Hz, 1H), 3.78(s, 3H), 2.72(t, J = 7.2 Hz, 2H), 1.97-2.06(m, 1H), 1.79-1.85(m, 1H), 1.36-1.54(m, 4H).<br>MS(ESI) m/z: 354.2[MH+], C19H22F3NO2 requires 353.16. |
| 14 | (2-naphthyl)-O-CH(phenyl)-CH2CH2CH2CH2-NH2 | δ: 7.68-7.71(m, 2H), 7.56(d, J = 8.0 Hz, 1H), 7.39-7.41(m, 2H), 7.20-7.37(m, 6H), 7.00(d, J = 2.4 Hz, 1H), 5.25(dd, J = 8.0, 5.2 Hz, 1H), 2.70(t, J = 6.8 Hz, 2H), 2.02-2.13(m, 1H), 1.85-1.94(m, 1H), 1.43-1.61(m, 4H).<br>MS(ESI) m/z: 306.2[MH+], C21H23NO requires 305.18. |
| 15 | (1-naphthyl)-O-CH(phenyl)-CH2CH2CH2CH2-NH2 | δ: 8.43(d, J = 8.2 Hz, 1H), 7.76(d, J = 6.8 Hz, 1H), 7.48-7.51(m, 2H), 7.15-7.39(m, 7H), 6.59(d, J = 7.6 Hz, 1H), 5.31(dd, J = 8.0, 5.2 Hz, 1H), 2.76(t, J = 6.8 Hz, 2H), 2.13-2.17(m, 1H), 1.92-1.99(m, 1H), 1.52-1.65(m, 4H).<br>MS(ESI) m/z: 306.3[MH+], C21H23NO requires 305.18. |

TABLE 4-continued

| Ex. | Structural Formula | NMR(CDCl3) MS |
|-----|---|---|
| 16 | | δ: 7.47-7.49(m, 2H), 7.32-7.42(m, 8H), 7.25-7.29(m, 2H), 6.89-6.92(m, 2H), 5.13(dd, J = 8.0, 4.8 Hz, 1H), 2.70(t, J = 6.8 Hz, 2H), 2.02-2.08(m, 1H), 1.83-1.89(m, 1H), 1.42-1.58(m, 4H). MS(ESI) m/z: 332.3[MH+], C23H25NO requires 331.19. |

TABLE 5

| Ex. | Structural Formula | NMR(CDCl3) MS |
|-----|---|---|
| 17 | | δ: 7.33-7.35(m, 4H), 7.19-7.29(m, 2H), 7.11-7.14(m, 2H), 6.95(d, J = 8.0 Hz, 1H), 5.11(dd, J = 7.6, 5.2 Hz, 1H), 2.68(t, J = 6.8 Hz, 2H), 1.99-2.08(m, 1H), 1.81-1.89(m, 1H), 1.49-1.59(m, 4H). MS(ESI) m/z: 324.1[MH+], C18H20F3NO requires 323.15. |
| 18 | | δ: 7.54(d, J = 7.6 Hz, 1H), 7.30-7.34(m, 5H), 7.24-7.27(m, 1H), 6.89(t, J = 7.6 Hz, 1H), 6.73(d, J = 8.8 Hz, 1H), 5.20(dd, J = 8.0, 4.8 Hz, 1H), 2.68(t, J = 6.8 Hz, 2H), 2.00-2.09 (m, 1H), 1.83-1.91(m, 1H), 1.41-1.61(m, 4H). MS(ESI) m/z: 324.1[MH+], C18H20F3NO requires 323.15. |
| 19 | | δ: 7.17-7.30(m, 8H), 7.09-7.12(m, 3H), 6.99(t, J = 7.6 Hz, 1H), 6.79(t, J = 7.6 Hz, 1H), 6.58(d, J = 8.4 Hz, 1H), 5.07 (dd, J = 7.6, 4.8 Hz, 1H), 4.05(s, 2H), 2.69(t, J = 7.2 Hz, 2H), 1.89-1.98(m, 1H), 1.72-1.79(m, 1H), 1.50-1.55(m, 2H), 1.24-1.45(m, 2H). MS(ESI) m/z: 346.3[MH+], C24H27NO requires 345.21. |
| 20 | | δ: 7.20-7.30(m, 7H), 7.11-7.17(m, 3H), 6.96(d, J = 8.4 Hz, 2H), 6.73(d, J = 8.8 Hz, 1H), 5.01(dd, J = 8.0, 4.8 Hz, 1H), 3.84(s, 2H), 2.79(t, J = 7.2 Hz, 2H), 1.92-1.99(m, 1H), 1.77-1.84(m, 1H), 1.55-1.63(m, 3H), 1.37-1.46(m, 1H). MS(ESI) m/z: 346.3[MH+], C24H27NO requires 345.21. |

TABLE 6

| Ex. | Structural Formula | NMR(CDCl3) MS |
|---|---|---|
| 21 | (4-methoxyphenoxy)(phenyl)pentylamine structure | δ: 7.29-7.33(m, 4H), 7.23-7.27(m, 1H), 6.70-6.77(m, 4H), 4.98(dd, J = 8.0, 4.8 Hz, 1H), 3.71(s, 3H), 2.68(t, J = 6.8 Hz, 2H), 1.97-2.00(m, 1H), 1.79-1.84(m, 1H), 1.42-1.58(m, 4H). MS(ESI) m/z: 286.3[MH+], C18H23NO2 requires 285.17. |
| 22 | (4-propoxyphenoxy)(phenyl)pentylamine structure | δ: 7.22-7.31(m, 5H), 6.69-6.75(m, 4H), 4.96(dd, J = 8.0, 4.8 Hz, 1H), 3.79(t, J = 6.8 Hz, 2H), 2.77(t, J = 6.8 Hz, 2H), 1.94-2.00 (m, 1H), 1.69-1.84(m, 3H), 1.55-1.65(m, 3H), 1.43-1.50(m, 1H), 0.98(t, J = 7.2 Hz, 3H). MS(ESI) m/z: 314.3[MH+], C20H27NO2 requires 313.2. |
| 23 | (4-benzyloxyphenoxy)(phenyl)pentylamine structure | δ: 7.24-7.40(m, 10H), 6.74-6.80(m, 4H), 4.94-4.99(m, 3H), 2.70(t, J = 6.4 Hz, 2H), 1.92-1.98(m, 1H), 1.77-1.83(m, 1H), 1.44-1.57(m, 4H). MS(ESI) m/z: 362.3[MH+], C24H27NO2 requires 361.20. |
| 24 | (4-isopropylphenoxy)(phenyl)pentylamine structure | δ: 7.24-7.36(m, 5H), 7.03(dd, J = 6.8, 1.6 Hz, 2H), 6.75-6.78(m, 2H), 5.04(dd, J = 8.0, 4.8 Hz, 1H), 2.74-2.84(m, 1H), 2.68(t, J = 6.8 Hz, 1H), 1.93-2.03(m, 1H), 1.74-1.83(m, 1H), 1.41-1.58(m, 4H), 1.17(d, J = 6.8 Hz, 6H). MS(ESI) m/z: 298.3[MH+], C20H27NO requires 297.21. |

TABLE 7

| Ex. | Structural Formula | NMR(CDCl3) MS |
|---|---|---|
| 25 | (4-ethylphenoxy)(phenyl)pentylamine structure | δ: 7.21-7.35(m, 5H), 6.99(d, J = 8.4 Hz, 2H), 6.75(dd, J = 6.8, 2.0 Hz, 2H), 5.04(dd, J = 8.0, 4.8 Hz, 1H), 2.72(t, J = 7.2 Hz, 2H), 2.53(q, J = 7.6 Hz, 2H), 1.97-2.00(m, 1H), 1.80-1.84(m, 1H), 1.43-1.60(m, 4H), 1.15(t, J = 6.8 Hz, 6H). MS(ESI) m/z: 284.3[MH+], C19H25NO requires 283.19. |

TABLE 7-continued

| Ex. | Structural Formula | NMR(CDCl3) MS |
|---|---|---|
| 26 | | δ: 7.23-7.25(m, 5H), 6.97(d, J = 8.4 Hz, 2H), 6.75(dd, J = 6.8, 2.0 Hz, 2H), 5.03(dd, J = 8.0, 4.8 Hz, 1H), 2.72(t, J = 7.2 Hz, 2H), 2.46-2.49(m, 1H), 1.92-1.99(m, 1H), 1.79-1.83(m, 1H), 1.43-1.56(m, 6H), 1.14(dd, J = 6.8, 1.6 Hz, 3H), 0.77(t, J = 6.8 Hz, 3H). MS(ESI) m/z: 312.3[MH+], C21H29NO requires 311.22. |
| 27 | | δ: 7.24-7.36(m, 5H), 7.18(dd, J = 6.8, 2.0 Hz, 2H), 6.76(dd, J = 6.8, 2.4 Hz, 2H), 5.04(dd, J = 8.0, 4.8 Hz, 1H), 2.70(t, J = 6.8 Hz, 2H), 1.75-1.99(m, 2H), 1.40-1.59(m, 4H), 1.24(s, 9H). MS(ESI) m/z: 312.3[MH+], C21H29NO requires 311.22. |
| 28 | | δ: 7.24-7.35(m, 6H), 6.93-6.98(m, 1H), 6.65-6.68(m, 1H), 5.13(dd, J = 8.0, 4.8 Hz, 1H), 2.75(t, J = 7.6 Hz, 2H), 2.00-2.08(m, 1H), 1.84-1.89(m, 1H), 1.43-1.59(m, 4H). MS(ESI) m/z: 342.3[MH+], C19H29F4NO requires 341.14. |

TABLE 8

| Ex. | Structural Formula | NMR(CDCl3) MS |
|---|---|---|
| 29 | | δ: 7.26-7.39(m, 6H), 6.61-6.67(m, 2H), 5.10(dd, J = 8.0, 5.2 Hz, 1H), 2.69(t, J = 6.8 Hz, 2H), 1.97-2.08(m, 1H), 1.80-1.89(m, 1H), 1.34-1.58(m, 4H). MS(ESI) m/z: 342.2[MH+], C18H19F4NO requires 341.14. |
| 30 | | δ: 7.26-7.32(m, 5H), 6.83-6.87(m, 2H), 6.74-6.77(m, 2H), 4.99(dd, J = 7.2, 5.6 Hz, 1H), 2.67-2.70(m, 2H), 1.92-2.08(m, 1H), 1.76-1.88(m, 1H), 1.38-1.62(m, 4H). MS(ESI) m/z: 274.3[MH+], C17H20FNO requires 273.15. |

TABLE 8-continued

| Ex. | Structural Formula | NMR(CDCl3) MS |
|---|---|---|
| 31 | (1-phenoxy-1-phenylpentyl)amine structure | δ: 7.24-7.35(m, 4H), 7.15-7.19(m, 3H), 6.82-6.87(m, 3H), 5.09(dd, J = 7.6, 4.8 Hz, 1H), 1.95-2.08(m, 1H), 1.75-1.88(m, 1H), 1.36-1.54(m, 6H). MS(ESI) m/z: 256.2[MH+], C17H21NO requires 255.16. |
| 32 | 4-chlorophenoxy phenylpentylamine structure | δ: 7.23-7.34(m, 5H), 7.09-7.13(m, 2H), 6.74-6.77(m, 2H), 5.03(dd, J = 8.0, 5.2 Hz, 1H), 2.69(t, J = 6.8 Hz, 2H), 1.95-2.01(m, 1H), 1.79-1.85(m, 1H), 1.29-1.56(m, 4H). MS(ESI) m/z: 290.3[MH+], C17H20ClNO requires 289.12. |

TABLE 9

| Ex. | Structural Formula | NMR(CDCl3) MS |
|---|---|---|
| 33 | 4-methylphenoxy phenylpentylamine structure | δ: 7.29-7.34(m, 4H), 7.21-7.26(m, 1H), 6.96(d, J = 8.4 Hz, 2H), 6.72(d, J = 8.4 Hz, 2H), 5.04(dd, J = 8.0, 5.2 Hz, 1H), 2.68(t, J = 6.8 Hz, 2H), 2.21(s, 3H), 1.95-2.02(m, 1H), 1.77-1.85(m, 1H), 1.37-1.55(m, 4H). MS(ESI) m/z: 270.3[MH+], C18H23NO requires 269.18. |
| 34 | 4-nitrophenoxy phenylpentylamine structure | δ: 8.06-8.10(m, 2H), 7.26-7.37(m, 5H), 6.86-6.92(m, 2H), 5.19(dd, J = 7.6, 5.2 Hz, 1H), 2.70(t, J = 6.8 Hz, 2H), 2.03-2.08(m, 1H), 1.85-1.91(m, 1H), 1.37-1.58(m, 4H). MS(ESI) m/z: 301.2[MH+], C17H20N2O3 requires 300.15. |
| 35 | quinolin-4-yloxy phenylpentylamine structure | δ: 8.55(d, J = 5.2 Hz, 1H), 8.37(d, J = 8.4 Hz, 1H), 8.01(d, J = 8.4 Hz, 1H), 7.68-7.72(m, 1H), 7.53-7.57(m, 1H), 7.25-7.38(m, 5H), 6.52(d, J = 5.2 Hz, 1H), 5.38(dd, J = 8.0, 5.2 Hz, 1H), 2.75(t, J = 6.8 Hz, 2H), 1.95-2.27(m, 2H), 1.43-1.67(m, 4H). MS(ESI) m/z: 307.4[MH+], C20H22N2O requires 306.17. |

TABLE 9-continued

| Ex. | Structural Formula | NMR(CDCl3) MS |
|---|---|---|
| 36 | (pyridin-4-yloxy phenyl pentylamine structure) | δ: 8.30-8.32(m, 2H), 7.26-7.36(m, 5H), 6.72-6.74(m, 2H), 5.16(dd, J = 8.0, 5.2 Hz, 1H), 2.70(t, J = 6.8 Hz, 2H), 2.01-2.06(m, 1H), 1.83-1.89(m, 1H), 1.42-1.55(m, 4H). MS(ESI) m/z: 257.4[MH+], C16H20N2O requires 256.16. |

TABLE 10

| Ex. | Structural Formula | NMR(CDCl3) MS |
|---|---|---|
| 37 | (3-cyanophenoxy phenyl pentylamine structure) | δ: 7.23-7.35(m, 6H), 7.13-7.15(m, 1H), 7.03-7.06(m, 2H), 5.08(dd, J = 8.0, 5.2 Hz, 1H), 2.78(t, J = 6.8 Hz, 2H), 1.97-2.05(m, 1H), 1.82-1.89(m, 1H), 1.42-1.62(m, 4H). MS(ESI) m/z: 281.5[MH+], C18H20N2O requires 280.16. |
| 38 | (4-(cyanomethyl)phenoxy phenyl pentylamine structure) | δ: 7.28-7.34(m, 5H), 7.09-7.11(m, 2H), 6.79-6.83(m, 2H), 5.06(dd, J = 8.0, 5.2 Hz, 1H), 3.59(s, 2H), 2.80(t, J = 7.2 Hz, 2H), 1.95-2.05(m, 1H), 1.80-1.86(m, 1H), 1.43-1.63(m, 4H). MS(ESI) m/z: 295.4[MH+], C19H22N2O requires 294.17. |
| 39 | (quinolin-8-yloxy phenyl pentylamine structure) | δ: 9.00-9.02(m, 1H), 8.07-8.10(m, 1H), 7.38-7.43(m, 3H), 7.29-7.33(m, 3H), 7.22-7.26(m, 2H), 6.81-6.84(m, 1H), 5.36(dd, J = 8.0, 4.4 Hz, 1H), 3.00(t, J = 6.4 Hz, 2H), 2.25-2.35(m, 1H), 2.02-2.08(m, 1H), 1.62-1.81(m, 4H). MS(ESI) m/z: 307.4[MH+], C20H22N2O requires 306.17. |
| 40 | (biphenyl-3-yloxy phenyl pentylamine structure) | δ: 7.20-7.50(m, 11H), 7.08-7.10(m, 2H), 6.78-6.81(m, 2H), 5.15(dd, J = 8.0, 5.2 Hz, 1H), 2.71(t, J = 6.4 Hz, 2H), 2.00-2.08(m, 1H), 1.82-1.88(m, 1H), 1.43-1.58(m, 4H). MS(ESI) m/z: 332.3[MH+], C23H25NO requires 331.19. |

TABLE 11

| Ex. | Structural Formula | NMR(CDCl3) MS |
|---|---|---|
| 41 | (quinolin-2(1H)-one with 5-O-CH(Ph)-(CH2)3-CH2NH2 substituent) | δ: 9.98(s, 1H), 7.31-7.38(m, 4H), 7.24(t, J = 7.2 Hz, 1H), 6.90(t, J = 8.0 Hz, 1H), 6.40(dd, J = 12.0, 8.0 Hz, 2H), 5.28(dd, J = 7.2, 5.2 Hz, 1H), 2.91(t, J = 7.6 Hz, 2H), 2.58(t, J = 6.8 Hz, 2H), 2.41-2.46(m, 2H), 1.88-1.93(m, 1H), 1.75-1.80(m, 1H), 1.32-1.42(m, 4H). MS(ESI) m/z: 325.3[MH+], C20H24N2O2 requires 324.18. |
| 42 | NC-C6H4-O-CH(Ph)-(CH2)3-CH2NH2 | δ: 7.44-7.48(m, 2H), 7.25-7.36(m, 5H), 6.85-6.89(m, 2H), 5.13(dd, J = 7.6, 5.2 Hz, 1H), 2.69(t, J = 6.8 Hz, 2H), 1.99-2.04(m, 1H), 1.82-1.95(m, 1H), 1.40-1.56(m, 4H). MS(ESI) m/z: 281.3[MH+], C18H20N2O requires 280.16. |
| 43 | MeOOC-C6H4-O-CH(Ph)-(CH2)3-CH2NH2 | δ: 7.87(dd, J = 7.2, 2.0 Hz, 2H), 7.25-7.33(m, 5H), 6.84(dd, J = 6.8, 2.0 Hz, 2H), 5.16(dd, J = 8.4, 5.2 Hz, 1H), 3.84(s, 3H), 2.69(t, J = 6.8 Hz, 2H), 1.99-2.06(m, 1H), 1.81-1.88(m, 1H), 1.43-1.53(m, 4H). MS(ESI) m/z: 314.4[MH+], C19H23NO3 requires 313.17. |
| 44 | F3CO-C6H4-O-CH(Ph)-(CH2)3-CH2NH2 | δ: 7.24-7.36(m, 5H), 7.00-7.03(m, 2H), 6.79-7.00(m, 2H), 5.03(dd, J = 8.0, 5.2 Hz, 1H), 2.69(t, J = 6.8 Hz, 2H), 2.01-2.03(m, 1H), 1.81-1.99(m, 1H), 1.37-1.58(m, 4H). MS(ESI) m/z: 340.3[MH+], C18H20F3NO2 requires 339.14. |

TABLE 12

| Ex. | Structural Formula | NMR(CDCl3) MS |
|---|---|---|
| 45 | F3CS-C6H4-O-CH(Ph)-(CH2)3-CH2NH2 | δ: 7.43-7.46(m, 2H), 7.24-7.36(m, 5H), 6.83-6.86(m, 2H), 5.10(dd, J = 8.0, 5.2 Hz, 1H), 2.70(t, J = 7.2 Hz, 2H), 1.97-2.02(m, 1H), 1.80-1.88(m, 1H), 1.40-1.61(m, 4H). MS(ESI) m/z: 356.2[MH+], C19H27NOS requires 355.12. |

TABLE 12-continued

| Ex. | Structural Formula | NMR(CDCl3) MS |
|---|---|---|
| 46 | EtO-C6H4-O-CH(Ph)-(CH2)4-NH2 | δ: 7.23-7.32(m, 5H), 6.69-6.76(m, 4H), 4.97 (dd, J = 8.0, 5.2 Hz, 1H), 3.91(q, J = 7.2 Hz, 2H 2H), 2.70(t, J = 6.8 Hz, 2H), 1.92-2.03(m, 1H), 1.77-1.83(m, 1H), 1.32-1.58(m, 7H). MS(ESI) m/z: 300.3[MH+], C19H25NO2 requires 299.19. |
| 47 | F3C-SO2-C6H4-O-CH(Ph)-(CH2)4-NH2 | δ: 7.83(d, J = 9.2 Hz, 2H), 7.29-7.38(m, 4H), 7.02(d, J = 8.8 Hz, 2H), 5.19(dd, J = 8.0, 5.2 Hz, 1H), 2.76(t, J = 6.8 Hz, 2H), 2.01-2.10(m, 1H), 1.85-1.92(m, 1H), 1.43-1.58 (m, 4H). MS(ESI) m/z: 388.2[MH+], C18H20F3NO3S requires 387.11. |
| 48 | F3C-C6H4-O-CH(2-thienyl)-(CH2)4-NH2 | δ: 7.47(d, J = 8.8 Hz, 2H), 7.23-7.24(m, 1H), 6.94-7.01(m, 4H), 5.43(dd, J = 7.2, 6.4 Hz, 1H), 2.70(t, J = 6.8 Hz, 2H), 2.11-2.16(m, 1H), 1.93-1.98(m, 1H), 1.40-1.57(m, 4H). MS(ESI) m/z: 330.2[MH+], C16H18F3NOS requires 329.11. |

TABLE 13

| Ex. | Structural Formula | NMR(CDCl3) MS |
|---|---|---|
| 49 | 1-naphthyl-O-CH(2-thienyl)-(CH2)4-NH2 | δ: 8.34-8.36(m, 1H), 7.76-7.79(m, 1H), 7.47-7.51(m, 2H), 7.38(d, J = 8.4 Hz, 1H), 7.25-7.29(m, 1H), 7.20-7.22(m, 1H), 7.04-7.05(m, 1H), 6.92-6.95(m, 1H), 6.82(d, J = 7.6 Hz, 1H), 5.60-5.63(m, 1H), 2.70(t, J = 6.8 Hz, 2H), 2.22-2.31(m, 1H), 2.03-2.10(m, 1H), 1.43-1.63(m, 4H). MS(ESI) m/z: 312.2[MH+], C19H21NOS requires 311.13. |
| 50 | F3CO-C6H4-O-CH(2-thienyl)-(CH2)4-NH2 | δ: 7.23-7.24(m, 1H), 7.03-7.07(m, 2H), 6.08-6.98(m, 2H), 6.88-6.90(m, 2H), 5.33 (dd, J = 7.2, 6.0 Hz, 1H), 2.71(t, J = 6.8 Hz, 2H), 2.07-2.15(m, 1H), 1.89-1.96(m, 1H), 1.43-1.59(m, 4H). MS(ESI) m/z: 346.2[MH+], C16H18F3NO2S requires 345.10. |

TABLE 13-continued

| Ex. | Structural Formula | NMR(CDCl3) MS |
|---|---|---|
| 51 | 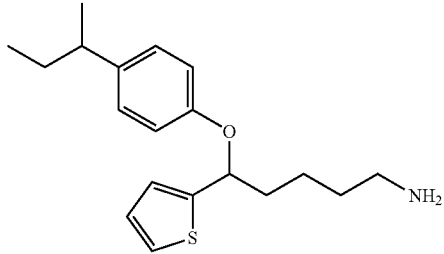 [SMILES: CCC(C)c1ccc(OC(CCCCN)c2cccs2)cc1] | δ: 7.21-7.22(m, 1H), 6.92-7.03(m, 4H), 6.82-6.84(m, 2H), 5.33(dd, J = 7.2, 6.0 Hz, 1H), 2.71(t, J = 7.2 Hz, 2H), 2.45-2.53(m, 1H), 1.88-2.12(m, 2H), 1.41-1.55(m, 6H), 1.16-1.19(m, 3H), 0.77-0.82(m, 3H). MS(ESI) m/z: 318.3[MH+], C19H27NOS requires 317.18. |
| 52 | 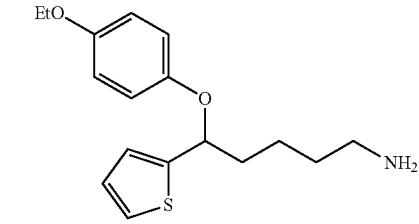 [SMILES: CCOc1ccc(OC(CCCCN)c2cccs2)cc1] | δ: 7.21-7.22(m, 1H), 6.91-6.94(m, 2H), 6.73-6.83(m, 4H), 5.23(dd, J = 7.2, 6.0 Hz, 1H), 3.91-3.97(m, 2H), 2.70(t, J = 6.8 Hz, 2H), 2.05-2.15(m, 1H), 1.86-1.93(m, 1H), 1.36-1.59(m, 7H). MS(ESI) m/z: 306.2[MH+], C16H18F3NO2S requires 305.14. |

TABLE 14

| Ex. | Structural Formula | NMR(CDCl3) MS |
|---|---|---|
| 53 | 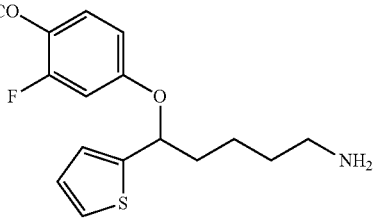 | δ: 7.25-7.26(m, 1H), 7.10-7.14(m, 1H), 6.94-7.00(m, 2H), 6.66-6.76(m, 2H), 5.31 (dd, J = 7.6, 6.4 Hz, 1H), 2.71(t, J = 6.8 Hz, 2H), 2.10-2.13(m, 1H), 1.92-1.96(m, 1H), 1.42-1.56(m, 4H). MS(ESI) m/z: 364.1[MH+], C16H17F4NO2S requires 363.09. |
| 54 | 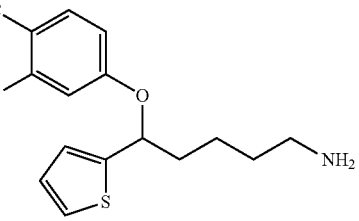 | δ: 7.42(t, J = 8.4 Hz, 1H), 7.25-7.26(m, 1H), 7.01-7.02(m, 1H), 6.95-6.97(m, 1H), 6.71-6.76(m, 2H), 5.40(dd, J = 7.2, 6.0 Hz, 1H), 2.72(t, J = 6.8 Hz, 2H), 2.09-2.15(m, 1H), 1.92-1.98(m, 1H), 1.44-1.58(m, 4H). MS(ESI) m/z: 348.2[MH+], C16H17F4NOS requires 347.10. |
| 55 | 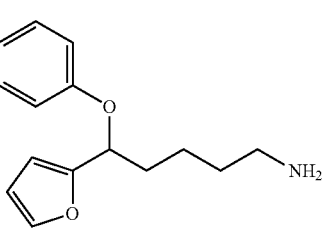 | δ: 7.49(d, J = 8.4 Hz, 2H), 7.37-7.38(m, 1H), 6.97(d, J = 8.0 Hz, 2H), 6.27-6.33(m, 2H), 5.21(t, J = 6.8 Hz, 1H), 2.70-2.72(m, 2H), 2.00-2.17(m, 2H), 1.35-1.56(m, 4H). MS(ESI) m/z: 314.3[MH+], C16H18F3NO2 requires 313.13. |
| 56 | 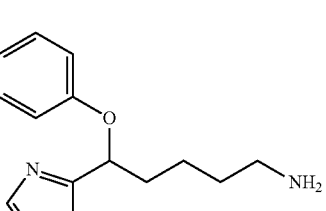 | δ: 7.76(d, J = 3.2 Hz, 1H), 7.49(d, J = 8.4 Hz, 2H), 7.31(d, J = 3.2 Hz, 1H), 7.02(d, J = 8.8 Hz, 2H), 5.58(dd, J = 8.0, 5.2 Hz, 1H), 2.72(t, J = 7.2 Hz, 2H), 2.04-2.21(m, 2H), 1.51-1.62(m, 4H). MS(ESI) m/z: 331.2[MH+], C15H17F3N2OS requires 330.10. |

TABLE 15

| Ex. | Structural Formula | NMR(CDCl3) MS |
|---|---|---|
| 57 | 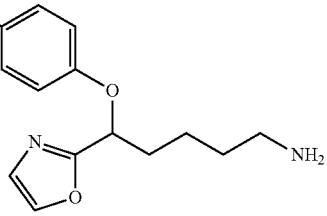 | δ: 7.87(s, 1H), 7.62(s, 1H), 7.54(s, 1H), 7.49-7.54(m, 4H), 7.10(s, 1H), 7.04(d, J = 8.4 Hz, 2H), 6.97(d, J = 8.4 Hz, 2H), 5.34-5.37 (m, 1H), 5.26-5.29(m, 1H), 2.77(brs, 4H), 2.04-2.22(m, 4H), 1431-1.58(m, 8H). MS(ESI) m/z: 315.2[MH+], C15H17F3N2O2 requires 314.12. |
| 58 | 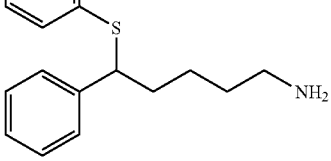 | δ: 7.41(d, J = 8.0 Hz, 2H), 7.19-7.29(m, 7H), 4.23(dd, J = 8.4, 4.8 Hz, 1H), 2.69(t, J = 6.8 Hz, 2H), 1.90-2.02(m, 2H), 1.39-1.53(m, 4H). MS(ESI) m/z: 340.2[MH+], C18H20F3NS requires 339.13. |
| 59 | 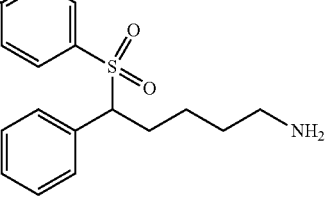 | δ: 7.59-7.64(m, 4H), 7.22-7.32(m, 3H), 7.07(d, J = 7.2 Hz, 2H), 4.07(dd, J = 11.6, 4.0 Hz, 1H), 2.64-2.69(m, 2H), 2.43-2.49(m, 1H), 2.16-2.23(m, 1H), 1.45-1.54(m, 2H), 1.24-1.32(m, 2H). MS(ESI) m/z: 372.2[MH+], C18H20F3NO2S requires 371.12. |
| 60 | 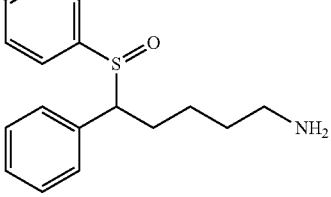 | δ: 7.55(d, J = 8.0 Hz, 2H), 7.23-7.33(m, 5H), 6.91-6.93(m, 2H), 3.64(dd, J = 11.6, 4.0 Hz, 1H), 2.62-2.65(m, 2H), 2.33-2.44(m, 1H), 2.03-2.16(m, 1H), 1.43-1.54(m, 2H), 1.28-1.32(m, 2H). MS(ESI) m/z: 356.2[MH+], C18H20F3NOS requires 355.12. |

TABLE 16

| Ex. | Structural Formula | NMR(CDCl3) MS |
|---|---|---|
| 61 | 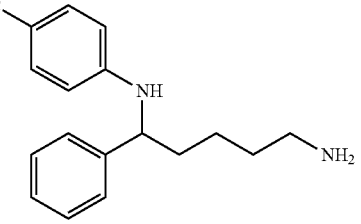 | δ: 7.23-7.35(m, 7H), 6.51(d, J = 8.4 Hz, 2H), 4.45-4.47(m, 1H), 4.33-4.36(m, 1H), 2.67-2.69(m, 2H), 1.81-1.88(m, 2H), 1.38-1.49(m, 4H). MS(ESI) m/z: 323.3[MH+], C18H21F3N2 requires 322.17. |
| 62 | 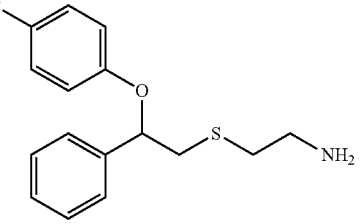 | δ: 7.44(d, J = 8.8 Hz, 2H), 7.28-7.38(m, 5H), 6.91(d, J = 8.8 Hz, 2H), 5.29(dd, J = 8.0, 4.8 Hz, 1H), 3.13(dd, J = 14.0, 8.0 Hz, 1H), 2.88-2.94(m, 3H), 2.60-2.73(m, 2H). MS(ESI) m/z: 342.2[MH+], C17H18F3NOS requires 341.11. |

TABLE 16-continued

| Ex. | Structural Formula | NMR(CDCl3) MS |
|---|---|---|
| 63 | (4-CF3-C6H4-O-CH(Ph)-CH2-O-CH2CH2-NH2) | δ: 7.44(d, J = 8.8 Hz, 2H), 7.30-7.37(m, 5H), 6.94(d, J = 8.4 Hz, 2H), 5.38(dd, J = 8.0, 3.6 Hz, 1H), 3.88(dd, J = 11.2, 8.0 Hz, 1H), 3.73(dd, J = 11.2, 3.2 Hz, 1H), 3.53-3.62(m, 2H), 2.84-2.87(m, 2H). MS(ESI) m/z: 326.2[MH+], C17H18F3NO2 requires 325.13. |
| 64 | (4-CF3-C6H4-O-CH(Ph)-(CH2)4-piperidine) | δ: 7.42(d, J = 8.4 Hz, 2H), 7.23-7.35(m, 5H), 6.88(d, J = 8.8 Hz, 2H), 5.12(dd, J = 8.0, 5.2 Hz, 1H), 2.25-2.34(m, 6H), 1.96-2.08(m, 1H), 1.82-1.91(m, 1H), 1.36-1.59(m, 10H). MS(ESI) m/z: 392.3[MH+], C23H28F3NO requires 391.21. |
| 65 | (4-CF3-C6H4-O-CH(Ph)-(CH2)4-pyrrolidine) | δ: 7.42(d, J = 8.8 Hz, 2H), 7.26-7.35(m, 5H), 6.88(d, J = 9.2 Hz, 2H), 5.12(dd, J = 8.0, 5.2 Hz, 1H), 2.40-2.48(m, 6H), 2.01-2.07(m, 1H), 1.75-1.90(m, 5H), 1.36-1.48(m, 4H). MS(ESI) m/z: 378.3[MH+], C22H26F3NO requires 377.20. |

TABLE 17

| Ex. | Structural Formula | NMR(DMSO-d6) MS |
|---|---|---|
| 66 | (S)-(4-CF3-C6H4-O-CH(Ph)-(CH2)4-NH2) · fumaric acid | δ: 7.55(d, J = 8.8 Hz, 2H), 7.33-7.41(m, 4H), 7.24-7.28(m, 1H), 7.06(d, J = 8.4 Hz, 2H), 6.42(s, 2H), 5.43(dd, J = 7.6, 5.2 Hz, 1H), 2.75(t, J = 7.2 Hz, 2H), 1.91-1.96(m, 1H), 1.76-1.85(m, 1H), 1.56-1.63(m, 2H), 1.46-1.53(m, 1H), 1.34-1.42(m, 1H). MS(ESI) m/z: 324.4[MH+], C18H20F3NO requires 323.35. [α]$_D^{25}$ −2.04° (c = 0.20, MeOH) |
| 67 | (R)-(4-CF3-C6H4-O-CH(Ph)-(CH2)4-NH2) · fumaric acid | δ: 7.55(d, J = 8.8 Hz, 2H), 7.33-7.41(m, 4H), 7.24-7.28(m, 1H), 7.06(d, J = 8.4 Hz, 2H), 6.39(s, 2H), 5.43(dd, J = 8.0, 5.6 Hz, 1H), 2.75(t, J = 6.8 Hz, 2H), 1.91-1.96(m, 1H), 1.78-1.85(m, 1H), 1.46-1.62(m, 3H), 1.34-1.42(m, 1H). MS(ESI) m/z: 324.1[MH+], C18H20F3NO requires 323.35. [α]$_D^{25}$ +2.08° (c = 0.19, MeOH) |

TABLE 17-continued

| Ex. | Structural Formula | NMR(DMSO-d6) MS |
|---|---|---|
| 68 | (F₃CO, F-substituted phenoxy)-phenyl-pentyl-NH₂ with fumaric acid | δ: 7.58(t, J = 8.8 Hz, 1H), 7.34-7.56(m, 4H), 7.26-7.30(m, 1H), 7.06(dd, J = 8.8, 2.0 Hz, 1H), 6.90(dd, J = 8.8, 2.0 Hz, 1H), 6.41(s, 2H), 5.49(dd, J = 7.6, 5.2 Hz, 1H), 2.75(t, J = 7.6 Hz, 2H), 1.93-1.98(m, 1H), 1.78-1.83(m, 1H), 1.56-1.63(m, 2H), 1.45-1.53(m, 1H), 1.33-1.39(m, 1H). MS(ESI) m/z: 342.2[MH+], C18H19F4NO requires 341.14. $[\alpha]_D^{25}$ +1.96° (c = 0.20, MeOH) |
| 69 | (F₃C, F-substituted phenoxy)-phenyl-pentyl-NH₂ with fumaric acid | δ: 7.59(t, J = 8.8 Hz, 1H), 7.34-7.57(m, 4H), 7.26-7.30(m, 1H), 7.06(dd, J = 9.2, 2.0 Hz, 1H), 6.90(dd, J = 8.8, 2.0 Hz, 1H), 6.39(s, 2H), 5.49(dd, J = 7.6, 5.2 Hz, 1H), 2.74(t, J = 7.6 Hz, 2H), 1.93-1.97(m, 1H), 1.78-1.84(m, 1H), 1.56-1.62(m, 2H), 1.45-1.55(m, 1H), 1.33-1.40(m, 1H). MS(ESI) m/z: 342.3[MH+], C18H19F4NO requires 341.14. $[\alpha]_D^{25}$ -2.30° (c = 0.26, MeOH) |

TABLE 18

| Ex. | Structural Formula | NMR(DMSO-d6) MS |
|---|---|---|
| 70 | (F₃CO-phenoxy)-phenyl-pentyl-NH₂ with fumaric acid | δ: 7.32-7.41(m, 4H), 7.24-7.27(m, 1H), 7.18(d, J = 8.4 Hz, 2H), 6.94-6.98(m, 2H), 6.43(s, 2H), 5.31(dd, J = 7.6, 5.2 Hz, 1H), 2.75(t, J = 7.2 Hz, 2H), 1.88-1.93(m, 1H), 1.74-1.82(m, 1H), 1.56-1.63(m, 2H), 1.47-1.56(m, 1H), 1.33-1.42(m, 1H). MS(ESI) m/z: 340.1[MH+], C18H20F3NO2 requires 339.14. $[\alpha]_D^{25}$ +2.02° (c = 0.23, MeOH) |
| 71 | (F₃CO-phenoxy)-phenyl-pentyl-NH₂ with fumaric acid | δ: 7.32-7.40(m, 4H), 7.24-7.28(m, 1H), 7.18(d, J = 8.4 Hz, 2H), 6.94-6.98(m, 2H), 6.41(s, 2H), 5.31(dd, J = 7.6, 5.2 Hz, 1H), 2.75(t, J = 7.2 Hz, 2H), 1.88-1.94(m, 1H), 1.74-1.83(m, 1H), 1.47-1.62(m, 3H), 1.33-1.42(m, 1H). MS(ESI) m/z: 340.2[MH+], C18H20F3NO2 requires 339.14. $[\alpha]_D^{25}$ -2.40° (c = 0.25, MeOH) |
| 72 | (F₃C, F-substituted phenoxy)-phenyl-pentyl-NH₂ with fumaric acid | δ: 7.59(t, J = 8.8 Hz, 1H), 7.33-7.57(m, 4H), 7.26-7.30(m, 1H), 7.06(dd, J = 8.8, 2.0 Hz, 1H), 6.90(d, J = 8.8, 1H), 6.39(s, 2H), 5.49(dd, J = 7.6, 5.2 Hz, 1H), 2.74(t, J = 7.6 Hz, 2H), 1.92-1.97(m, 1H), 1.78-1.83(m, 1H), 1.56-1.62(m, 2H), 1.45-1.55(m, 1H), 1.33-1.40(m, 1H). MS(ESI) m/z: 342.2[MH+], C18H19F4NO requires 341.14. |

TABLE 18-continued

| Ex. | Structural Formula | NMR(DMSO-d6) MS |
|---|---|---|
| 73 | F$_3$CO-C$_6$H$_4$-O-CH(C$_6$H$_5$)-(CH$_2$)$_4$-NH$_2$ with HOOC-CH=CH-COOH | δ: 7.32-7.40m, 4H), 7.24-7.27(m, 1H), 7.19(d, J = 8.8 Hz, 2H), 6.95-6.99(m, 2H), 6.40(s, 2H), 5.31(dd, J = 7.6, 5.2 Hz, 1H), 2.74(t, J = 7.2 Hz, 2H), 1.88-1.94 (m, 1H), 1.73-1.82(m, 1H), 1.56-1.62(m, 2H), 1.46-1.56(m, 1H), 1.33-1.44(m, 1H). MS(ESI) m/z: 340.2[MH+], C18H20F3NO2 requires 339.14. |

Experimental Example 1 Activity Evaluation Test In Vitro

1) LAT-1 Inhibitory Activity and LAT-2 Inhibitory Activity Inhibitory Effect on Uptake of Amino Acid into Human LAT-1 Stably Expressing Cell Line and LAT-2 Stably Expressing Cell Line Expression vector each expressing a gene was inserted using Lipofectamine 2000 (Invitrogen) to cultured cell line HEK293 cell derived from human fetus renal cell. The resistant strains were selected using G418, and among them, the strains showing human LAT-1- or LAT-2-specific uptake of amino acid were established as stably expressing cell lines, respectively.

The above-mentioned stably expressing cells were plated on a 24-well collagen plate at $1.2 \times 10^5$ cells/well, and, after 48 hr, the cells were washed (×3) with uptake buffer (Na$^{2+}$-free Hank's balanced salt solution (HBSS) pH7.4) kept at 37° C. Each test compound (0.1, 1, 3, 10, 30, 100, 300 and 1000 μM) was added thereto, and the mixture was kept at 37° C. for 3 min. [$^{14}$C]L-leucine or alanine (1 μM) was added thereto, and [$^{14}$C]L-leucine or alanine (1 μM) was uptaken for 1 min. The mixture was washed with ice-cold uptake buffer (×3). Then, the cells were dissolved in 0.1M NaOH aqueous solution (500 μL), and the protein concentration was measured using the 20 μL of the solution. The uptaken radioactivity was measured using the remaining solution. The measured results were corrected with the protein concentration. The results were evaluated as inhibitory capacity 50%, i.e., IC$_{50}$, which corresponds to the concentration inhibiting 50% of the cellular uptake of amino acid. IC$_{50}$ (μM) of the representative Example compounds of the present invention are shown in Table 19.

TABLE 19

| Example compound | LAT-1 inhibitory activity/IC$_{50}$ (μM) | LAT-2 inhibitory activity/IC$_{50}$ (μM) |
|---|---|---|
| 1 | 57.5 | 146 |
| 6 | 89.1 | 128 |
| 12 | 63.0 | 100 |
| 26 | 57.0 | 253 |
| 29 | 76.0 | 218 |
| 44 | 39.4 | 169 |
| 48 | 56.6 | 357 |
| 50 | 123 | 313 |
| 51 | 261 | 261 |
| 53 | 146 | 258 |
| 54 | 177 | 300 |
| 66 | 62.8 | 194 |
| 67 | 96.2 | 207 |
| 68 | 36.4 | 156 |
| 69 | 69.0 | 53.0 |

TABLE 19-continued

| Example compound | LAT-1 inhibitory activity/IC$_{50}$ (μM) | LAT-2 inhibitory activity/IC$_{50}$ (μM) |
|---|---|---|
| 70 | 36.6 | 131.3 |
| 71 | 244.2 | 131.3 |

The above-mentioned human LAT-1 stably expressing cells were plated on a 24-well collagen plate at $1.2 \times 10^5$ cells/well, and, after 48 hr, the cells were washed (×3) with new culture solution (MEM medium (containing non-essential amino acid)) kept at 37° C. Each test compound (0.1, 1, 3, 10 and 30 μM) was added thereto, and the mixture was kept at 37° C. for 3 min. [$^{14}$C]L-leucine was added thereto, and [$^{14}$C]L-leucine was uptaken in the culture solution for 120 min. The mixture was washed (×3) with ice-cold buffer (Na$^{2+}$-free Hank's balanced salt solution (HBSS) pH7.4). Then, the cells were dissolved in 0.1M NaOH aqueous solution (500 μL), and the protein concentration was measured using the 20 μL of the solution. The uptaken radioactivity was measured using the remaining solution. The measured results were corrected with the protein concentration. The results were evaluated as inhibitory capacity 50%, i.e., IC$_{50}$, which corresponds to the concentration inhibiting 50% of the cellular uptake of amino acid. IC$_{50}$ (μM) of the representative Example compounds of the present invention are shown in Table 20.

TABLE 20

| Example compound | LAT-1 inhibitory activity/IC$_{50}$ (μM) |
|---|---|
| 70 | 10.4 |

2) Growth Inhibitory Effect on Human Pancreatic Cancer Cell Line MIAPaCa-2

MIAPaCa-2 cells were plated on a 12-well plate at 2000 cells/well, and cultured for 48 hr without addition of test compound. 48 hr after the beginning of the culture, each test compound (0.03, 0.1, 0.3, 1, 3, 6, 10, 30, 100 μM) was added thereto in the presence of 0.2% DMSO. The cells were counted every 24 hr for 5 days, and the inhibitory effect on the MIAPaCa-2 cell growth was observed by Trypan-Blue method. The results were evaluated as inhibitory capacity 50%, i.e., IC$_{50}$, which corresponds to the concentration inhibiting 50% of the cell growth inhibitory activity. IC$_{50}$ (μM) of the representative Example compounds of the present invention are shown in Table 21.

TABLE 21

| Example compound | cell growth inhibitory activity/IC$_{50}$ (μM) |
| --- | --- |
| 66 | 0.17 |
| 67 | 4.16 |
| 68 | 0.43 |
| 69 | 0.83 |
| 70 | 0.11 |
| 71 | 3.36 |

Experimental Example 2 Biological Activity Evaluation Test Enlargement Inhibitory Effect on Subcutaneous Tumor Derived from Human Pancreatic Cancer Cell Line MIAPaCa-2 in Nude Mice Tumor tissue (0.1 g) derived from MIAPaCa-2 cell was subcutaneously transplanted into female nude mice (6-week old, BALB/cAJc1-nu), which the tumor tissue was formed in different nude mice in advance. 5% MC suspension was prepared from saline and each test compound (1 mg/kg), and it was orally-administered once a day for 7 days from 2 days after transplant. The time-dependent change of the tumor volume was measured by measuring (major axis×minor axis×minor axis)/2 of the tumor volume (weight) according to the method in Sawa, Jun Wu, Takaaki Akaike, and Hiroshi Maeda (2000) Cancer research 60, 666-671.

The tumor volume after 15 to 21 days administration of compound administration group was compared with those of control group, and the tumor growth inhibitory ratio was calculated. The anti-tumor action was evaluated as tumor growth inhibitory ratio. When 1 mg/kg of the present compound was orally-administered, the tumor growth inhibitory ratios are shown in Table 22.

TABLE 22

| Example compound | tumor growth inhibitory ratio (%) |
| --- | --- |
| 2 | 80.5 |
| 68 | 84.4 |
| 69 | 85.5 |
| 70 | 90.2 |
| 71 | 85.9 |
| 72 | 84.4 |
| 73 | 83.6 |

Formulation Example 1 (Production of Capsule)

| | |
| --- | --- |
| 1) compound of Example 1 | 30 mg |
| 2) finely divided powder cellulose | 10 mg |
| 3) lactose | 19 mg |
| 4) magnesium stearate | 1 mg |
| Total | 60 mg |

1), 2), 3) and 4) are mixed and filled in a gelatin capsule.

Formulation Example 2 (Production of Tablet)

| | |
| --- | --- |
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

Since the compound of the present invention has a selective inhibitory activity against highly-expressed LAT-1 in tumor cell, it is useful as an anti-cancer agent.

This application is based on patent application No. 2013-008785 filed on Jan. 21, 2013 in Japan, the contents of which are encompassed in full herein.

The invention claimed is:

1. A compound represented by the formula (I):

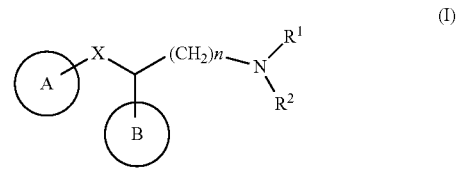

wherein

Ring A is an optionally substituted cyclic group,

Ring B is an optionally substituted cyclic group, $R^1$ and $R^2$ are each independently a hydrogen atom, an optionally substituted alkyl group or an optionally substituted cycloalkyl group, X is O, S, S(O), or S(O)$_2$, and n is an integer of 4 to 6, or a salt thereof.

2. The compound or salt of claim 1, wherein Ring A is a $C_{6-14}$ aryl group, an aromatic heterocyclic group or a non-aromatic heterocyclic group, each optionally substituted.

3. The compound or salt of claim 1, wherein Ring A is optionally substituted phenyl.

4. The compound or salt of claim 1, wherein Ring B is an optionally substituted aromatic group.

5. The compound or salt of claim 1, wherein Ring B is phenyl or thienyl, each optionally substituted.

6. The compound or salt of claim 1, wherein $R^1$ and $R^2$ are each independently a hydrogen atom or a $C_{1-6}$ alkyl group.

7. The compound or salt of claim 1, wherein $R^1$ and $R^2$ are each independently a hydrogen atom or a $C_{1-3}$ alkyl group.

8. The compound or salt of claim 1, wherein n is 4 or 5.

9. The compound or salt of claim 1, wherein n is 4.

10. The compound or salt of claim 1, wherein X is O.

11. A pharmaceutical composition comprising the compound or salt of claim 1, and a pharmaceutically acceptable carrier.

12. A LAT-1 inhibitor comprising the compound or salt of claim 1.

13. A method of treating cancer selected from the group consisting of pancreatic cancer, lung cancer, colorectal cancer, breast cancer, brain tumor, stomach cancer, liver cancer, esophageal cancer, head and neck cancer, and tongue cancer in a subject, comprising administering to the subject an effective amount of a compound represented by the formula (I):

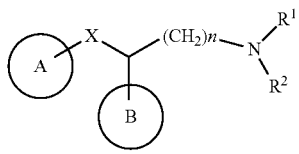

(I)

wherein
Ring A is optionally substituted phenyl,
Ring B is optionally substituted phenyl,
$R^1$ and $R^2$ are each independently a hydrogen atom, an optionally substituted alkyl group or an optionally substituted cycloalkyl group,
X is O, and
n is an integer of 4 to 6,
or a salt thereof.

14. The method of claim 13, wherein the cancer is pancreatic cancer or lung cancer.

15. A compound represented by the formula (12):

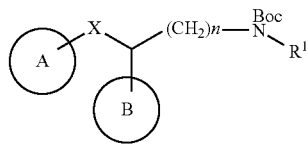

(12)

wherein
Ring A is an optionally substituted cyclic group,
Ring B is an optionally substituted cyclic group,
$R^1$ is a hydrogen atom, an optionally substituted alkyl group or an optionally substituted cycloalkyl group,
$X^1$ is O, S or $NR^3$ wherein $R^3$ is a hydrogen atom or an optionally substituted alkyl group, and
n is an integer of 4 to 6,
or a salt thereof.

16. The method of claim 13, wherein the cancer is selected from the group consisting of colorectal cancer, breast cancer, brain tumor, stomach cancer, and liver cancer.

* * * * *